(12) United States Patent
Boyajian et al.

(10) Patent No.: US 8,394,146 B2
(45) Date of Patent: Mar. 12, 2013

(54) VERTEBRAL ANCHORING METHODS

(75) Inventors: Thomas Boyajian, Wilmington, MA (US); Almir Velagic, Melrose, MA (US); Robert Kevin Moore, Natick, MA (US); Christopher Tarapata, North Andover, MA (US); Jacob Einhorn, Brookline, MA (US); Gregory Lambrecht, Natick, MA (US); Sean Kavanaugh, Eastham, MA (US)

(73) Assignee: Intrinsic Therapeutics, Inc., Woburn, MA (US)

( * ) Notice: Subject to any disclaimer, the term of this patent is extended or adjusted under 35 U.S.C. 154(b) by 42 days.

(21) Appl. No.: 13/175,278

(22) Filed: Jul. 1, 2011

(65) Prior Publication Data

US 2011/0264227 A1 Oct. 27, 2011

Related U.S. Application Data

(63) Continuation of application No. 11/641,253, filed on Dec. 19, 2006, now Pat. No. 7,972,337.

(60) Provisional application No. 60/754,237, filed on Dec. 28, 2005.

(51) Int. Cl.
*A61F 2/44* (2006.01)

(52) U.S. Cl. .................... 623/17.16; 606/75

(58) Field of Classification Search .............. 606/60, 606/70, 71, 74, 75, 246–279, 280–299, 300–331; 623/17.11–17.16
See application file for complete search history.

(56) References Cited

U.S. PATENT DOCUMENTS

| | | |
|---|---|---|
| 3,526,567 A | 9/1970 | Macone |
| 3,867,728 A | 2/1975 | Stubstad et al. |
| 3,875,595 A | 4/1975 | Froning |
| 3,921,632 A | 11/1975 | Bardani |
| 3,997,138 A | 12/1976 | Crock et al. |
| 4,041,550 A | 8/1977 | Frazier |
| 4,078,559 A | 3/1978 | Nissinen |
| 4,280,954 A | 7/1981 | Yannas et al. |
| 4,349,921 A | 9/1982 | Kuntz |
| 4,365,357 A | 12/1982 | Draenert |
| 4,473,070 A | 9/1984 | Matthews et al. |
| 4,502,161 A | 3/1985 | Wall |
| 4,532,926 A | 8/1985 | O'Holla |
| 4,573,454 A | 3/1986 | Hoffman |

(Continued)

FOREIGN PATENT DOCUMENTS

| | | |
|---|---|---|
| EP | 0277678 | 8/1988 |
| EP | 0298233 | 1/1989 |

(Continued)

OTHER PUBLICATIONS

Ahlgren, B.D., et al., "Anular Incision Technique on the Strength and Multidirectional Flexibility of the Healing Intervertebral Disc," *Spine*, 19 (8) : 948-954 (1994).

(Continued)

*Primary Examiner* — Kevin T Truong
*Assistant Examiner* — Christopher Beccia
(74) *Attorney, Agent, or Firm* — Knobbe, Martens, Olson & Bear LLP

(57) ABSTRACT

Embodiments of the invention relate generally to tissue anchors and methods of delivering same to the intervertebral disc or other sites within the body. In some embodiments, the anchors provide pull-out resistance, stability and/or maximize contact with tissue involving a minimum amount of penetration. In some embodiments, delivery methods are minimally invasive and include linear, lateral, and off-angle implantation or driving of anchors along, against or within tissue surfaces.

20 Claims, 39 Drawing Sheets

U.S. PATENT DOCUMENTS

| | | |
|---|---|---|
| 4,665,906 A | 5/1987 | Jervis |
| 4,738,251 A | 4/1988 | Plaza |
| 4,741,330 A | 5/1988 | Hayhurst |
| 4,743,256 A | 5/1988 | Brantigan |
| 4,744,364 A | 5/1988 | Kensey |
| 4,755,184 A | 7/1988 | Silverberg |
| 4,772,287 A | 9/1988 | Ray et al. |
| 4,781,190 A | 11/1988 | Lee |
| 4,798,205 A | 1/1989 | Bonomo et al. |
| 4,815,453 A | 3/1989 | Cotrel |
| 4,821,942 A | 4/1989 | Richards et al. |
| 4,837,285 A | 6/1989 | Berg et al. |
| 4,852,568 A | 8/1989 | Kensey |
| 4,854,304 A | 8/1989 | Zielke |
| 4,863,477 A | 9/1989 | Monson |
| 4,871,094 A | 10/1989 | Gall et al. |
| 4,873,976 A | 10/1989 | Schreiber |
| 4,874,389 A | 10/1989 | Downey |
| 4,890,612 A | 1/1990 | Kensey |
| 4,904,260 A | 2/1990 | Ray et al. |
| 4,911,718 A | 3/1990 | Lee et al. |
| 4,917,704 A | 4/1990 | Frey et al. |
| 4,919,667 A | 4/1990 | Richmond |
| 4,932,969 A | 6/1990 | Frey et al. |
| 4,936,844 A | 6/1990 | Chandler et al. |
| 4,946,378 A | 8/1990 | Hirayama et al. |
| 4,946,467 A | 8/1990 | Ohi et al. |
| 4,955,908 A | 9/1990 | Frey et al. |
| 4,994,073 A | 2/1991 | Green et al. |
| 5,002,576 A | 3/1991 | Fuhrmann et al. |
| 5,007,909 A | 4/1991 | Rogozinski |
| 5,015,255 A | 5/1991 | Kuslich |
| 5,021,059 A | 6/1991 | Kensey et al. |
| 5,035,716 A | 7/1991 | Downey |
| 5,046,513 A | 9/1991 | Gatturna et al. |
| 5,047,055 A | 9/1991 | Bao et al. |
| 5,053,046 A | 10/1991 | Janese |
| 5,059,206 A | 10/1991 | Winters |
| 5,061,274 A | 10/1991 | Kensey |
| 5,071,437 A | 12/1991 | Steffee |
| 5,100,422 A | 3/1992 | Berguer et al. |
| 5,108,420 A | 4/1992 | Marks |
| 5,108,438 A | 4/1992 | Stone |
| 5,116,357 A | 5/1992 | Eberbach |
| 5,122,155 A | 6/1992 | Eberbach |
| 5,123,926 A | 6/1992 | Pisharodi |
| 5,129,906 A | 7/1992 | Ross et al. |
| 5,141,515 A | 8/1992 | Eberbach |
| 5,147,374 A | 9/1992 | Fernandez |
| 5,147,387 A | 9/1992 | Jansen et al. |
| 5,171,252 A | 12/1992 | Friedland |
| 5,171,259 A | 12/1992 | Inoue |
| 5,171,279 A | 12/1992 | Mathews |
| 5,171,280 A | 12/1992 | Baumgartner |
| 5,171,281 A | 12/1992 | Parsons et al. |
| 5,176,692 A | 1/1993 | Wilk et al. |
| 5,180,393 A | 1/1993 | Commarmond |
| 5,189,789 A | 3/1993 | Hall |
| 5,192,300 A | 3/1993 | Fowler |
| 5,192,301 A | 3/1993 | Kamiya et al. |
| 5,192,326 A | 3/1993 | Bao et al. |
| 5,201,729 A | 4/1993 | Hertzmann et al. |
| 5,203,787 A | 4/1993 | Noblitt et al. |
| 5,207,649 A | 5/1993 | Aruny |
| 5,217,471 A | 6/1993 | Burkhart |
| 5,219,359 A | 6/1993 | McQuilkin et al. |
| 5,222,962 A | 6/1993 | Burkhart |
| 5,222,974 A | 6/1993 | Kensey et al. |
| 5,236,438 A | 8/1993 | Wilk |
| 5,239,982 A | 8/1993 | Trauthen |
| 5,242,448 A | 9/1993 | Pettine et al. |
| 5,254,133 A | 10/1993 | Seid |
| 5,258,000 A | 11/1993 | Gianturco |
| 5,258,031 A | 11/1993 | Salib et al. |
| 5,258,043 A | 11/1993 | Stone |
| 5,269,783 A | 12/1993 | Sander |
| 5,282,827 A | 2/1994 | Kensey et al. |
| 5,292,332 A | 3/1994 | Lee |
| 5,306,311 A | 4/1994 | Stone et al. |
| 5,312,435 A | 5/1994 | Nash et al. |
| 5,320,633 A | 6/1994 | Allen et al. |
| 5,320,644 A | 6/1994 | Baumgartner |
| 5,342,393 A | 8/1994 | Stack |
| 5,342,394 A | 8/1994 | Matsuno et al. |
| 5,352,224 A | 10/1994 | Westermann |
| 5,356,432 A | 10/1994 | Rutkow et al. |
| 5,366,460 A | 11/1994 | Eberbach |
| 5,368,602 A | 11/1994 | de la Torre |
| 5,370,697 A | 12/1994 | Baumgartner |
| 5,383,477 A | 1/1995 | DeMatteis |
| 5,383,905 A | 1/1995 | Golds et al. |
| 5,387,213 A | 2/1995 | Breard et al. |
| 5,391,182 A | 2/1995 | Chin |
| 5,397,331 A | 3/1995 | Himpens et al. |
| 5,397,332 A | 3/1995 | Kammerer et al. |
| 5,397,355 A | 3/1995 | Marin et al. |
| 5,405,360 A | 4/1995 | Tovey |
| 5,425,773 A | 6/1995 | Boyd et al. |
| 5,431,658 A | 7/1995 | Moskovich |
| 5,437,631 A | 8/1995 | Janzen |
| 5,445,639 A | 8/1995 | Kuslich et al. |
| 5,456,720 A | 10/1995 | Schultz et al. |
| 5,464,407 A | 11/1995 | McGuire |
| 5,478,353 A | 12/1995 | Yoon |
| 5,500,000 A | 3/1996 | Feagin et al. |
| 5,507,754 A | 4/1996 | Green et al. |
| 5,514,130 A | 5/1996 | Baker |
| 5,514,180 A | 5/1996 | Heggeness et al. |
| 5,520,700 A | 5/1996 | Beyar et al. |
| 5,522,898 A | 6/1996 | Bao et al. |
| 5,531,759 A | 7/1996 | Kensey et al. |
| 5,534,028 A | 7/1996 | Bao et al. |
| 5,534,030 A | 7/1996 | Navarro et al. |
| 5,545,178 A | 8/1996 | Kensey et al. |
| 5,545,229 A | 8/1996 | Parsons et al. |
| 5,549,617 A | 8/1996 | Green et al. |
| 5,549,679 A | 8/1996 | Kuslich |
| 5,552,100 A | 9/1996 | Shannon et al. |
| 5,556,428 A | 9/1996 | Shah |
| 5,556,429 A | 9/1996 | Felt |
| 5,562,689 A | 10/1996 | Green et al. |
| 5,562,735 A | 10/1996 | Margulies |
| 5,562,736 A | 10/1996 | Ray et al. |
| 5,562,738 A | 10/1996 | Boyd et al. |
| 5,569,252 A | 10/1996 | Justin et al. |
| 5,571,189 A | 11/1996 | Kuslich |
| 5,582,616 A | 12/1996 | Bolduc et al. |
| 5,591,204 A | 1/1997 | Jansen et al. |
| 5,591,223 A | 1/1997 | Lock et al. |
| 5,591,235 A | 1/1997 | Kuslich |
| 5,609,634 A | 3/1997 | Voydeville |
| 5,611,801 A | 3/1997 | Songer |
| 5,613,974 A | 3/1997 | Andreas et al. |
| 5,620,012 A | 4/1997 | Benderev et al. |
| 5,624,463 A | 4/1997 | Stone et al. |
| 5,626,613 A | 5/1997 | Schmieding |
| 5,634,931 A | 6/1997 | Kugel |
| 5,634,936 A | 6/1997 | Linden et al. |
| 5,641,373 A | 6/1997 | Shannon et al. |
| 5,645,084 A | 7/1997 | McKay |
| 5,645,597 A | 7/1997 | Krapiva |
| 5,649,926 A | 7/1997 | Howland |
| 5,658,286 A | 8/1997 | Sava |
| 5,658,343 A | 8/1997 | Hauselmann et al. |
| 5,662,683 A | 9/1997 | Kay |
| 5,669,935 A | 9/1997 | Rosenman et al. |
| 5,674,294 A | 10/1997 | Bainville et al. |
| 5,674,295 A | 10/1997 | Ray et al. |
| 5,674,296 A | 10/1997 | Bryan et al. |
| 5,676,698 A | 10/1997 | Janzen et al. |
| 5,676,701 A | 10/1997 | Yuan et al. |
| 5,681,310 A | 10/1997 | Yuan et al. |
| 5,681,351 A | 10/1997 | Jamiolkowski et al. |
| 5,683,465 A | 11/1997 | Shinn et al. |
| 5,690,674 A | 11/1997 | Diaz |
| 5,695,525 A | 12/1997 | Mulhauser et al. |
| 5,702,450 A | 12/1997 | Bisserie |

| | | | | | | |
|---|---|---|---|---|---|---|
| 5,702,451 A | 12/1997 | Biedermann et al. | 6,027,527 A | 2/2000 | Asano et al. | |
| 5,702,454 A | 12/1997 | Baumgartner | 6,066,175 A | 5/2000 | Henderson et al. | |
| 5,702,462 A | 12/1997 | Oberlander | 6,073,051 A | 6/2000 | Sharkey et al. | |
| 5,704,936 A | 1/1998 | Mazel | 6,093,205 A | 7/2000 | McLeod et al. | |
| 5,705,780 A | 1/1998 | Bao | 6,093,207 A | 7/2000 | Pisharodi | |
| 5,716,408 A | 2/1998 | Eldridge et al. | 6,096,044 A | 8/2000 | Boyd et al. | |
| 5,716,409 A | 2/1998 | Debbas | 6,099,791 A | 8/2000 | Shannon et al. | |
| 5,716,413 A | 2/1998 | Walter et al. | 6,102,930 A | 8/2000 | Simmons, Jr. | |
| 5,716,416 A | 2/1998 | Lin | 6,105,581 A | 8/2000 | Eggers et al. | |
| 5,725,577 A | 3/1998 | Saxon | 6,110,210 A | 8/2000 | Norton et al. | |
| 5,725,582 A | 3/1998 | Bevan et al. | 6,113,639 A | 9/2000 | Ray et al. | |
| 5,728,097 A | 3/1998 | Mathews | 6,120,503 A | 9/2000 | Michelson | |
| 5,728,150 A | 3/1998 | McDonald et al. | 6,120,539 A | 9/2000 | Eldridge et al. | |
| 5,730,744 A | 3/1998 | Justin et al. | 6,124,523 A | 9/2000 | Banas et al. | |
| 5,733,337 A | 3/1998 | Carr, Jr. et al. | 6,126,682 A | 10/2000 | Sharkey et al. | |
| 5,743,917 A | 4/1998 | Saxon | 6,132,465 A | 10/2000 | Ray et al. | |
| 5,746,755 A | 5/1998 | Wood et al. | 6,140,452 A | 10/2000 | Felt et al. | |
| 5,746,765 A | 5/1998 | Kleshinski et al. | 6,146,380 A | 11/2000 | Racz et al. | |
| 5,755,797 A | 5/1998 | Baumgartner | 6,146,420 A | 11/2000 | McKay | |
| 5,766,246 A | 6/1998 | Mulhauser et al. | 6,153,292 A | 11/2000 | Bell et al. | |
| 5,769,864 A | 6/1998 | Kugel | 6,156,067 A | 12/2000 | Bryan et al. | |
| 5,769,893 A | 6/1998 | Shah | 6,174,311 B1 | 1/2001 | Branch et al. | |
| 5,772,661 A | 6/1998 | Michelson | 6,174,323 B1 | 1/2001 | Biggs et al. | |
| 5,776,183 A | 7/1998 | Kanesaka et al. | 6,179,836 B1 | 1/2001 | Eggers et al. | |
| 5,782,831 A | 7/1998 | Sherman et al. | 6,180,848 B1 | 1/2001 | Flament et al. | |
| 5,782,844 A | 7/1998 | Yoon et al. | 6,183,518 B1 | 2/2001 | Ross et al. | |
| 5,785,705 A | 7/1998 | Baker | 6,187,048 B1 | 2/2001 | Milner et al. | |
| 5,800,549 A | 9/1998 | Bao et al. | 6,190,353 B1 | 2/2001 | Makower et al. | |
| 5,800,550 A | 9/1998 | Sertich | 6,190,414 B1 | 2/2001 | Young et al. | |
| 5,810,851 A | 9/1998 | Yoon | 6,203,735 B1 | 3/2001 | Edwin et al. | |
| 5,823,994 A | 10/1998 | Sharkey et al. | 6,206,921 B1 | 3/2001 | Guagliano et al. | |
| 5,824,008 A | 10/1998 | Bolduc et al. | 6,214,039 B1 | 4/2001 | Banas et al. | |
| 5,824,082 A | 10/1998 | Brown | 6,224,630 B1 | 5/2001 | Bao et al. | |
| 5,824,093 A | 10/1998 | Ray et al. | 6,224,631 B1 | 5/2001 | Kohrs et al. | |
| 5,824,094 A | 10/1998 | Serhan et al. | 6,231,597 B1 | 5/2001 | Deem et al. | |
| 5,827,298 A | 10/1998 | Hart et al. | 6,235,059 B1 | 5/2001 | Benezech et al. | |
| 5,836,315 A | 11/1998 | Benderev et al. | 6,240,926 B1 | 6/2001 | Chin Gan et al. | |
| 5,843,082 A | 12/1998 | Yuan et al. | 6,241,722 B1 | 6/2001 | Dobak et al. | |
| 5,843,084 A | 12/1998 | Hart et al. | 6,245,099 B1 | 6/2001 | Edwin et al. | |
| 5,843,173 A | 12/1998 | Shannon et al. | 6,245,107 B1 | 6/2001 | Ferree | |
| 5,846,261 A | 12/1998 | Kotula et al. | 6,248,106 B1 | 6/2001 | Ferree | |
| 5,860,425 A | 1/1999 | Benderev et al. | 6,258,086 B1 | 7/2001 | Ashley et al. | |
| 5,860,977 A | 1/1999 | Zucherman et al. | 6,264,659 B1 | 7/2001 | Ross et al. | |
| 5,865,845 A | 2/1999 | Thalgott | 6,264,695 B1 | 7/2001 | Stoy | |
| 5,865,846 A | 2/1999 | Bryan et al. | 6,267,834 B1 | 7/2001 | Shannon et al. | |
| 5,888,220 A | 3/1999 | Felt et al. | 6,273,912 B1 | 8/2001 | Scholz et al. | |
| 5,888,226 A | 3/1999 | Rogozinski | 6,280,475 B1 | 8/2001 | Bao et al. | |
| 5,893,889 A | 4/1999 | Harrington | 6,299,613 B1 | 10/2001 | Ogilvie et al. | |
| 5,895,426 A | 4/1999 | Scarborough et al. | 6,312,462 B1 | 11/2001 | McDermott et al. | |
| 5,911,701 A | 6/1999 | Miller et al. | RE37,479 E | 12/2001 | Kuslich | |
| 5,916,225 A | 6/1999 | Kugel | 6,325,805 B1 * | 12/2001 | Ogilvie et al. | 606/75 |
| 5,919,235 A | 7/1999 | Husson et al. | 6,340,369 B1 | 1/2002 | Ferree | |
| 5,922,026 A | 7/1999 | Chin | 6,344,058 B1 | 2/2002 | Ferree et al. | |
| 5,922,028 A | 7/1999 | Plouhar et al. | 6,352,557 B1 | 3/2002 | Ferree | |
| 5,928,279 A | 7/1999 | Shannon et al. | 6,355,063 B1 | 3/2002 | Calcote | |
| 5,928,284 A | 7/1999 | Mehdizadeh | 6,364,908 B1 | 4/2002 | Ysebaert | |
| 5,935,147 A | 8/1999 | Kensey et al. | 6,371,990 B1 | 4/2002 | Ferree | |
| 5,947,968 A | 9/1999 | Rogozinski | 6,383,214 B1 | 5/2002 | Banas et al. | |
| 5,954,716 A | 9/1999 | Sharkey et al. | 6,387,130 B1 | 5/2002 | Stone et al. | |
| 5,954,767 A | 9/1999 | Pajotin et al. | 6,395,033 B1 | 5/2002 | Pepper | |
| 5,957,939 A | 9/1999 | Heaven et al. | 6,398,803 B1 | 6/2002 | Layne et al. | |
| 5,961,545 A | 10/1999 | Lentz et al. | 6,402,680 B2 | 6/2002 | Mortier et al. | |
| 5,972,000 A | 10/1999 | Beyar et al. | 6,402,750 B1 | 6/2002 | Atkinson et al. | |
| 5,972,007 A | 10/1999 | Sheffield et al. | 6,406,420 B1 | 6/2002 | McCarthy et al. | |
| 5,972,022 A | 10/1999 | Huxel | 6,416,537 B1 | 7/2002 | Martakos et al. | |
| 5,976,174 A | 11/1999 | Ruiz | 6,419,702 B1 | 7/2002 | Ferree | |
| 5,976,186 A | 11/1999 | Bao et al. | 6,419,704 B1 | 7/2002 | Ferree | |
| 5,976,192 A | 11/1999 | McIntyre et al. | 6,425,900 B1 | 7/2002 | Knodel et al. | |
| 5,980,504 A | 11/1999 | Sharkey et al. | 6,425,919 B1 | 7/2002 | Lambrecht et al. | |
| 5,989,256 A | 11/1999 | Kuslich et al. | 6,425,924 B1 | 7/2002 | Rousseau | |
| 5,993,448 A | 11/1999 | Remmler | 6,428,575 B2 | 8/2002 | Koo et al. | |
| 6,001,056 A | 12/1999 | Jassawalla et al. | 6,428,576 B1 | 8/2002 | Haldimann | |
| 6,001,130 A | 12/1999 | Bryan et al. | 6,436,143 B1 | 8/2002 | Ross et al. | |
| 6,007,570 A | 12/1999 | Sharkey et al. | 6,443,988 B2 | 9/2002 | Felt et al. | |
| 6,007,575 A | 12/1999 | Samuels | 6,454,804 B1 | 9/2002 | Ferree | |
| 6,017,346 A | 1/2000 | Grotz | 6,458,131 B1 | 10/2002 | Ray | |
| 6,019,792 A | 2/2000 | Cauthen | 6,482,235 B1 | 11/2002 | Lambrecht et al. | |
| 6,019,793 A | 2/2000 | Perren et al. | 6,491,690 B1 | 12/2002 | Goble et al. | |
| 6,024,096 A | 2/2000 | Buckberg | 6,503,269 B2 | 1/2003 | Neild et al. | |

| Patent | Type | Date | Inventor |
|---|---|---|---|
| 6,508,828 | B1 | 1/2003 | Akerfeldt et al. |
| 6,508,839 | B1 | 1/2003 | Lambrecht et al. |
| 6,514,194 | B2 | 2/2003 | Schweich et al. |
| 6,520,967 | B1 | 2/2003 | Cauthen |
| 6,530,932 | B1 | 3/2003 | Swayze et al. |
| 6,530,933 | B1 | 3/2003 | Yeung et al. |
| 6,537,198 | B1 | 3/2003 | Vidlund et al. |
| 6,551,320 | B2 | 4/2003 | Lieberman |
| 6,551,356 | B2 | 4/2003 | Roussean |
| 6,558,387 | B2 | 5/2003 | Errico et al. |
| 6,576,017 | B2 | 6/2003 | Foley et al. |
| 6,579,291 | B1 | 6/2003 | Keith et al. |
| 6,582,433 | B2 | 6/2003 | Yun |
| 6,589,160 | B2 | 7/2003 | Schweich et al. |
| 6,592,625 | B2 | 7/2003 | Cauthen |
| 6,599,311 | B1 | 7/2003 | Biggs et al. |
| 6,607,530 | B1 | 8/2003 | Carl et al. |
| 6,610,094 | B2 | 8/2003 | Husson |
| 6,613,074 | B1 | 9/2003 | Mitelberg et al. |
| 6,616,669 | B2 | 9/2003 | Ogilvie et al. |
| 6,616,684 | B1 | 9/2003 | Vidlund et al. |
| 6,620,196 | B1 | 9/2003 | Trieu |
| 6,626,909 | B2 | 9/2003 | Chin |
| 6,626,916 | B1 | 9/2003 | Yeung et al. |
| 6,645,211 | B2 | 11/2003 | Magana |
| 6,645,247 | B2 | 11/2003 | Ferree |
| 6,648,903 | B1 | 11/2003 | Pierson |
| 6,648,915 | B2 | 11/2003 | Sazy |
| 6,648,918 | B2 | 11/2003 | Ferree |
| 6,648,919 | B2 | 11/2003 | Ferree |
| 6,648,920 | B2 | 11/2003 | Ferree |
| 6,652,585 | B2 | 11/2003 | Lange |
| 6,685,695 | B2 | 2/2004 | Ferree |
| 6,689,125 | B1 | 2/2004 | Keith et al. |
| 6,689,140 | B2 | 2/2004 | Cohen |
| 6,712,853 | B2 | 3/2004 | Kuslich |
| 6,719,797 | B1 | 4/2004 | Ferree |
| 6,723,038 | B1 | 4/2004 | Schroeder et al. |
| 6,726,696 | B1 | 4/2004 | Houser et al. |
| 6,730,127 | B2 | 5/2004 | Michelson |
| 6,733,496 | B2 | 5/2004 | Sharkey et al. |
| 6,733,531 | B1 | 5/2004 | Trieu |
| 6,736,815 | B2 | 5/2004 | Ginn |
| 6,749,605 | B2 | 6/2004 | Ashley et al. |
| 6,755,777 | B2 | 6/2004 | Schweich et al. |
| 6,783,546 | B2 | 8/2004 | Zucherman et al. |
| 6,793,618 | B2 | 9/2004 | Schweich et al. |
| 6,793,677 | B2 | 9/2004 | Ferree |
| 6,805,695 | B2 | 10/2004 | Keith et al. |
| 6,821,276 | B2 | 11/2004 | Lambrecht et al. |
| 6,821,277 | B2 | 11/2004 | Teitelbaum |
| 6,855,166 | B2 | 2/2005 | Kohrs |
| 6,878,167 | B2 | 4/2005 | Ferree |
| 6,883,520 | B2 | 4/2005 | Lambrecht et al. |
| 6,893,466 | B2 | 5/2005 | Trieu |
| 6,932,841 | B2 | 8/2005 | Skylar et al. |
| 6,936,072 | B2 | 8/2005 | Lambrecht et al. |
| 6,964,674 | B1 | 11/2005 | Matsuura et al. |
| 6,966,910 | B2 | 11/2005 | Ritland |
| 6,966,916 | B2 | 11/2005 | Kumar |
| 6,969,404 | B2 | 11/2005 | Ferree |
| 6,974,479 | B2 | 12/2005 | Trieu |
| 6,984,247 | B2 | 1/2006 | Cauthen |
| 6,986,771 | B2 | 1/2006 | Paul et al. |
| 6,989,031 | B2 | 1/2006 | Michelson |
| 6,997,953 | B2 | 2/2006 | Chung et al. |
| 6,997,956 | B2 | 2/2006 | Cauthen |
| 7,004,970 | B2 | 2/2006 | Cauthen |
| 7,008,423 | B2 | 3/2006 | Assaker et al. |
| 7,018,379 | B2 | 3/2006 | Drewry et al. |
| 7,018,414 | B2 | 3/2006 | Brau et al. |
| 7,025,771 | B2 | 4/2006 | Kuslich et al. |
| 7,033,393 | B2 | 4/2006 | Gainer et al. |
| 7,033,395 | B2 | 4/2006 | Cauthen |
| 7,041,138 | B2 | 5/2006 | Lange |
| 7,052,497 | B2 | 5/2006 | Sherman et al. |
| 7,052,516 | B2 | 5/2006 | Cauthen, III et al. |
| 7,056,345 | B2 | 6/2006 | Kuslich |
| 7,077,862 | B2 | 7/2006 | Vidlund et al. |
| 7,094,258 | B2 | 8/2006 | Lambrecht et al. |
| 7,115,129 | B2 | 10/2006 | Heggeness et al. |
| 7,124,761 | B2 | 10/2006 | Lambrecht et al. |
| 7,144,397 | B2 | 12/2006 | Lambrecht et al. |
| 7,150,750 | B2 | 12/2006 | Damarati |
| 7,163,561 | B2 | 1/2007 | Michelson |
| 7,172,627 | B2 | 2/2007 | Fiere et al. |
| 7,182,782 | B2 | 2/2007 | Kirschman |
| 7,189,199 | B2 | 3/2007 | McCarthy et al. |
| 7,189,235 | B2 | 3/2007 | Cauthen |
| 7,198,047 | B2 | 4/2007 | Lambrecht et al. |
| 7,201,775 | B2 | 4/2007 | Gorensek et al. |
| 7,201,776 | B2 | 4/2007 | Ferree et al. |
| 7,214,245 | B1 | 5/2007 | Marcolongo et al. |
| 7,220,281 | B2 | 5/2007 | Lambrecht et al. |
| 7,223,289 | B2 | 5/2007 | Trieu et al. |
| 7,232,463 | B2 | 6/2007 | Falahee |
| 7,237,497 | B2 | 7/2007 | Johnston |
| 7,258,700 | B2 | 8/2007 | Lambrecht et al. |
| 7,273,497 | B2 | 9/2007 | Ferree et al. |
| 7,285,121 | B2 | 10/2007 | Braun et al. |
| 7,297,146 | B2 | 11/2007 | Braun et al. |
| 7,318,840 | B2 | 1/2008 | McKay |
| 7,326,249 | B2 | 2/2008 | Lange |
| 7,331,956 | B2 | 2/2008 | Hovda et al. |
| 7,335,213 | B1 | 2/2008 | Hyde et al. |
| RE40,156 | E | 3/2008 | Sharps et al. |
| 7,344,539 | B2 | 3/2008 | Serhan et al. |
| 7,351,262 | B2 | 4/2008 | Bindseil et al. |
| 7,354,452 | B2 | 4/2008 | Foley |
| 7,354,453 | B2 | 4/2008 | McAfee |
| 7,357,798 | B2 | 4/2008 | Sharps et al. |
| 7,361,193 | B2 | 4/2008 | Frey et al. |
| 7,396,365 | B2 | 7/2008 | Michelson |
| 7,435,260 | B2 | 10/2008 | Ferree |
| 7,445,634 | B2 | 11/2008 | Trieu |
| 7,465,318 | B2 | 12/2008 | Sennett et al. |
| 7,491,179 | B2 | 2/2009 | Roy et al. |
| 7,491,236 | B2 | 2/2009 | Cragg et al. |
| 7,500,978 | B2 | 3/2009 | Gorensek et al. |
| 7,503,936 | B2 | 3/2009 | Trieu |
| 7,507,243 | B2 | 3/2009 | Lambrecht et al. |
| 7,513,911 | B2 | 4/2009 | Lambrecht et al. |
| 7,524,333 | B2 | 4/2009 | Lambrecht et al. |
| 7,534,267 | B2 | 5/2009 | Eckman |
| 7,534,268 | B2 | 5/2009 | Hudgins et al. |
| 7,553,329 | B2 | 6/2009 | Lambrecht et al. |
| 7,553,330 | B2 | 6/2009 | Lambrecht et al. |
| 7,563,282 | B2 | 7/2009 | Lambrecht et al. |
| 7,575,577 | B2 | 8/2009 | Boyd et al. |
| 7,578,835 | B2 | 8/2009 | Wang et al. |
| 7,579,322 | B2 | 8/2009 | Akella et al. |
| 7,601,157 | B2 | 10/2009 | Boyd et al. |
| 7,601,172 | B2 | 10/2009 | Segal et al. |
| 7,611,536 | B2 | 11/2009 | Michelson |
| 7,615,076 | B2 | 11/2009 | Cauthen et al. |
| 7,618,461 | B2 | 11/2009 | Trieu |
| 7,632,313 | B2 | 12/2009 | Bhatnagar et al. |
| 7,637,951 | B2 | 12/2009 | Michelson |
| 7,658,765 | B2 | 2/2010 | Lambrecht et al. |
| 7,666,205 | B2 | 2/2010 | Weikel et al. |
| 7,670,379 | B2 | 3/2010 | Cauthen |
| 7,670,380 | B2 | 3/2010 | Cauthen, III |
| 7,682,392 | B2 | 3/2010 | Serhan et al. |
| 7,682,393 | B2 | 3/2010 | Trieu et al. |
| 7,695,425 | B2 | 4/2010 | Schweich et al. |
| 7,708,733 | B2 | 5/2010 | Sanders et al. |
| 7,713,301 | B2 | 5/2010 | Bao et al. |
| 7,717,961 | B2 | 5/2010 | Lambrecht et al. |
| 7,722,523 | B2 | 5/2010 | Mortier et al. |
| 7,727,241 | B2 | 6/2010 | Gorensek et al. |
| 7,740,659 | B2 | 6/2010 | Zarda et al. |
| 7,740,660 | B2 | 6/2010 | Collins et al. |
| 7,749,230 | B2 | 7/2010 | Yuan et al. |
| 7,749,273 | B2 | 7/2010 | Cauthen et al. |
| 7,749,275 | B2 | 7/2010 | Lambrecht et al. |
| 7,753,941 | B2 | 7/2010 | Keith et al. |
| 7,763,051 | B2 | 7/2010 | Labrom et al. |
| 7,763,077 | B2 | 7/2010 | Friedman et al. |

| Patent/Publication | Date | Name |
|---|---|---|
| 7,766,812 B2 | 8/2010 | Schroeder et al. |
| 7,766,965 B2 | 8/2010 | Bao et al. |
| 7,776,096 B2 | 8/2010 | Cauthen |
| 7,799,060 B2 | 9/2010 | Lange et al. |
| 7,803,188 B2 | 9/2010 | Justis et al. |
| 7,828,850 B2 | 11/2010 | Cauthen, III et al. |
| 7,833,251 B1 | 11/2010 | Ahlgren et al. |
| 7,837,733 B2 | 11/2010 | Collins et al. |
| 7,857,855 B2 | 12/2010 | Ferree |
| 7,857,857 B2 | 12/2010 | Kim |
| 7,867,278 B2 | 1/2011 | Lambrecht et al. |
| 7,879,097 B2 | 2/2011 | Lambrecht et al. |
| 7,905,885 B2 | 3/2011 | Johnson et al. |
| 7,931,679 B2 | 4/2011 | Heggeness et al. |
| 7,931,689 B2 | 4/2011 | Hochschuler et al. |
| 7,935,149 B2 | 5/2011 | Michelson |
| 7,942,928 B2 | 5/2011 | Webler et al. |
| 7,946,236 B2 | 5/2011 | Butcher |
| 7,959,676 B2 | 6/2011 | Thramann et al. |
| 7,959,679 B2 | 6/2011 | Lambrecht |
| 7,959,683 B2 | 6/2011 | Semler et al. |
| 7,967,864 B2 | 6/2011 | Schaller et al. |
| 7,972,337 B2 * | 7/2011 | Boyajian et al. .................. 606/75 |
| 7,972,363 B2 | 7/2011 | Moskowitz et al. |
| 7,993,402 B2 | 8/2011 | Sidler |
| 7,998,213 B2 | 8/2011 | Lambrecht et al. |
| 8,012,211 B2 | 9/2011 | Kuslich |
| 8,021,425 B2 | 9/2011 | Lambrecht et al. |
| 8,025,698 B2 | 9/2011 | Lambrecht et al. |
| 8,105,384 B2 | 1/2012 | Lambrecht et al. |
| 8,114,082 B2 | 2/2012 | Lambrecht et al. |
| 2001/0004710 A1 | 6/2001 | Felt et al. |
| 2002/0026244 A1 | 2/2002 | Trieu |
| 2002/0045942 A1 | 4/2002 | Ham |
| 2002/0049498 A1 | 4/2002 | Yuksel et al. |
| 2002/0111688 A1 | 8/2002 | Cauthen |
| 2002/0120270 A1 | 8/2002 | Trieu et al. |
| 2002/0120337 A1 | 8/2002 | Cauthen |
| 2002/0123807 A1 | 9/2002 | Cauthen, III |
| 2002/0133155 A1 | 9/2002 | Ferree |
| 2002/0143329 A1 * | 10/2002 | Serhan et al. .................... 606/61 |
| 2002/0147496 A1 | 10/2002 | Belef et al. |
| 2002/0151980 A1 | 10/2002 | Cauthen |
| 2002/0165542 A1 | 11/2002 | Ferree |
| 2002/0189622 A1 | 12/2002 | Cauthen, III et al. |
| 2002/0198599 A1 | 12/2002 | Haldimann |
| 2003/0004574 A1 | 1/2003 | Ferree |
| 2003/0040796 A1 | 2/2003 | Ferree |
| 2003/0045937 A1 | 3/2003 | Ginn |
| 2003/0050702 A1 | 3/2003 | Berger |
| 2003/0074075 A1 | 4/2003 | Thomas, Jr. et al. |
| 2003/0074076 A1 | 4/2003 | Ferree et al. |
| 2003/0078579 A1 | 4/2003 | Ferree |
| 2003/0130738 A1 | 7/2003 | Hovda et al. |
| 2003/0149438 A1 | 8/2003 | Nichols et al. |
| 2003/0158604 A1 | 8/2003 | Cauthen et al. |
| 2003/0195514 A1 * | 10/2003 | Trieu et al. ....................... 606/61 |
| 2004/0002764 A1 | 1/2004 | Gainor et al. |
| 2004/0010317 A1 | 1/2004 | Lambrecht et al. |
| 2004/0024465 A1 | 2/2004 | Lambrecht et al. |
| 2004/0034353 A1 | 2/2004 | Michelson |
| 2004/0044412 A1 | 3/2004 | Lambrecht et al. |
| 2004/0097927 A1 | 5/2004 | Yeung et al. |
| 2004/0097980 A1 | 5/2004 | Ferree |
| 2004/0116922 A1 | 6/2004 | Hovda et al. |
| 2004/0138673 A1 | 7/2004 | Lambrecht et al. |
| 2004/0249464 A1 | 12/2004 | Bindseil et al. |
| 2004/0260238 A1 | 12/2004 | Call |
| 2004/0260300 A1 | 12/2004 | Gorensek et al. |
| 2004/0260397 A1 | 12/2004 | Lambrecht et al. |
| 2005/0010205 A1 | 1/2005 | Hovda et al. |
| 2005/0015148 A1 | 1/2005 | Jansen et al. |
| 2005/0027362 A1 | 2/2005 | Williams et al. |
| 2005/0033440 A1 | 2/2005 | Lambrecht et al. |
| 2005/0060038 A1 | 3/2005 | Lambrecht et al. |
| 2005/0143825 A1 * | 6/2005 | Enayati ...................... 623/17.16 |
| 2005/0206039 A1 | 9/2005 | Lambrecht et al. |
| 2005/0278023 A1 | 12/2005 | Zwirkoski |
| 2006/0030857 A1 | 2/2006 | de Villiers et al. |
| 2006/0030884 A1 | 2/2006 | Yeung et al. |
| 2006/0052874 A1 | 3/2006 | Johnson et al. |
| 2006/0085081 A1 | 4/2006 | Shadduck et al. |
| 2006/0089717 A1 * | 4/2006 | Krishna et al. ............. 623/17.11 |
| 2006/0100304 A1 | 5/2006 | Vresilovic et al. |
| 2006/0106461 A1 | 5/2006 | Embry et al. |
| 2006/0129156 A1 | 6/2006 | Cauthen et al. |
| 2006/0161162 A1 | 7/2006 | Lambrecht et al. |
| 2006/0184246 A1 | 8/2006 | Zwirkoski |
| 2006/0200246 A1 | 9/2006 | Lambrecht et al. |
| 2006/0217747 A1 | 9/2006 | Ferree |
| 2006/0253121 A1 | 11/2006 | Gorensek et al. |
| 2006/0265077 A1 | 11/2006 | Zwirkoski |
| 2007/0027471 A1 | 2/2007 | Ferree |
| 2007/0061012 A1 | 3/2007 | Cauthen, III |
| 2007/0067039 A1 | 3/2007 | Lambrecbt et al. |
| 2007/0093822 A1 | 4/2007 | Dutoit et al. |
| 2007/0093912 A1 | 4/2007 | Borden |
| 2007/0118133 A1 | 5/2007 | Lambrecht et al. |
| 2007/0135920 A1 | 6/2007 | Ferree |
| 2007/0142839 A1 | 6/2007 | Ferree |
| 2007/0156152 A1 | 7/2007 | Ferree |
| 2007/0156244 A1 | 7/2007 | Cauthen, III |
| 2007/0162132 A1 | 7/2007 | Messerli |
| 2007/0179623 A1 * | 8/2007 | Trieu et al. .................. 623/17.16 |
| 2007/0185497 A1 | 8/2007 | Cauthen et al. |
| 2007/0198021 A1 | 8/2007 | Wales |
| 2007/0233146 A1 | 10/2007 | Henniges et al. |
| 2007/0239278 A1 | 10/2007 | Heinz |
| 2007/0276494 A1 | 11/2007 | Ferree |
| 2008/0009792 A1 | 1/2008 | Henniges et al. |
| 2008/0015693 A1 | 1/2008 | Le Couedic |
| 2008/0039586 A1 | 2/2008 | Hasenwinkel et al. |
| 2008/0051800 A1 | 2/2008 | Diaz et al. |
| 2008/0082172 A1 | 4/2008 | Jackson |
| 2008/0140126 A1 | 6/2008 | Ferree |
| 2008/0172058 A1 | 7/2008 | Trieu et al. |
| 2008/0195119 A1 | 8/2008 | Ferree |
| 2008/0221686 A1 | 9/2008 | Ferree |
| 2008/0243256 A1 | 10/2008 | Ferree |
| 2008/0269898 A1 | 10/2008 | Carls et al. |
| 2009/0012540 A1 | 1/2009 | Ferguson et al. |
| 2009/0024165 A1 | 1/2009 | Ferree |
| 2009/0118833 A1 | 5/2009 | Hudgins et al. |
| 2009/0143862 A1 | 6/2009 | Trieu |
| 2009/0157087 A1 | 6/2009 | Wei et al. |
| 2009/0187249 A1 | 7/2009 | Osman |
| 2009/0204216 A1 | 8/2009 | Biedermann et al. |
| 2009/0204220 A1 | 8/2009 | Trieu |
| 2009/0222093 A1 | 9/2009 | Liu et al. |
| 2009/0234457 A1 | 9/2009 | Lotz et al. |
| 2009/0270989 A1 | 10/2009 | Conner et al. |
| 2009/0270990 A1 | 10/2009 | Louis et al. |
| 2009/0275913 A1 | 11/2009 | Trieu |
| 2009/0281517 A1 | 11/2009 | Lambrecht et al. |
| 2009/0292322 A1 | 11/2009 | Lambrecht |
| 2010/0004664 A1 | 1/2010 | Boyajian et al. |
| 2010/0030333 A1 | 2/2010 | Michelson |
| 2010/0049259 A1 | 2/2010 | Lambrecht et al. |
| 2010/0057143 A1 | 3/2010 | Lambrecht et al. |
| 2010/0087926 A1 | 4/2010 | Butler et al. |
| 2010/0094425 A1 | 4/2010 | Bentley et al. |
| 2010/0114317 A1 | 5/2010 | Lambrecht et al. |
| 2010/0121455 A1 | 5/2010 | Lambrecht et al. |
| 2010/0145454 A1 | 6/2010 | Hoffman |
| 2010/0145463 A1 | 6/2010 | Michelson |
| 2010/0152784 A1 | 6/2010 | Lowry et al. |
| 2010/0152790 A1 | 6/2010 | Hestad |
| 2010/0161056 A1 | 6/2010 | Voellmicke et al. |
| 2010/0161060 A1 | 6/2010 | Schaller et al. |
| 2010/0185285 A1 | 7/2010 | Perkins |
| 2010/0185286 A1 | 7/2010 | Allard et al. |
| 2010/0191335 A1 | 7/2010 | Root et al. |
| 2010/0204797 A1 | 8/2010 | Lambrecht |
| 2010/0211108 A1 | 8/2010 | Lemole |
| 2010/0298837 A1 | 11/2010 | Gorensek |
| 2011/0022061 A1 | 1/2011 | Orphanos et al. |
| 2011/0106264 A1 | 5/2011 | Lambrecht et al. |

| 2011/0118844 A1 | 5/2011 | Lambrecht |
| 2011/0125271 A1 | 5/2011 | Lambrecht |
| 2011/0196492 A1 | 8/2011 | Lambrecht et al. |

FOREIGN PATENT DOCUMENTS

| EP | 0298235 | 1/1989 |
| EP | 0682910 | 3/1995 |
| EP | 0700671 | 3/1996 |
| EP | 0876808 | 11/1998 |
| EP | 0722700 | 12/1998 |
| EP | 1091776 | 5/2004 |
| EP | 1214026 | 4/2005 |
| EP | 1180978 | 5/2005 |
| FR | 2639823 A1 | 6/1990 |
| JP | S64-887 | 1/1989 |
| JP | H05-29694 | 7/1993 |
| JP | 1995-148172 | 6/1995 |
| JP | S63-95043 | 4/1998 |
| RU | 2020901 | 10/1994 |
| RU | 93031998 A | 11/1995 |
| RU | 2055544 | 3/1996 |
| RU | 2078551 | 5/1997 |
| RU | 96121354 A | 1/1999 |
| WO | WO 92/10982 | 9/1992 |
| WO | WO 93/22990 | 11/1993 |
| WO | WO 95/26689 | 10/1995 |
| WO | WO 95/31946 | 11/1995 |
| WO | WO 95/34331 | 12/1995 |
| WO | WO 96/01164 | 1/1996 |
| WO | WO 96/01598 | 1/1996 |
| WO | WO 97/26847 | 7/1997 |
| WO | WO 97/30638 | 8/1997 |
| WO | WO 98/17190 | 4/1998 |
| WO | WO 98/20939 | 5/1998 |
| WO | WO 98/34552 | 8/1998 |
| WO | WO 98/38918 | 9/1998 |
| WO | WO 99/00074 | 1/1999 |
| WO | WO 99/02108 | 1/1999 |
| WO | WO 99/02214 | 1/1999 |
| WO | WO 99/03422 | 1/1999 |
| WO | WO 99/30651 | 6/1999 |
| WO | WO 99/47058 | 9/1999 |
| WO | WO 99/61084 | 9/1999 |
| WO | WO 99/62439 | 12/1999 |
| WO | WO 00/14708 | 3/2000 |
| WO | WO 00/18328 | 4/2000 |
| WO | WO 00/42953 | 7/2000 |
| WO | WO 00/44288 | 8/2000 |
| WO | WO 00/45741 | 8/2000 |
| WO | WO 00/49978 | 8/2000 |
| WO | WO 00/62832 | 10/2000 |
| WO | WO 00/71043 | 11/2000 |
| WO | WO 01/10316 | 2/2001 |
| WO | WO 01/12080 | 2/2001 |
| WO | WO 01/12107 | 2/2001 |
| WO | WO 01/21246 | 3/2001 |
| WO | WO 01/28464 | 4/2001 |
| WO | WO 01/28468 | 4/2001 |
| WO | WO 01/39696 | 6/2001 |
| WO | WO 01/45577 | 6/2001 |
| WO | WO 01/45579 | 6/2001 |
| WO | WO 01/52914 | 7/2001 |
| WO | WO 01/78616 | 10/2001 |
| WO | WO 02/051622 | 7/2002 |
| WO | WO 02/058599 | 8/2002 |
| WO | WO 02/067824 | 9/2002 |
| WO | WO 03/039328 | 5/2003 |
| WO | WO 03/088876 | 10/2003 |
| WO | WO 2004/080355 | 9/2004 |
| WO | WO 2005/027800 | 3/2005 |

OTHER PUBLICATIONS

Bagga C.S., Williams P., Highma P.A., Bao B.Q., "Development of Fatigue Test Model for a Spinal Nucleus Prosthesis with Preliminary Results for a Hydrogel Spinal Prosthetic Nucleus," Proceedings of the 1997 Bioengineering Conference, 441-442: BED-vol. 35, Sunriver, Oregon, Jun. 11-15, 1997.

Balderston, R.A., et al., "The Treatment of Lumbar Disc Herniation: Simple Fragment Excision Versus Disc Space Curettage," *J. of Spinal Disorders*, 4 (1) : 22-25 (1991).

Bao Q.B., Bagga C.S., "The Dynamic Mechanical Analysis of Hydrogel Elastomers," Thermochimica Acta, 226:107-113 (1993).

Bao Q.B., McCullen G.M., Higham P.A., Dumbleton J.H., Yuan H.A., "The Artificial Disc: Theory, Design and Materials," Biomaterials, vol. 17, No. 12:1157-1167 (1996).

Bao Q.B., Yuan H.A., "Artificial Disc Technology," Neurosurg Focus 9(4), 2000.

Barr, J.S., "Ruptured Intervertebral Disc and Sciatic Pain," *J. of Bone and Joint Surgery*, 29, (2) : 429-437 (1947).

Brinckmann, P., et al., "Change of Disc Height, Radial Disc Bulge, and Intradiscal Pressure From Discectomy an in Vitro Investigation on Human Lumbar Discs," *Spine*, 16 (6) : 641-646 (1991).

Cauthen, Joseph, Draft Abstract entitled *Microsurgical Annular Reconstruction (Annuloplasty) Following Lumbar Microdiscectomy: Preliminary Report of a New Technique*, from abstracts@neurosurgery.org, reportedly published in Feb. 1999 and dated Sep. 4, 1998, and contextual documents, 39 pages.

Goel, V. K., et al., "Mechanical Properties of Lumbar Spinal Motion Segments as Affected by Partial Disc Removal," Spine, 11 (10) : 1008-1012 (1986).

Hanley, E.N., Jr., et al., "The Development of Low-Back Pain After Excision of a Lumbar Disc," *J. of Bone and Joint Surgery*, 71A (5) : 719-721 (1989).

Hedman T.P., Kostuik J.P., Fernie G.R., Hellier W.G., "Design of an Intervertebral Disc Prosthesis," Spine 16 (Suppl. 6):S256-S260 (1991).

Heggeness, M.H., et al., "Discography of Lumbar Discs After Surgical Treatment for Disc Herniation," *Spine*, 22 (14) : 1606-1609 (1997).

Husson J.L., Baumgartner W., Le Huec J.C., "Nucléoplastie Inter-Somatique Par Voie Postérieure Per-Dissectomie: Concept et Étude Expérimentale," Restabilisation Inter-Somatique Due Rachis Lombaire:311-320 (1996).

Husson J.L., Scharer N., Le Nihouannen J.C., Freudiger S., Baumgartner W., Polard J.L., "Nucleoplasty During Discectomy Concept and Experimental Study," Rachis vol. 9, No. 3:145-152 (1997).

Kayama, S., et al., "Incision of the Anulus Fibrosus Induces Nerve Root Morphologic, Vascular, and Functional Changes," *Spine*, 21 (22) : 2539-2543 (1996).

Khelimsky et al. "Plastic Surgery of Damaged Intervertebral Discs with Fast-Solidifying Glue Composition (Experimental Research)." Collected articles Experimental Traumatic Surgery and Orthopaedics Moscow, 1990, pp. 88-90.

Langrana N.A., Parsons J.R., Lee C.K., Vuono-Hawkins M., Yang S.W., Alexander H., "Materials and Design Concepts for an Intervertebral Disc Spacer. I. Fiber-Reinforced Composite Design," Journal of Applied Biomaterials, vol. 4:125-132 (1994).

Lemaire J.P., Skalli W., Lavaste F., Templier A., Mendes, F., Diop A., Sauty V., Laloux E., "Intervertebral Disc Prosthesis," Clinical Orthopaedics and Related Research, No. 337:64-76 (1997).

Martz E.O., Goel V.K., Pope M.H., Park J.B., "Materials and Design of Spinal Implants—A Review," Journal of Biomedical Materials Research, vol. 38, Issue 3:267-288 (1997).

Postacchini, F., "Spine Update results of Surgery Compared With Conservative Management for Lumbar Disc Herniations," *Spine*, 21 (11) : 1383-1387 (1996).

Ray C.D., Schonmayr R., Kavanagh S.A., Assell R., "Prosthetic Disc Nucleus Implants," Riv. Neuroradiol 1999:12 (Suppl. 1):157-162.

Rogers, L.A., "Experience with Limited versus Extensive Disc Removal in Patients Undergoing Microsurgical Operations for Ruptured Lumbar Discs," *Neurosurgery*, 22 (1) : 82-85 (1988).

Sakalkale D.P., Bhagia S.A., Slipman C.W., "A Historical Review and Current Perspective on the Intervertebral Disc Prosthesis," Pain Physician, vol. 6, No. 2:1-4 (2003).

Schonmayr R., Busch C., Lotz C., Lotz-Metz G., "Prosthetic Disc Nucleus Implants: The Wiesbaden Feasibility Study, 2 Years follow-up in Ten patients," Riv. Neuroradiol 1999:12 (Suppl. 1):163-170.

Sheljakin S. Ju. "Percutaneous Diskectomy Skin-through Discectomy in Complex Treatment of Patients with Disc Lumbosacral Polyraduculitis." Abstract of a thesis, St. Petersburg, 1996.

Shul'man Kh.M. "Pathogenetic Therapy of Compression Type Osteochondritis of Spinal Lumbar Region." Collected articles Reconstruction-and-Restoration Treatment in Traumatic Surgery, Orthopaedics, Surgery and Neurosurgery, Kazan', 1976, pp. 17-21.

Shul'man Kh.M. "Surgical Treatment of Compression Type Osteochondritis of Spinal Lumbar Region with Intervertebral Disc Implantation." Kazan', 1980, pp. 174-185.

Shul'man Kh.M., Danilov V.I. "Biochemical Experimental Basis of Intervertebral Disc Prosthesis Implantation Method by Fast-solidifying Polyurethane CKYu-PFL in Case of Disc Degeneration or Traumatic Damage." Collected articles Reconstruction-and-Restoration Treatment in Traumatic Surgery, Orthopaedics, Surgery and Neurosurgery. Kazan', 1976, pp. 22-27.

Tibrewal, S.B., et al., "Lumbar Intervertebral Disc Heights in Normal Subjects and Patients with Disc Herniation," *Spine*, 10 (5) : 452-454 (1985).

Tullberg, T., et al., "Radiographic Changes After Lumbar Discectomy," *Spine*, 18 (7): 843-850 (1993).

Usmanov M.M. "Intervertebral Disc Changes at Local Damage of its Elements and Implantation of Various Materials." Abstract of a thesis Moscow, 1991.

USSR Authors Certificate No. 1477390 "Method for Treatment of Osteochondritis." Published May 17, 1989.

USSR Authors Certificate No. 1827204 "Method for Treatment of Spinal Osteochondritis." Published May 15, 1993.

Yasargil, M.G., Microsurgical Operation of Herniated Lumbar Disc, Adv. Neurosurg 1977;4:81.

Zelentsov E.V. "Plastic Surgery with Collagen of Intervertebral Discs for Surgical Treatment of Lumbosacral Polyradiculitis." Abstract of a thesis, Leningrad, 1990.

Zelentsov E.V. et al. "Application of Collagen for Experimental Plastic Surgery of Intervertebral Discs." Collected articles Integrated Treating of Pain Syndromes of Neurogenic Origin, Leningrad 1984 pp. 86-90.

* cited by examiner

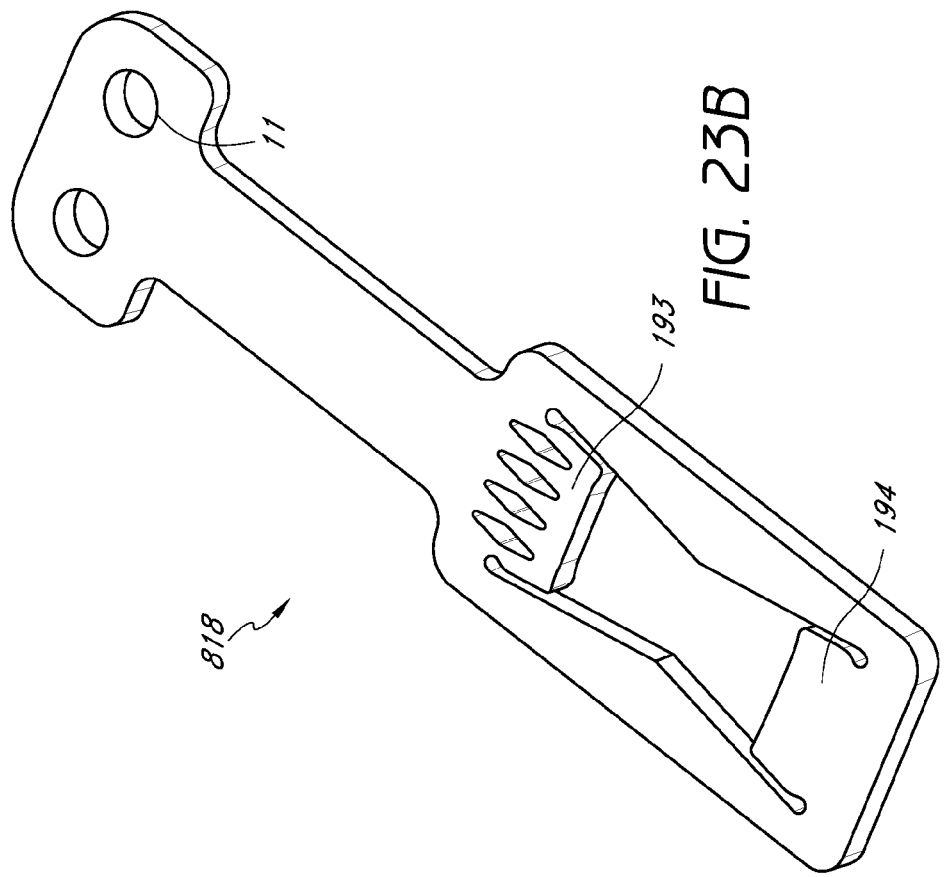
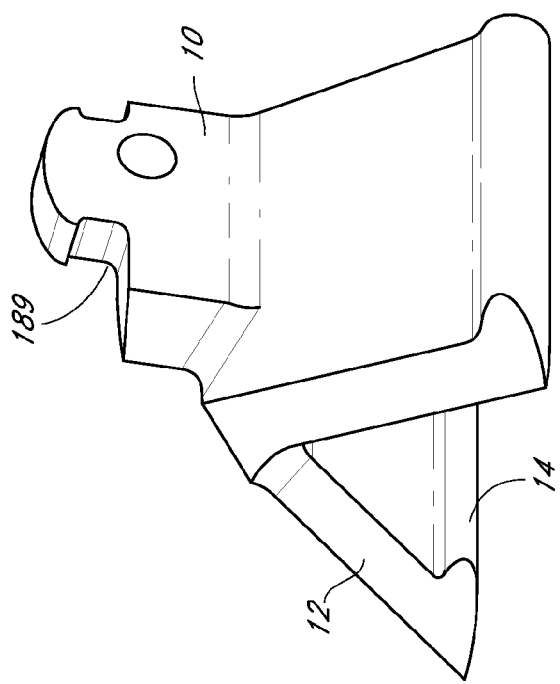

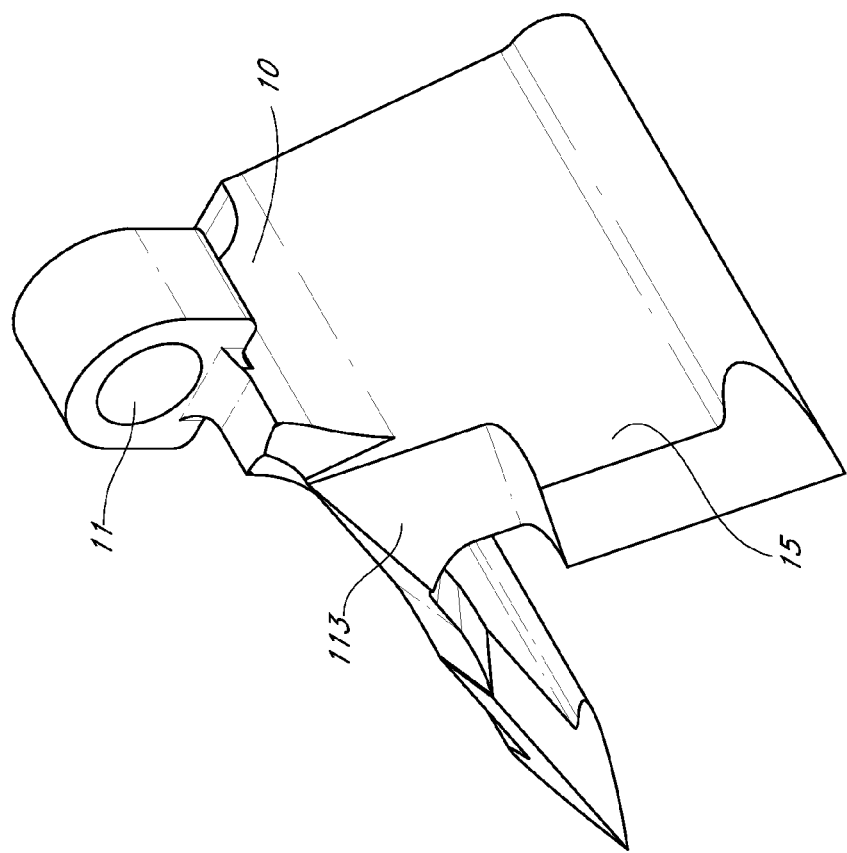
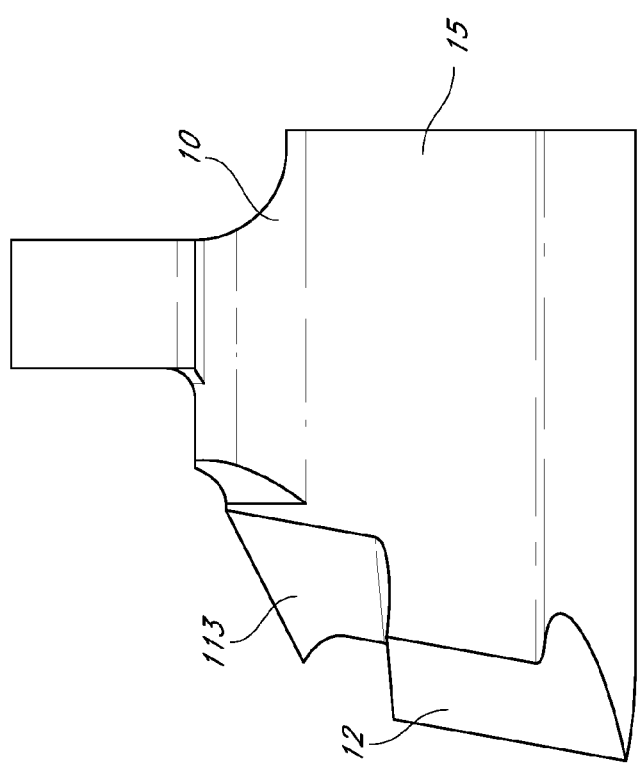
FIG. 26B
FIG. 26A

VERTEBRAL ANCHORING METHODS

CROSS-REFERENCE TO RELATED APPLICATIONS

This application is a continuation of U.S. application Ser. No. 11/641,253, filed Dec. 19, 2006, which claims the benefit of U.S. Provisional Application No. 60/754,237, filed Dec. 28, 2005, the entire teachings of each of which are incorporated in their entirety into this disclosure by reference.

BACKGROUND OF THE INVENTION

1. Field of the Invention

The invention relates generally to tissue anchors, delivery methods, and associated treatments. Anchors according to one or more embodiments of the invention can provide superior pull-out resistance, stability and may, in some embodiments, maximize contact with tissue involving a minimum amount of penetration. Delivery methods include linear, lateral, and off-angle implantation or driving of anchors along, against or within tissue surfaces.

2. Description of the Related Art

Anchors described herein can be used throughout the human body and have general applicability to fastener art. Such anchors can be used to join or anchor like or disparate materials or tissues together, maintain alignment of materials, reinforce a fracture within a material, and provide an attachment site along or within a materials surface. Generally the art includes both staples and screws. For example, U.S. Pat. No. 7,131,973 to Hoffman discloses an anchor and delivery system for treating urinary incontinence. The distal portion of the delivery tool is curved and hooked such that pulling on the instruments handle effects a retrograde delivery of the anchor. U.S. Pat. No. 5,366,479 to McGarry et al. discloses a staple and delivery system. The staple is flat but contains a pair of inwardly curving prongs. U.S. Pat. No. 5,391,170 to McGuire et al. discloses an angled screw driver for inserting bone screws in ligament tunnels as part of a ligament reconstruction procedure. U.S. Pat. No. 5,217,462 to Asnis et al. discloses a screw and driver combination having threaded shank and sleeve that cooperate to hold and release the screw. U.S. Pat. No. 5,002,550 to Li discloses a suture anchor with barbs and an installation tool that includes a curved needle for attaching a suture.

SUMMARY OF THE INVENTION

As described above, tissue anchors exist in the prior art. However, there remains a need for an anchor that can be delivered laterally, provide pull-out resistance, provide stability, and/or maximize contact with tissue involving a minimum amount of penetration. Embodiments of the invention relate generally to tissue anchors and methods of delivering tissue anchors to the intervertebral disc or other sites within the body. In one embodiment, an anchor delivery system is provided. The anchor delivery system can be pre-loaded with an anchor or the anchor can be provided separately. In one embodiment, the invention comprises one or more anchors. In another embodiment, the invention comprises a delivery tool. In yet another embodiment, the invention comprises a delivery system. The delivery system may comprise the delivery tool with or without an anchor.

In one embodiment, the anchor delivery system comprises an anchor and a hollow elongate guide body adapted to retain the anchor. The guide body comprises a proximal end and a distal end and comprises a curved passage or slot terminating in a lateral opening at the distal end. The curved passage or slot is adapted to retain the anchor. A push rod is slidably mounted within the guide body and is operable to contact the anchor in the curved passage or slot via linear advancement of said push rod to laterally drive out the anchor.

The anchor, alone or in combination with the anchor delivery system, according to one embodiment, comprises a bridge having a horizontal and vertical axis. The bridge terminates or substantially ends in at least a first prong and a second prong. The first prong and second prong extend at an angle from the bridge and are curved. The first prong and second prong are parallel along at least a portion of the first prong and the second prong. The first prong and second prong are perpendicular to the horizontal axis of the bridge. In some embodiments, the first and/or second prong comprise distal tips beveled on one or more surfaces. The two prongs can be dimensioned identically or variably. In one embodiment, the beveled tip is sharpened for advancement into bone so that a pilot hole need not be drilled.

In some embodiments, the anchor delivery system comprises an alignment means for aligning the lateral opening with a tissue surface. In other embodiments, the anchor delivery system comprises an engagement means to engage tissue. In yet other embodiments, the anchor delivery system comprises teeth, spikes, barbs, protrusions, friction plates, or combinations thereof.

In alternative embodiments, the anchor delivery system comprises a biologically active or therapeutic agent. A portion of the anchor or delivery tool may be impregnated or coated with a biologically active or therapeutic agent in some embodiments.

In several embodiments, the anchor delivery system comprises a prosthetic device. In other embodiments, the anchor is coupled to a prosthetic device.

In one embodiment, the anchor delivery system or the anchor is operable to be coupled to an intervertebral disc anulus or nucleus augmentation device, or both.

In one embodiment, the anchor delivery device comprises a guide body having a length in the range of about 5 cm to about 50 cm, preferably 10 cm to about 30 cm and a width in the range of between about 0.1 cm to about 5 cm, preferably 0.5 cm to about 1.5 cm.

In one embodiment, the push rod has a length in the range of about 5 cm to about 70 cm, preferably about 15 cm to about 40 cm and a width in the range of between about 0.01 cm to about 5 cm, preferably about 0.1 cm to about 1 cm.

In one embodiment, the first prong and the second prongs have heights in the range of about 0.1 cm to about 10 cm, preferably about 0.2 cm to about 5 cm. Widths in the range of between about 0.01 cm to about 2 cm, preferably about 0.05 cm to about 0.5 cm, are provided. In several embodiments, a third, forth, or fifth prong is provided. In some embodiments, more than five prongs can be used. Prongs can be of identical height and width or have dimensions different from one another. In one embodiment, a fork-like device is provided, with each tine have a different height. In other embodiments, at least two of the tines have different widths or heights. In other embodiments, the prongs are dimensioned identically. In alternative embodiments, prongs or tines may have different flexibilities. A single prong or tine may be variably flexibly along its length. Variation in tine or prong dimensions or rigidity may be well-suited to certain environments that have variable tissue types, depths, strength, fragility, or flexibility.

In one embodiment, the bridge has a length of about 0.01 cm to about 10 cm along its horizontal axis, preferably 0.1 cm to about 5 cm.

In several embodiments, the anchor is at least partially constructed from a material selected from the group consisting of one or more of the following: nickel titanium alloy, titanium, cobalt chrome alloys, steel, or combinations thereof.

In several embodiments, methods of delivering an anchor according to any of the embodiments described herein are provided. In other embodiments, the invention comprises a minimally invasive method of treating a mammal with an anchored prosthetic.

In one embodiment, a method of delivering an anchor along the surface of a tissue is provided. In one embodiment, the method comprises providing a delivery device comprising an elongate guide body having a proximal and distal end and a push rod slidably mounted within the guide body. The guide body has a curved passage or slot terminating in a lateral opening at the distal end of the guide body. A curved anchor is inserted into the curved passage or slot. A distal end of the guide body is inserted along the tissue surface. The push rod is pushed to laterally expel the curved anchor into the tissue surface along a curvilinear trajectory. The curvilinear trajectory comprises an angle in a range between about 45 degrees to about 135, preferably about 75 degrees to about 100 degree, relative to the tissue surface.

In one embodiment, the tissue surface comprises bone, such as a vertebral endplate.

In one embodiment, the step of inserting a distal end of the guide body along the tissue surface comprises distracting opposing vertebral bodies.

In another embodiment, the method further comprises providing a depth stop on the guide body operable to limit the depth traveled by the distal tip and aligning the depth stop against an outer surface of the tissue.

In another embodiment, a method of providing an anchor within a surface is provided. The method comprises identifying a first surface adjacent to second surface wherein the surfaces are offset relative to each other and form an intersection defining a corner or angle. An anchor with an elongated plate-like keel portion having a length defined by a leading edge and trailing end and having a height defined by a lower edge of the keel is provided. The anchor also has a neck extending from the upper surface of the keel where the neck further comprises an attachment site. The anchor is positioned relative to the intersection such that at least a portion of the attachment site of the anchor is flush or beyond the intersection and at least a portion of the leading edge is adjacent the first surface. The leading edge is driven into the first surface while simultaneously advancing the attachment portion across the second surface.

In one embodiment, the method further comprises providing a bifurcated keel forming an apex at the intersection with the neck. In another embodiment, the method further comprises advancing the anchor beyond the surface of the first surface thereby countersinking it. In yet another embodiment, the method further comprises positioning at least a portion the neck above the intersection.

In one embodiment, the method further comprises identifying two surfaces that are substantially perpendicular. The first surface can be the exterior of a vertebral body and the second surface can be the corresponding adjacent vertebral endplate.

In one embodiment, an anchor comprising an elongated plate-like keel portion having a length defined by a leading edge and trailing end and having a height defined by a lower edge of the keel is provided. The anchor may comprise a neck extending from an upper surface of the keel. The neck may comprise one or more attachment sites.

In another embodiment, the invention comprises an anchor comprising a neck terminating in one or more plate-like keel portions having a length defined by a leading edge and trailing end and having a height defined by a lower edge of the keel and a top portion of the neck. The neck may comprise one or more attachment sites.

In yet another embodiment, the cross-section of the anchor is shaped like an "upside-down Y." The anchor comprises a neck terminating in two or more plate-shaped or plate-like keel portions having a length defined by a distance separating a sharpened leading edge and trailing end and having a height defined by a lower edge of the keel and a top portion of the neck. The keels form an angle between about 5 degrees to about 360 degrees, preferably about 10 degrees to about 180 degrees, more preferably about 90 degrees at the termination of the neck. The neck comprises an attachment site and extends along at least a portion of the length of the keel. In some embodiments, the plate shaped keel portion appears as an ovoid or substantially circular shape. In some embodiments, the keel portion comprises a wire frame or mesh.

Although one anchor is provided in some embodiments, two, three, four or more anchors are used in alternative embodiments.

BRIEF DESCRIPTION OF THE DRAWINGS

FIG. 22A shows a perspective view of another embodiment of an anchor according to one or more embodiments of the invention having a three legged keel portion and designed such that only the attachment portion remains proud on the tissue surface. FIG. 22B shows a delivery tool for driving an anchor with a mated surface and alignment pins.

FIGS. 23A-B show a perspective view of another embodiment of an anchor according to one or more embodiments of the invention having a flexible linkage member.

FIGS. 26A-B show a side view and perspective view of an anchor with a sharpened leading edge having a recessed region corresponding to the cupped cortical rim of a vertebral endplate.

DETAILED DESCRIPTION OF THE PREFERRED EMBODIMENT

Embodiments of the invention relate generally to tissue anchors and methods of delivering tissue anchors to the intervertebral disc or other sites within the body. In some embodiments, the tissue anchors provide pull-out resistance, stability and/or maximize contact with tissue involving a minimum amount of penetration. In some embodiments, delivery methods are minimally invasive and include, but are not limited to, linear, lateral, and off-angle implantation or driving of anchors along, against or within tissue surfaces. In several preferred embodiments, bone anchors are provided.

The term "anchor" as used herein shall be given its ordinary meaning and shall also include, but not be limited to, nails, staples, screws, fasteners, sutures, spikes, tacks, keys, pegs, rivets, spikes, bolts, and pins. In several embodiments, the anchor comprises one or more tines or prongs. In one embodiment, the anchor is forked. In some embodiments, the anchor may be straight, curved, or partially curved.

In several embodiments, the anchors disclosed herein are particularly suited for hard tissues such as bone. In other embodiments, soft tissue anchors are provided. One or more embodiments of the anchor can be delivered into a tissue and be secured within said tissue and resist extraction, migration, and/or rotation. Such stability is especially important in environments like the spine, where the anchor is adjacent delicate nerve tissue such as the spinal cord. However, in several embodiments, the anchoring system may be used in other delicate vasculature such as the aorta.

Although several examples of sites appropriate for anchors are described herein for use in the boney tissue of the spine and particularly the vertebral endplates, anchors according to the embodiments described herein have broad applications. For example, the anchors described herein may be used in the radial head, ulnar head, humeral head, tibial plateau, scapula, acromion, talus, malleolus; tendons and ligaments such as the talo-fibular ligament, anterior cruciate ligament, patella tibial tendon, Achilles tendon, rotator cuff, and other tissues such as the meniscus. Further, anchors according to one or more embodiments of the invention can disposed within artificial tissues or prosthetics.

Figure 1A:
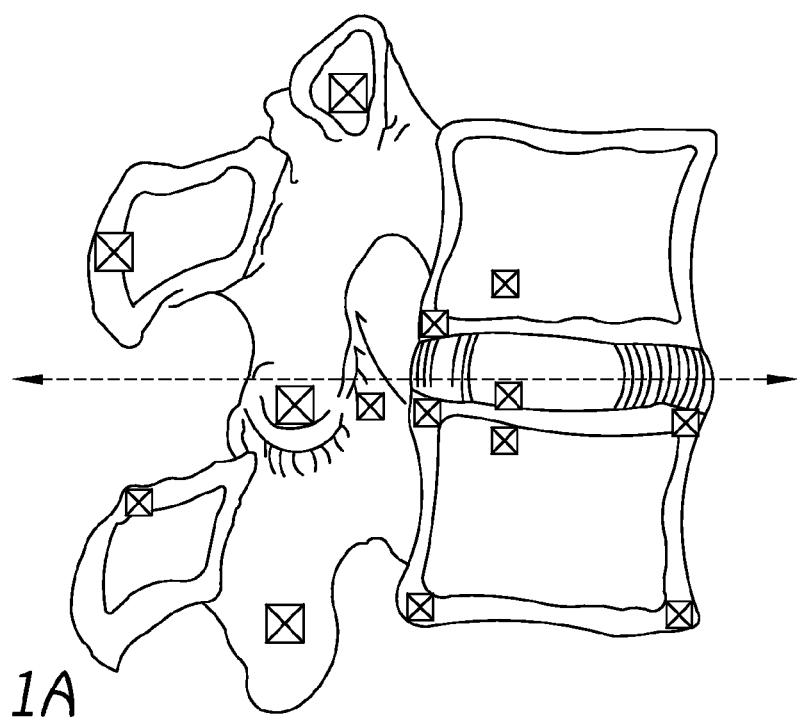
FIGS. 1A-B show an axial and sagittal view of a spine segment and various anchor sites.
Figure 1B:
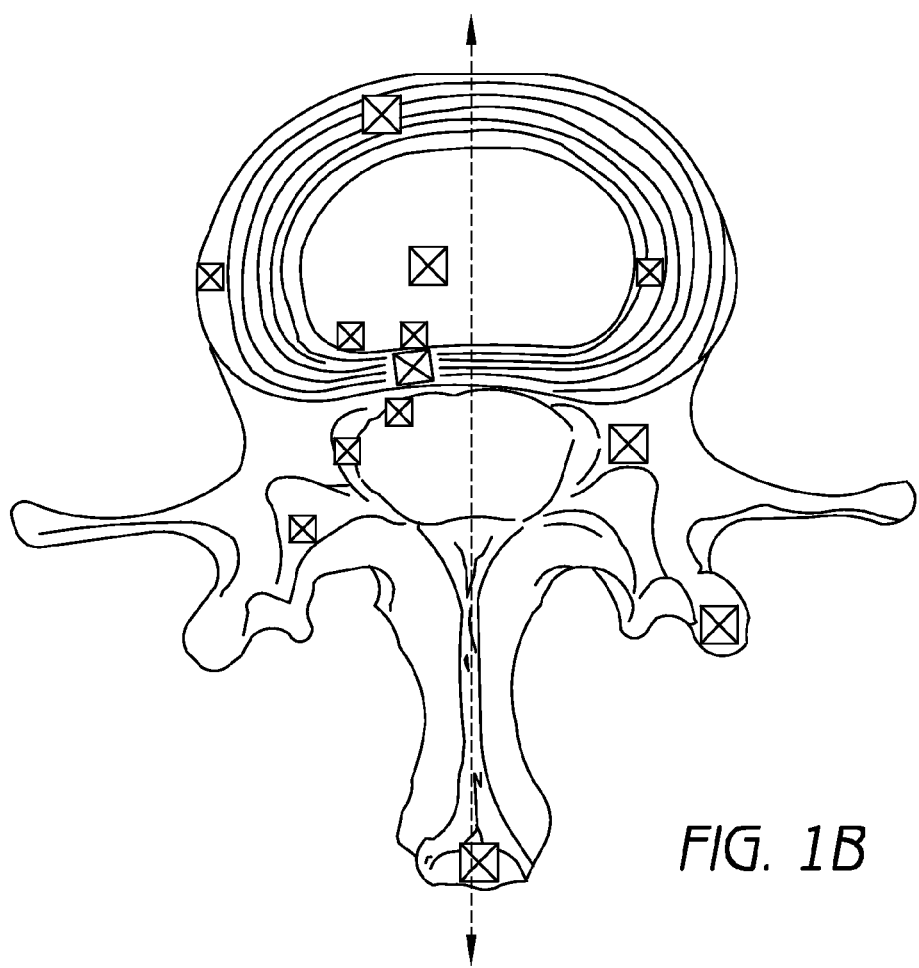

FIG. 1A provides a sagittal view of a spine segment. Also shown are numerous potential anchor sites and are marked as "X." FIG. 1B is an axial view of the same spine segment and shows other possible anchoring sites including along or within a vertebral body, endplate, transverse process, spinous process, facet, and pedicle. In other embodiments, an anchor can be placed along the cortical rim of the endplate or medially within the cancellous bone or relative to or within a pedicle, skull, or sacrum. Other anchoring sites include, but are not limited to: relative to a defect within the disc either in the area of the defect, at the interface of the anulus and nucleus or in the area of the nucleus.

In several embodiments, one or more anchors are used in connection with an anulus or nucleus augmentative device, as described in U.S. Pat. Nos. 6,425,919; 6,482,235; 6,508,839; and 6,821,276, all herein incorporated by reference. In one embodiment, one or more anchors are used to anchor an anulus augmentation device that is placed within or beyond a defect in the anulus to the vertebral endplates.

One or more embodiments of the invention comprise anchors made at least partially of one or more of the following materials: any biocompatible material, material of synthetic or natural origin, and material of a resorbable or non-resorbable nature. The anchor may also be partially or wholly constructed from material including, but not limited to, autograft, allograft or xenograft; tissue materials including soft tissues, connective tissues, demineralized bone matrix and combinations thereof; resorbable materials including polylactide, polyglycolide, tyrosine derived polycarbonate, polyanhydride, polyorthoester, polyphosphazene, calcium phosphate, hydroxyapatite, bioactive glass, collagen, albumin, fibrinogen and combinations thereof; and non-resorbable materials including polyethylene, polyester, polyvinyl alcohol, polyacrylonitrile, polyamide, polytetrafluorethylene, polyparaphenylene terephthalamide, cellulose, and combinations thereof. Further examples of non-resorbable materials include carbon-reinforced polymer composites, shape memory alloys, titanium, titanium alloys, cobalt chrome alloys, stainless steel, and combinations thereof. In some embodiments, the anchor comprises titanium alloys or cobalt chrome.

In several embodiments, the anchor comprises an anchor body and an anchor attachment site. In one embodiment, the anchor attachment site is adapted to accept or connect to a suture, linkage element, threaded screw, or provide a surface for ingrowth into an adjacent structure. The anchor attachment site can be integral to the anchor or a separate structure comprised of the same or different material as the anchor body. The anchor attachment site can be coupled to the anchor body. For example, the anchor attachment site can be flexibly, rigidly, or rotationally connected to the anchor body.

The anchor attachment site can comprise one or more of the following structures: head, flange, plate, disc, protrusion, channel, hole, cleat or eye. These structures can be placed at various positions along the anchor. For example, one or more of these structures may be placed at or near the ends of the anchor, in the middle of the anchor, or at any other desired position. In some embodiments, the anchor attachment site comprises mesh, fabric, or membrane material, or a combination thereof. The site may be parallel, perpendicular or angled with respect to the body of the anchor. In one embodiment, the anchor attachment site is located on an end or terminus of the anchor body.

In one embodiment, the anchor comprises one anchor body and one anchor attachment site. In another body, the anchor comprises one or more anchor bodies and one or more anchor attachment sites. In one embodiment, the anchor comprises one body and two attachment sites.

In one embodiment, at least a portion of the anchor comprises a biologically active or therapeutic agent. For example, in some embodiments, at least a portion of the anchor can comprise growth factors such as bone morphogenic proteins, insulin-like growth factor 1, platelet derived growth factor, and fibroblast growth factor. In one embodiment, both the anchor body and anchor attachment portion of the anchor can be adapted to deliver a biologically active or therapeutic agent. In other embodiments, at least a portion of the anchor is coated with a biologically active or therapeutic agent.

Curvilinear Anchor

Anchors (including staples, nails, and other fastening or joining devices) according to one or more embodiments of the invention can be partially or wholly arcuate or curvilinear. The radius of curvature (the tightness or gentleness of the curve) can vary among embodiments as can the section of a circle corresponding to the anchor. For example, an anchor having a 90 degree curve would appear as ¼ of a circle. Other ranges of curves between 0-180 degrees are also possible. In some embodiments, for example, the curvature is about 15, 30, 45, 60, 75, 90, 120, 150, or 180 degrees.

An anchor can also be at least partially curved with a linear portion extending upward. In this embodiment the curved portion is adapted for driving into a tissue and the straight portion remains proud, or above the surface. Depending upon how the anchor is driven into the surface, the proud portion of the anchor can be anywhere from 0-180 degrees relative to the surface. The curvature of an embodiment of the anchor can also be variable along the anchor. Such a variable curvature could be employed to increase or decrease pressure on tissues adjacent to the anchor. In one embodiment, the proud portion is about 15, 30, 45, 60, 75, 90, 120, 150, or 180 degrees relative to the surface.

The surface or body of the anchor can be roughened, porous, barbed, lubricated, coated or impregnated with a biologically active or therapeutic agent. The anchor can be in the form of a curved nail or staple with a crown or bridge and having two or more prongs or legs extending therefrom. A slot or gap between the prongs in one or more embodiments of a staple can be aimed at a suture or other structure already implanted in or along a surface and then hammered in place thereby anchoring the suture in place. The tips of the prongs of a staple can be beveled to effect a wedging action. By beveling or angling the inner, outer, front, and/or back of a prong tip, the prong will tend to travel in a particular direction. Moreover, the beveled tips can complement each other, work in opposition, or some combination thereof. In one embodiment the prong tips are beveled on the outside edge, in another embodiment the tips are beveled on the inside edge. In yet another embodiment, the top of one prong is beveled and the bottom of another is beveled. In addition, the cross section of prongs may be variable along the length of the anchor. In one embodiment, the anchor prong's smallest cross section is at or near the tip and at its greatest furthest from the tip, creating a wedge along the curve of the anchor. This may aid in increasing compression on all or part of the bone or other tissue in contact with the anchor.

In another embodiment of the invention, an anchor can be resiliently flexible such that after passing through a curved slot or deflecting surface of the delivery device, the anchor (including staples, nails, etc) straightens out to its original shape as it is advanced out of the device and into the tissue. The original shape, predetermined shape, first shape, or unrestrained shape can be, for example, straight, angled, corkscrew, or offset. The prongs or legs of one or more embodiments of the anchor, such as, for example, a staple, can be straight, curved, angled, corkscrew, or offset with respect to each other.

Anchor Delivery Tool

Figure 2:
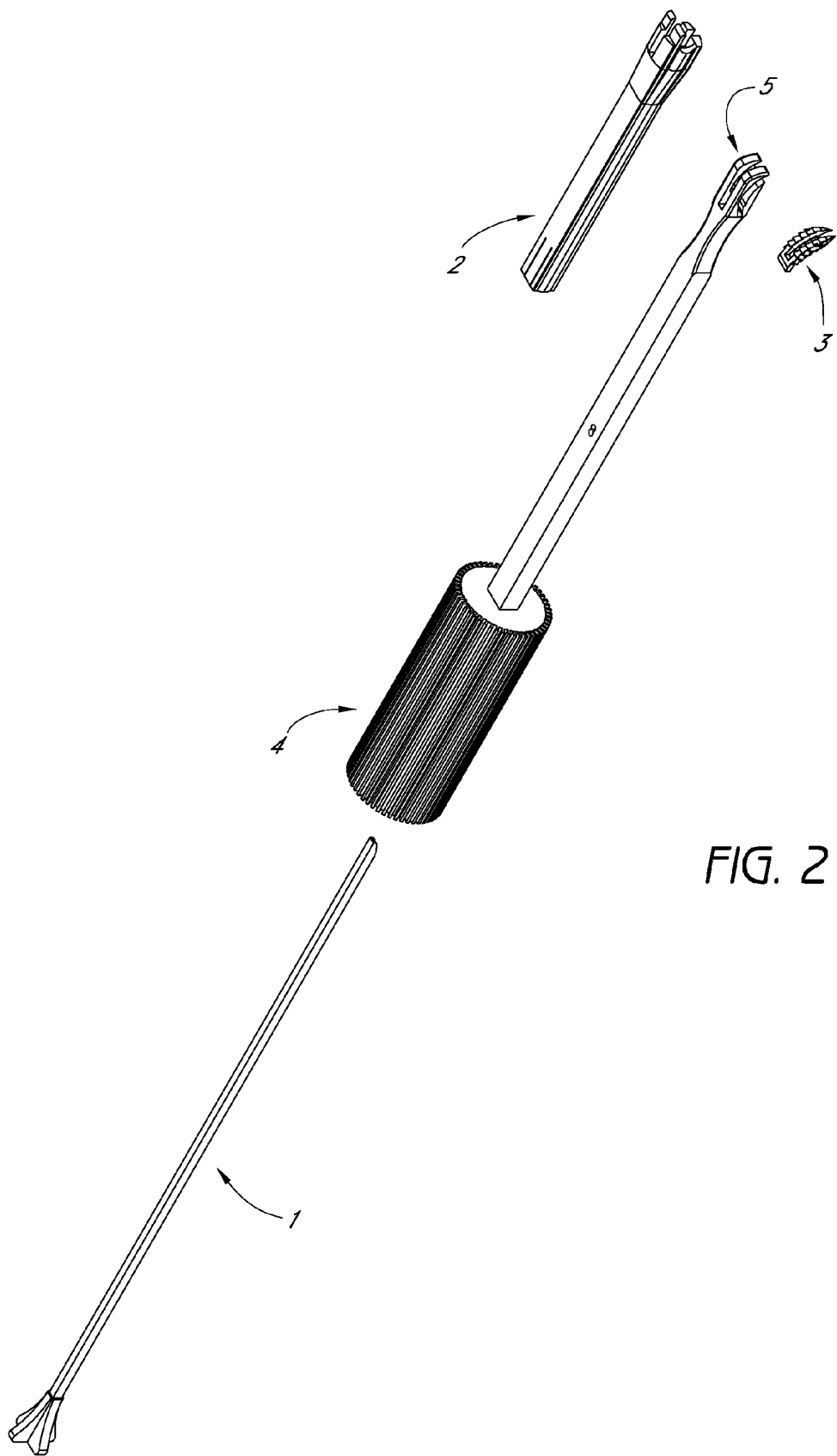
FIG. 2 shows an exploded view of one embodiment of a curvilinear anchor and delivery instrument.

Turning now to FIG. 2, shown is a preferred embodiment of an anchor and delivery instrument according to one or more aspects of the invention. A guide body 4 has a cylindrical grip or hand hold and first proximal and second distal end. The body 4 can be partially or fully hollow and contain a guide way chamber 5 for holding and orienting an anchor or staple 3 terminating in an opening at the distal end of the guide body. The opening can be oriented axially out of the front of the body or laterally and side mounted. The guide way chamber 5 comprises a curved or angled slot or passage and opens perpendicular or off angle (or between 0-180) with respect to the long axis of the guiding body. The radius of curvature along the passage can be constant or variable along the sweep of the curve. A curved nail or staple 3 can be inserted within the chamber 5 via a side loading window. A pusher rod 1 is carried within or by the body 4 and accesses or is in communication with the guide way chamber. The rod 1 has a first proximal end that can be configured with a head or striking surface for hammering and a second distal end for transmitting force to the end of a nail, staple, or anchor 3 within the guide way chamber 5. The distal end or anvil can be curved, beveled, or angled such that the linear force of the rod can be transmitted downward or along an arc as the staple 3 is driven out through the curved slot of the chamber 5. The rod 1 may be rigid or at least partially flexible in construction.

Also shown in FIG. 2 is a depth stop support 2 which can be configured as a snap on sleeve that fits over the body 4. In other embodiments a depth stop may simply be a projection off of the body that limits further travel of the body and/or guide way chamber opening within or adjacent a tissue. The depth stop may also be adjustable to allow for different implantation depths or locations. The depth stop may project in one or more directions from the long axis of the tool. Depth stops and other instrumentation described in U.S. Pat. No. 6,821,276, herein incorporated by reference, may be incorporated in several embodiments of the invention.

Figure 3:
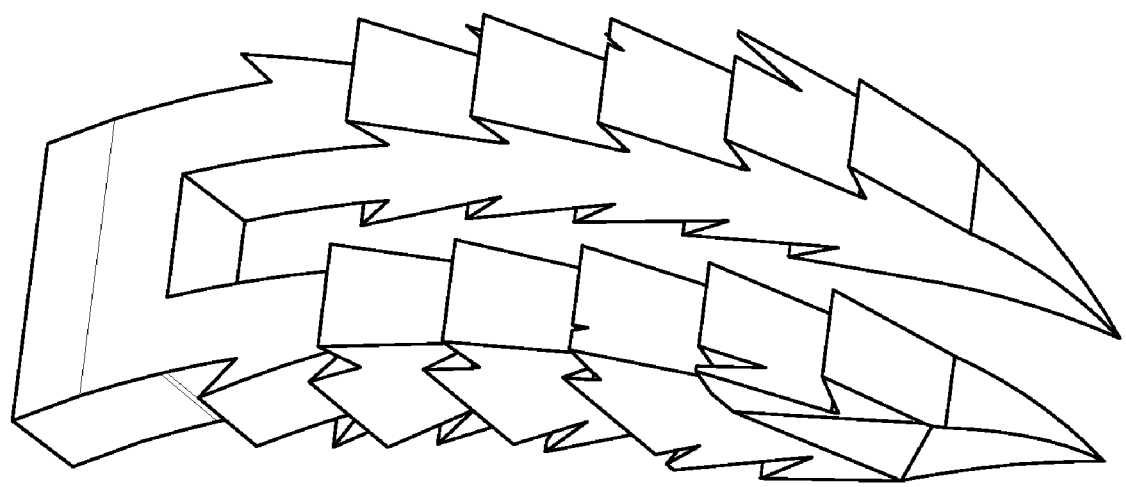
FIG. 3 shows a perspective view of one embodiment of a curved two pronged staple type anchor.
Figure 4A:
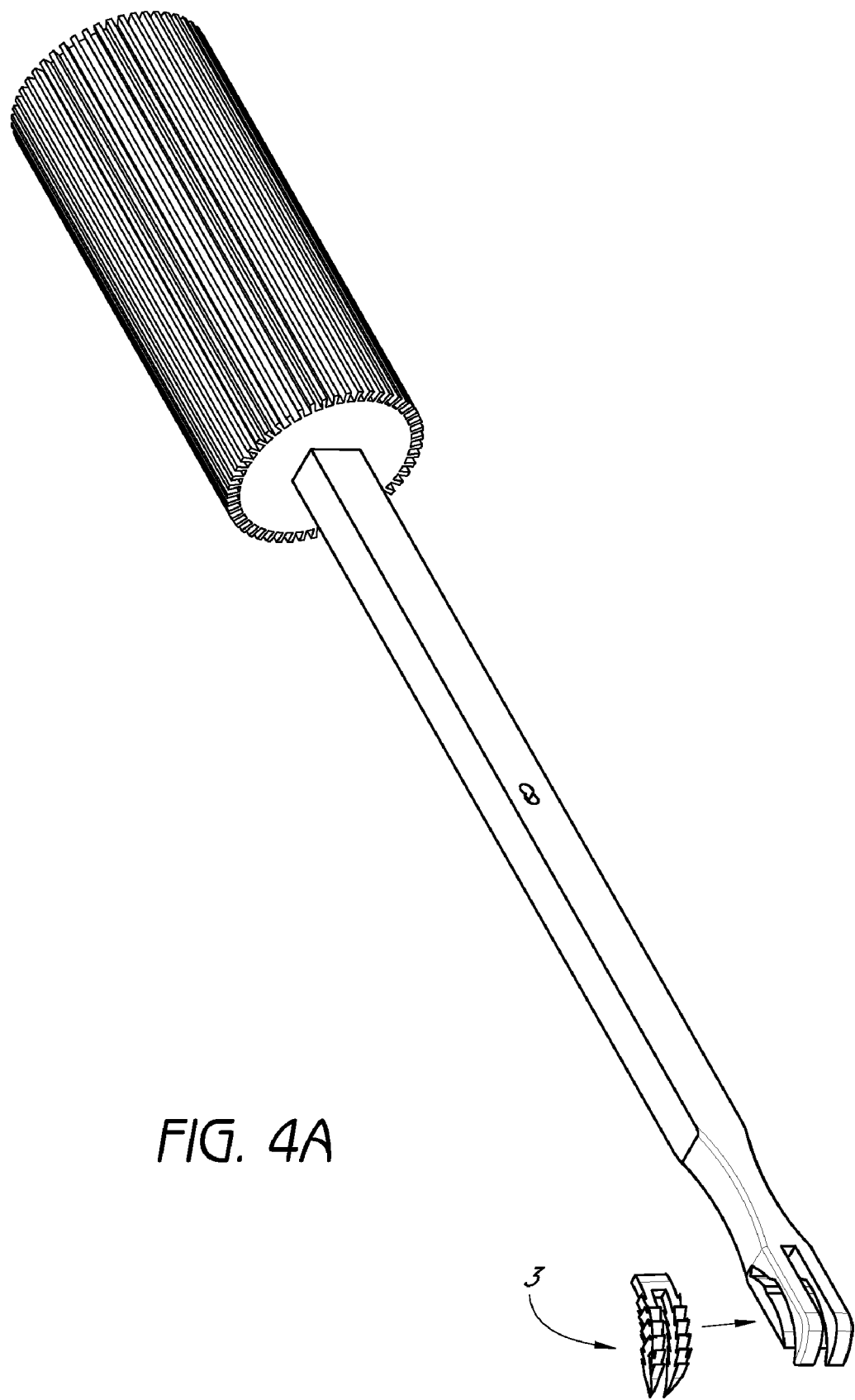
FIGS. 4A-E show a sequence involving loading an anchor into a delivery instrument and forcing it out of the lateral opening at the distal end of the delivery instrument according to one embodiment.
Figure 4B:
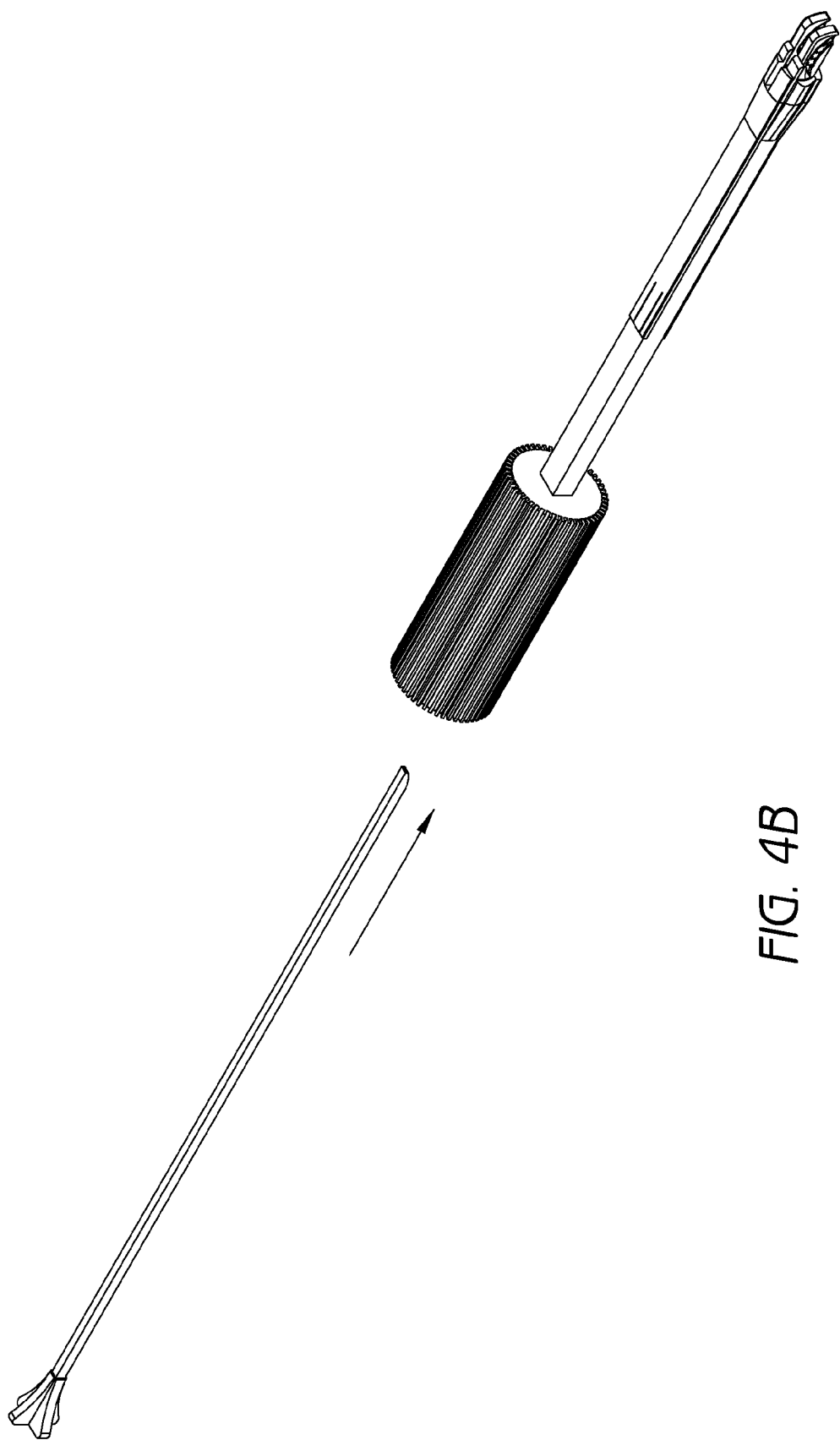
Figure 4C:
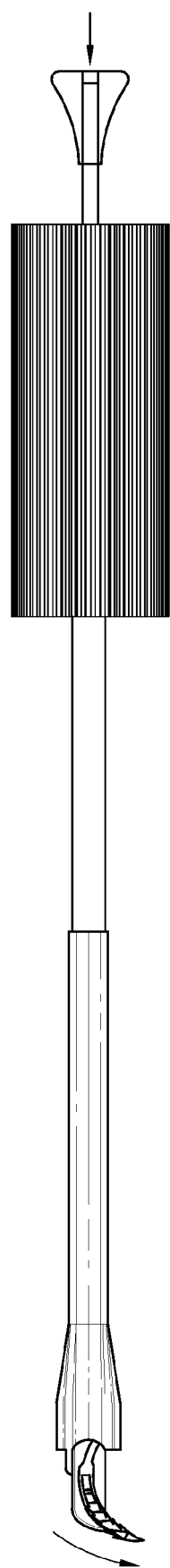
Figure 4D:
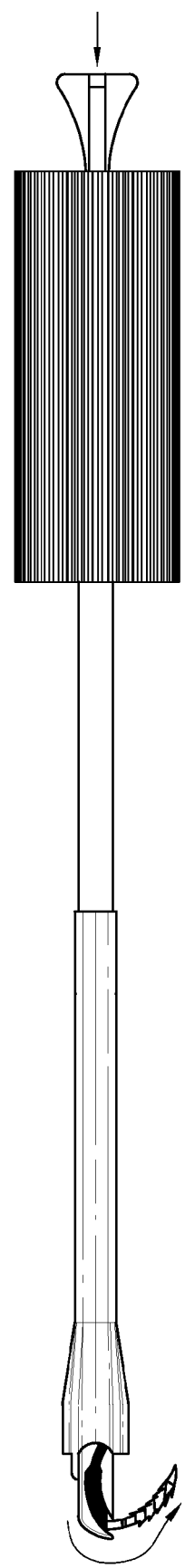
Figure 4E:
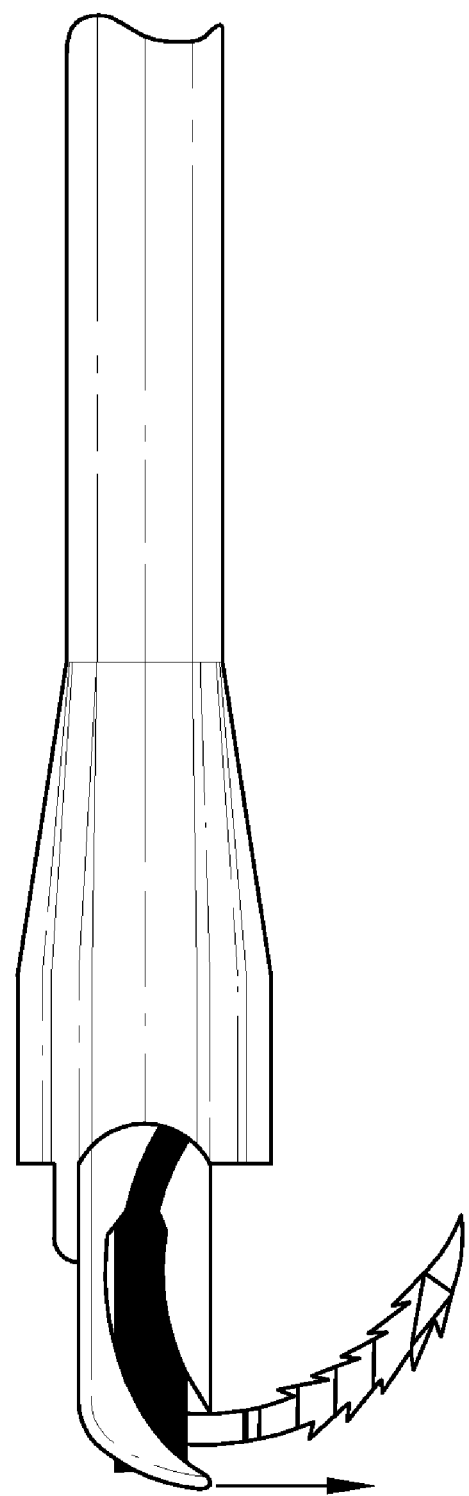

FIG. 3 is an example of an embodiment of a staple or anchor 3 with two prongs or legs that are barbed and beveled on the outside. When the staple is driven into a surface such as a bone the prongs may or may not bend inward or be wedged together. This action will pinch and compress the bone tissue between the prongs while pressing outwardly against the sidewalls of the bone facilitating a stable anchorage.

The series depicted in FIGS. 4A-E shows an embodiment of a delivery device being loaded with and anchor and the push rod applying force to the anchor and partially driving it out of the curved guide way chamber opening or lateral opening. FIG. 4 B also shows the depth stop support sleeve 2 with a vertical slot corresponding to the guiding body distal slot which is aligned with the midline of the anchor and can be used to precisely implant or drive the anchor or staple around a suture or linear structure.

Figure 5:
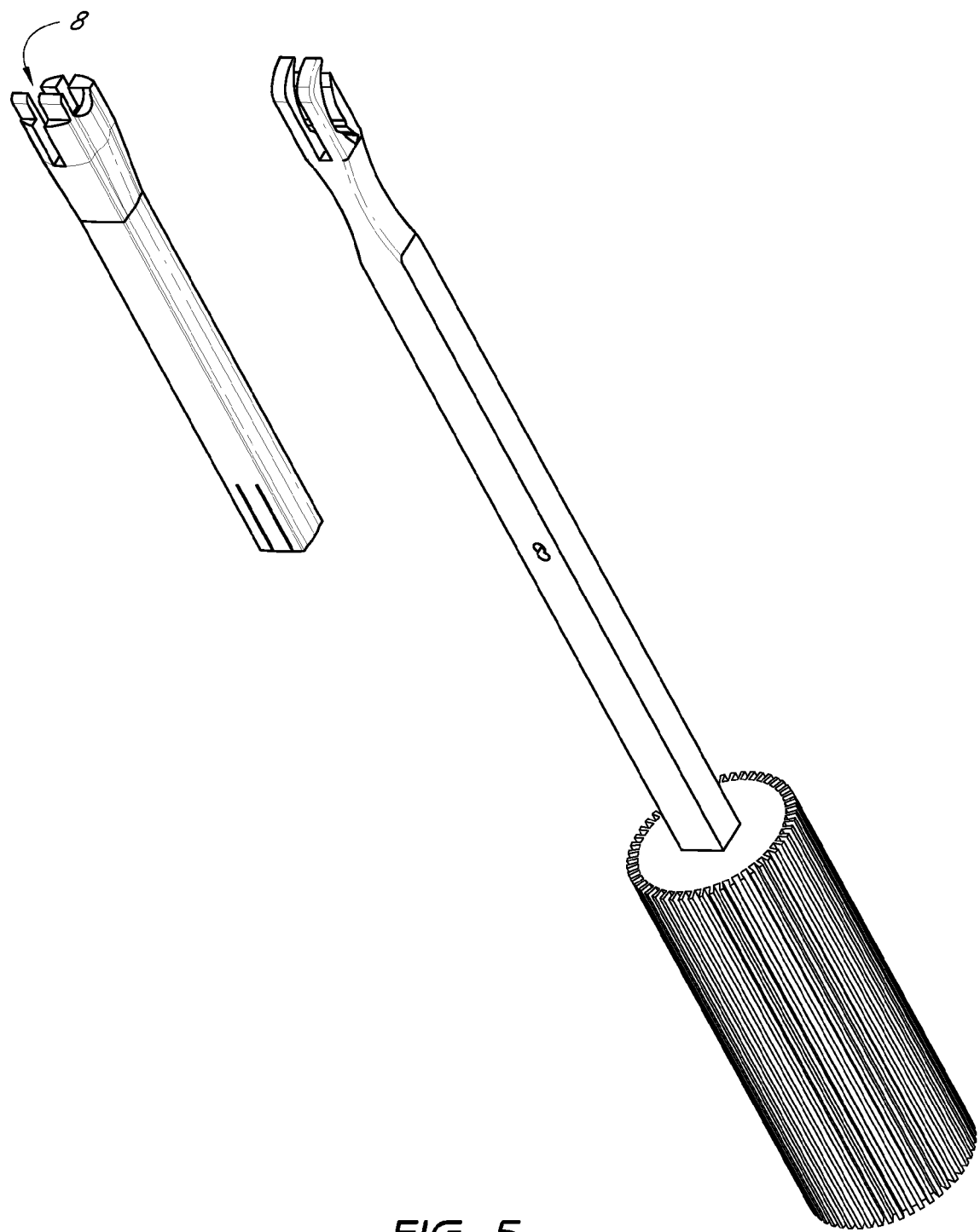
FIG. 5 shows an exploded view of one embodiment of a delivery instrument and detachable sleeve.

In FIG. 5, an embodiment of the depth stop support is shown as an attachable sleeve that fits on or over the distal end of the guiding body. However, many of the features of the sleeve can be machined, welded or attached directly to the body if so desired. In addition to the vertical slot corresponding to the guiding body distal slot and adjustable depth stop, an alignment projection 8 is shown. The alignment projection can form a right angle with the depth stop and have a beveled tip to ease insertion. The alignment tip can be a relatively flat and rectangular projection that in use can be rotated and rocked between to vertebrae or a hole in an anulus to distract the vertebrae. Upon partial or full distraction the tip and at least part of the guiding body can be inserted between the adjacent vertebral bodies. The depth stop can limit the amount of insertion by catching the edge of one or both of the opposing vertebral endplates. Vertebral taxis or the resistance of the anulus and endplates to further distraction can serve to immobilize the guiding body as the anchor is hammered out. Alternatively the body can be wedged along an inferior superior plane to drive the opening of the guide way chamber against the desired anchor site. In another embodiment one or more depth stop surfaces may contain one or more barbs, spikes, nails, fasteners, or means for engaging or immovably coupling the distal end of the body to a boney structure such as a vertebral body. In one embodiment an upper depth stop surface may be configured to engage a superior vertebral body and a lower depth stop surface may be configured to engage an inferior vertebral body.

Although the push rod and hammering method described infra is a preferred method of delivery other methods and devices can be used for this purpose. For example, compressed gas and hydraulics can be utilized for driving. The push rod can be configured as a piston or threaded rod (that can be rotated to expel the implant) for imparting linear force. Also, the threaded rod or piston can be flexible or have joints along its length to accommodate a curved or flexible guiding body.

Delivery instruments and devices according to one or more embodiments can also be used to implant other devices besides anchors and the like. For example, a prosthetic device (including, but not limited to, a barrier, mesh, patch, or collapsible implant) can be attached or coupled to an anchor according to several embodiments of the present invention, such as described in U.S. Pat. Nos. 6,425,919; 6,482,235; and 6,508,839; 6,821,276, all herein incorporated by reference. In several embodiments, the prosthetic device can be loaded within or along the guiding body of the device. The anchor and the prosthetic device may be constructed from identical, similar, or different materials. The anchor and prosthetic device may be coupled or removably or reversibly. Connections between the anchor and the prosthetic device may be temporary (such as restorable or dissolvable sutures) or permanent. Instead of a prosthetic device that is coupled or attached to the anchor, the prosthetic device may also be of unitary construct or integral with the anchor.

In one embodiment, an implant such as collapsible patch is coupled to the anchor and oriented along or within the guiding body such that as the anchor is passed through the guide way chamber slot in a downward direction the patch is extruded outwardly or parallel to the long axis of the body. The patch can be held within the body which can have linear slot adjacent the curved slot of the guide way chamber or alternatively the patch can be mounted around the guide way chamber while coupled to the anchor within the chamber. Also, the depth stop sleeve can also be used to compress and hold the patch in place.

In a further embodiment, one or more anchors can be delivered separately from one or more implants. In one embodiment, the implant is first delivered and positioned and then anchored in place. In another embodiment, the anchor is first established in the implantation site and then the implant is delivered and connected to the anchor.

Figure 6A:
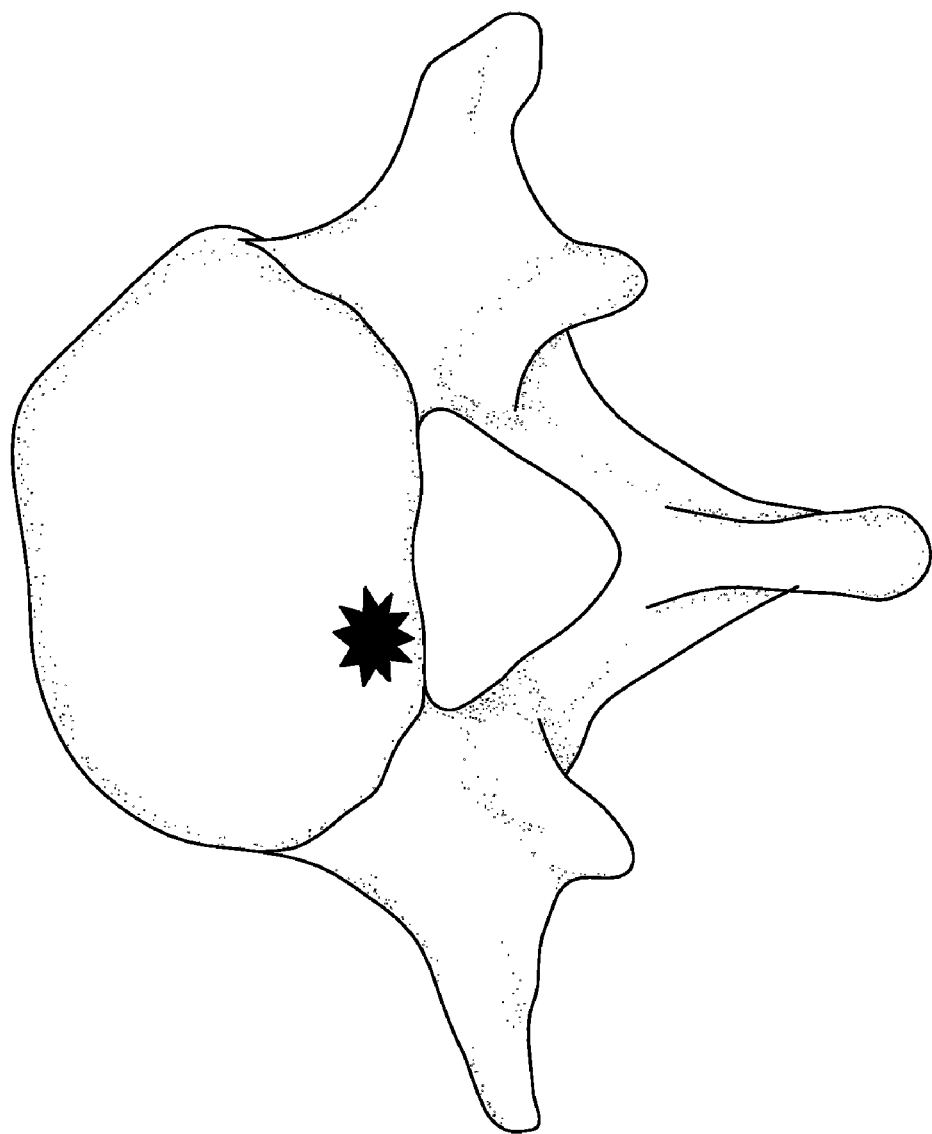
FIGS. 6A-G show a delivery sequence involving a vertebral endplate according to one embodiment.
Figure 6B:
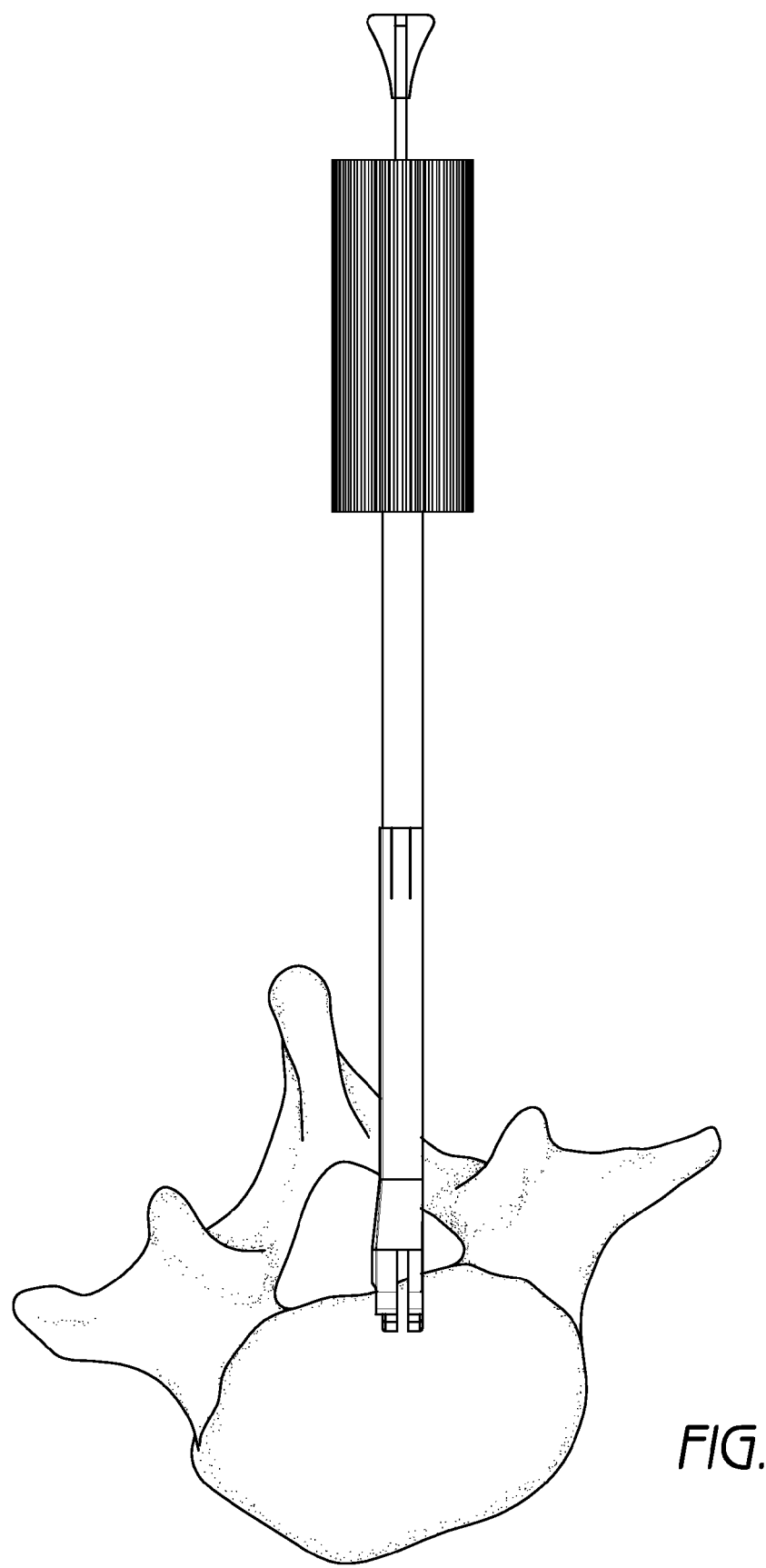
Figure 6C:
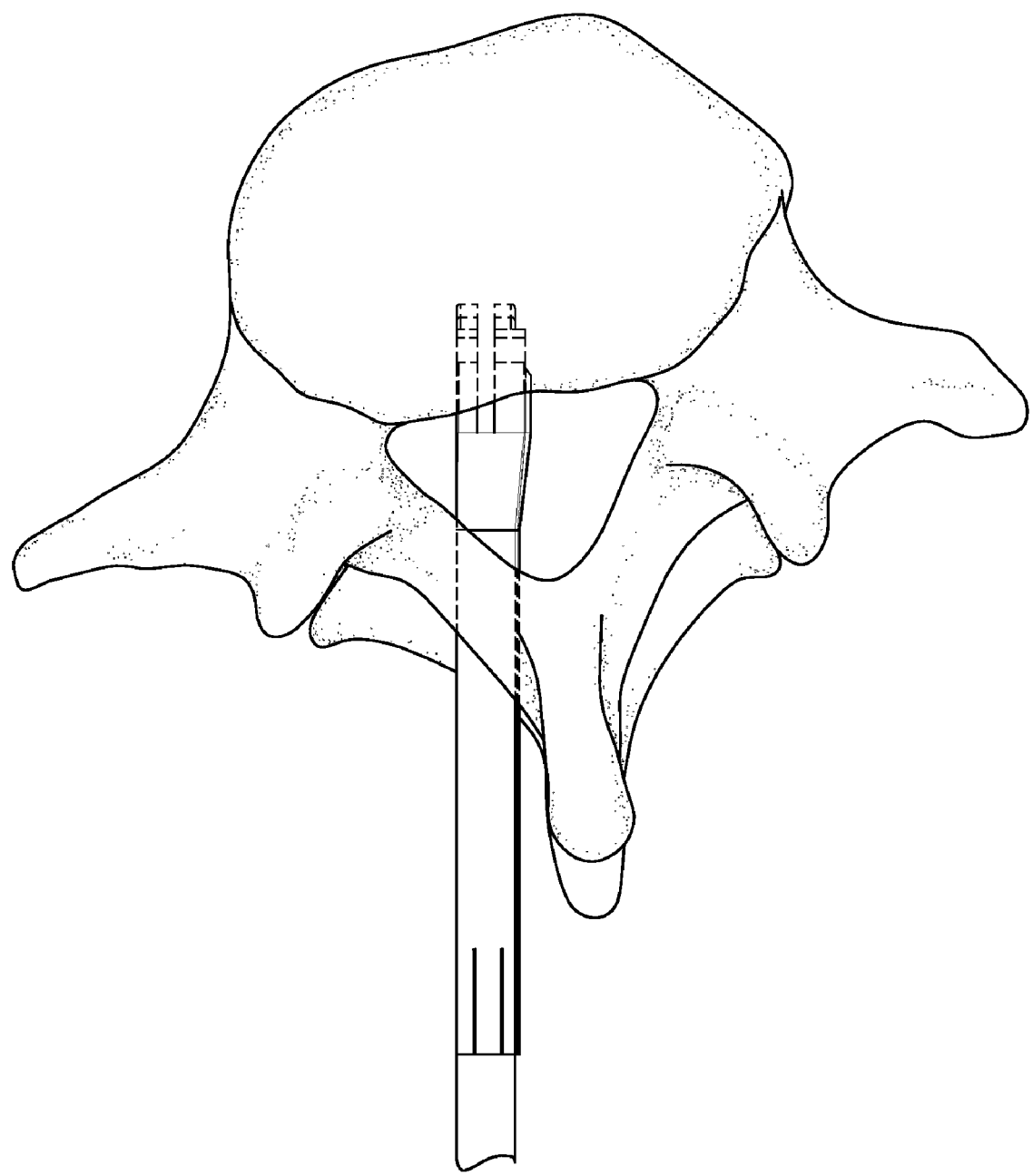
Figure 6D:
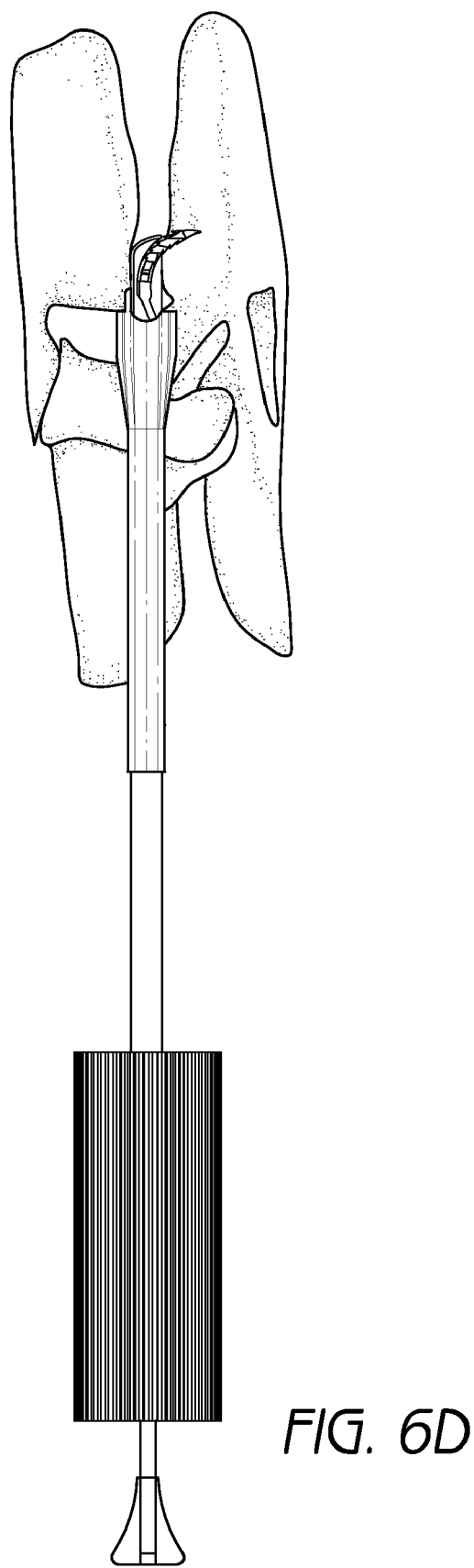
Figure 6E:
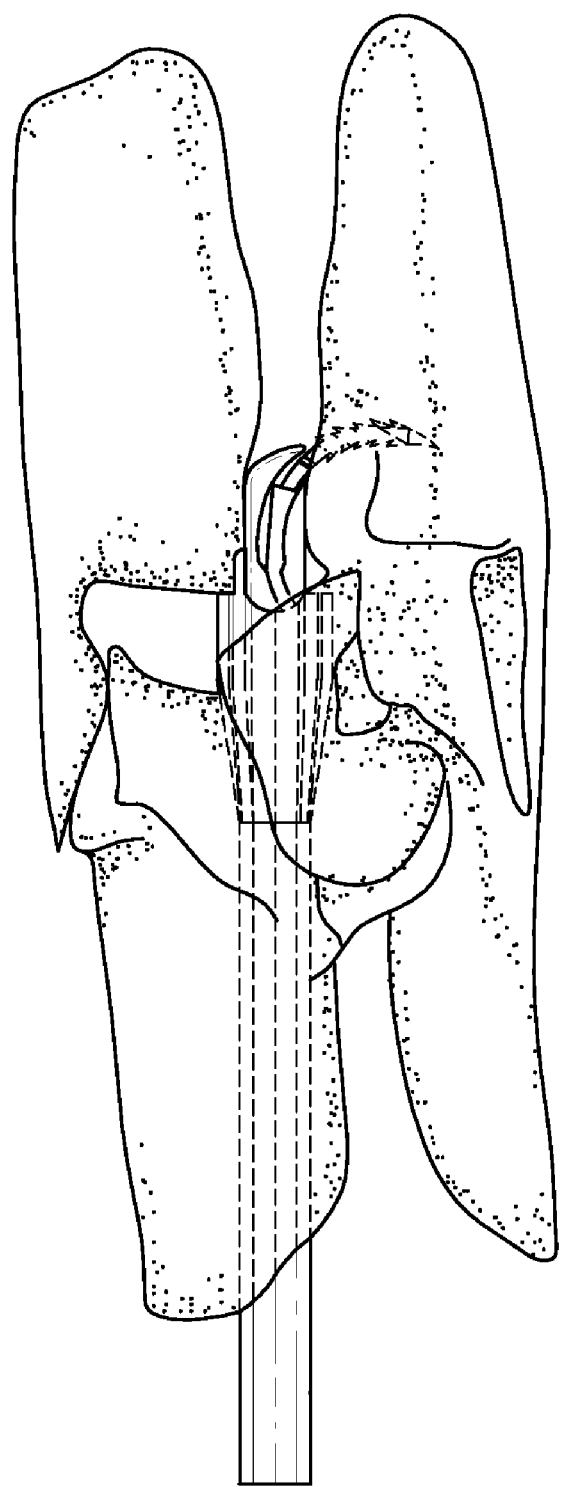
Figure 6F:
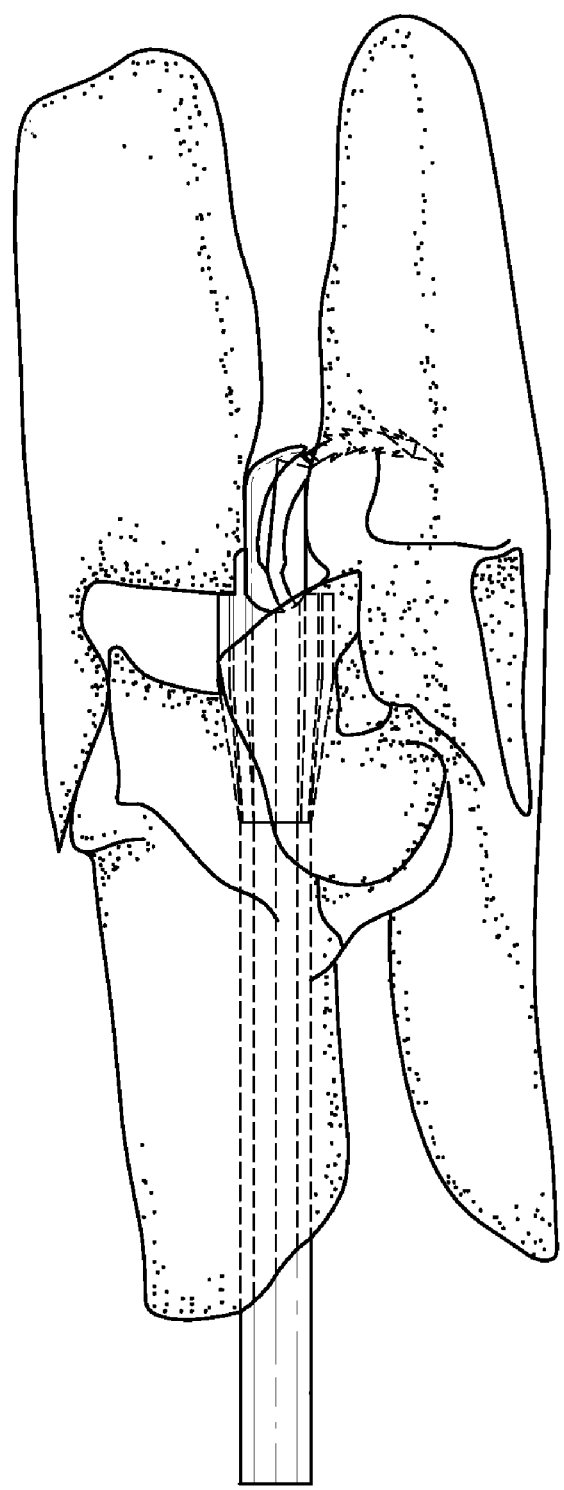
Figure 6G:
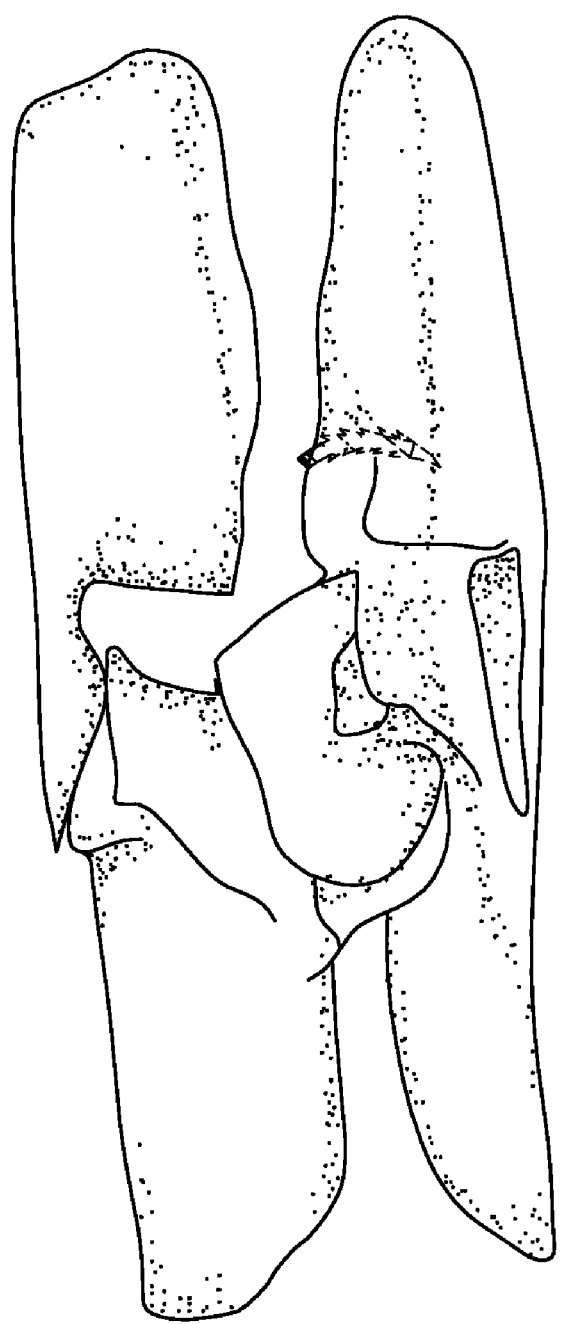

FIGS. 6A-L depicts an implantation sequence according to various embodiments of the invention. FIG. 6A is an axial cross section of a vertebral body, shown is a star shaped treatment zone along the vertebral endplate. The sequence shows an anchor being implanted into a posterior portion of a vertebral body along an endplate. The surface of the endplate can be accessed through a hole in the anulus. The hole in the anulus may be a naturally-occurring defect or surgically created. Methods and devices according to the invention are not limited to a single location along a vertebral body or surgical approach.

Perpendicularly Driven Anchor

Various embodiments of anchor presented herein are designed to improve upon the weaknesses in conventional bone screws and staples that are limited by surgical access and suture or anchor attachment site placement. For example, in the environment of the spine, the posterior elements of vertebral bodies forming facet joints, spinal canal, neural foramen, and the delicate nerve tissues of the spinal cord create numerous obstacles for surgery and diagnostic and interventional methods. Surgical approaches have been adapted to minimize damage to these structures and involve tight windows usually off angle to the target tissue.

Figure 7:
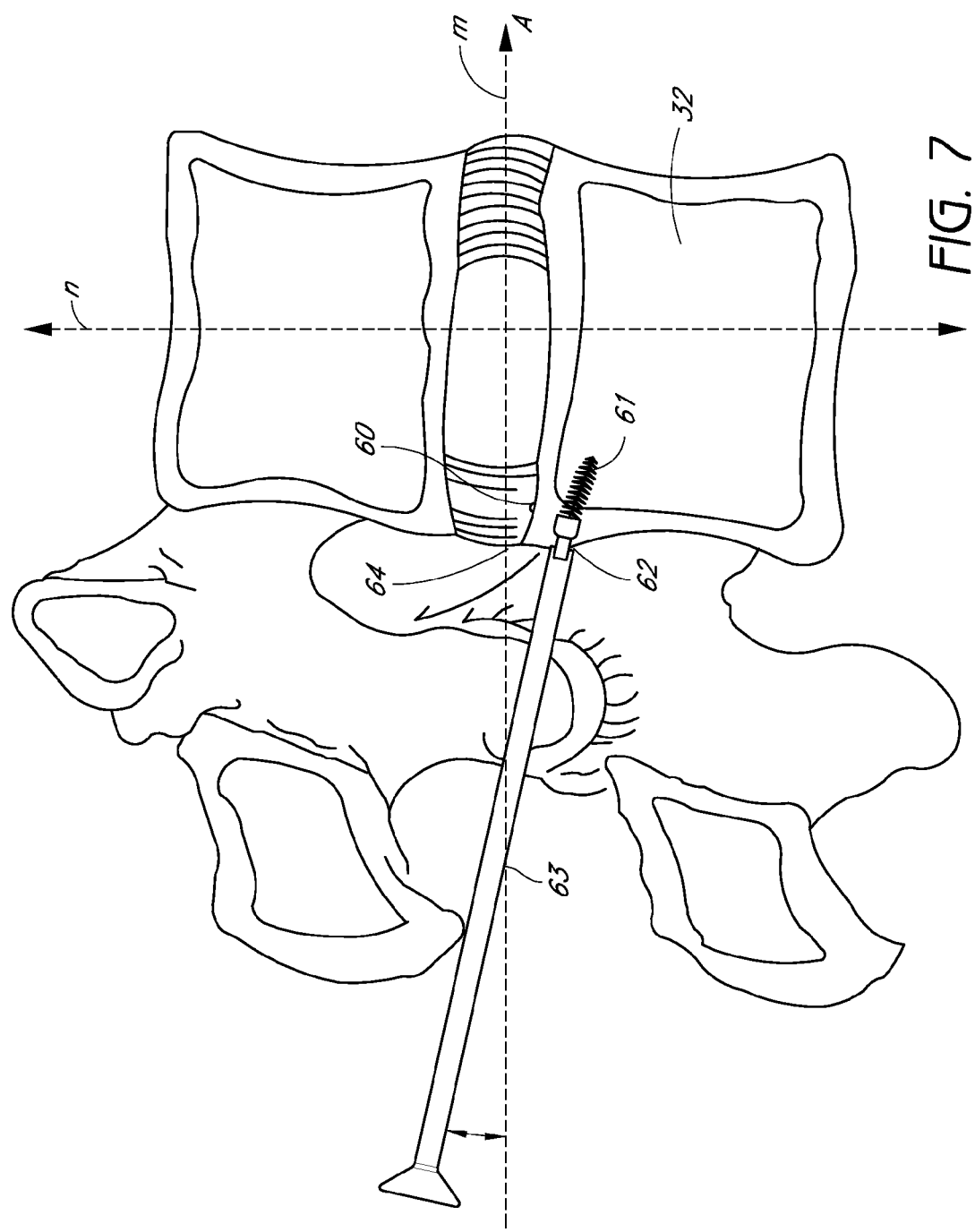
FIG. 7 shows a prior art bone screw and intervertebral anatomy.

An example of such prior art anchor and environment is depicted in FIG. 7, which shows a bone screw driven into a vertebral body from a posterior lateral approach. Here the anchor on the outside of the vertebral body is ineffective for retaining an implant within the disc and remains in dangerous proximity to the spinal cord. Several embodiments of the present invention are particularly advantageous because the anchor does not present attachment sites originating at a proximal end in the axial orientation from which they are driven. Moreover, several embodiments of the present invention are advantageous because the anchor is adapted with an expansion mechanism that provides a "mushrooming" effect, and thus the pull-out resistance is not merely limited to the friction and forces generated by the sidewalls of the material or tissue.

Several embodiments of the presentation invention accommodate or exploit certain geometries or anatomical structures of the body. For example, in one embodiment, the attachment site of an anchor can be presented distally from the insertion site in a direction perpendicular or offset from the axial orientation of insertion. In one embodiment, the anchor presents a larger surface area below or embedded within a surface, thereby offering improved pull-out resistance without requiring an expansion or "mushrooming" step or mechanism.

In several embodiments, one or more anchors are driven into the surface of a first plane and present a portion on an adjacent plane or surface perpendicular or angled relative the first plane. Thus, the anchor is driven into a first surface and across an adjacent surface in the same instance. In one or more embodiments, at least a portion of the anchor such as the anchor attachment site is adapted to remain above or proud of the upper or second tissue surface or plane. With respect to the first surface (the front facing or lower surface into which the anchor is driven), the anchor can be driven in to a depth such that it is countersunk, left flush, or left partially external to the frontal tissue surface or plane. The anchor can also be delivered at a trajectory or angle relative to the second or top surface such that it is driven into the first surface and downwardly or upwardly across the second surface.

In several embodiments, the anchor is a flat plate-like nail or brad having a specialized keel portion and neck portion. In other embodiments the anchor is flat, plate-like, curved, corrugated, round, or a combination thereof. The neck can be terminated in a head or present an attachment portion along its length. The attachment portion or site can be comprised of a more flexible piece of fabric, wire, linkage, fastener component, hook eye, loop, or plate. The neck can be an extension, ridge, midline, or the apex of the keel portion. The neck can be oriented at the distal or proximal end of the keel or anywhere along its length. The neck can be the same length as, longer than, or shorter than the keel but preferably it is shorter. In one embodiment, the neck is a thin rod or beam. The keel portion can have a cross-section similar to a wedge, "V", "U", "T", "W", "X" and other shapes.

Anchors according to one or more embodiments of the present invention have dimensions suitable to the implantation environment. For example, in one embodiment, the anchor has a height of about 0.2 cm to about 5 cm and a width of about 0.2 cm to about 5 cm. Anchors can have a length or depth from 0.2 cm to about 5 cm. In some embodiments, the length, width, height or depth can be less than 0.2 cm or greater than 5 cm. In one embodiment, the anchor has a length of about 1 cm and a width of about 0.5 cm. In yet another embodiment, the anchor has a length of about 0.5 cm and a width of about 0.25 cm. In another embodiment, the anchor is dimensioned as follows: about 0.3 cm wide, 1 cm long and 0.5 cm deep.

The length of the anchor can define a straight or curved line defined by a radius of curvature of about 0-90 degrees (e.g., about 15, 30, 45, 60, or 90 degrees). The keel, legs, extensions, blades, or fins can have a leading edge that is sharpened, left dull, or serrated. Other features of the neck and keel or extensions include, but are not limited to, barbs, tabs, roughened surface geometry, polished surface, coatings seeded carrier or drug eluting coatings or elements, concavities, scalloped ridges, grooves, "feet", ridges, voids, slots, and ingrowth openings are shown in the attached drawings. Secondary edges or ribs can protrude along portions of the keel to provide enhanced engagement with tissue.

In addition to the neck and anchor attachment site, the anchor can also include an alignment means, engagement means or guide. Variations of the anchor alignment means can function to orient the anchor to a driver and couple it thereto. The anchor alignment means can comprise alignment components such as a protrusion, recess, or fastener component mated to a portion of a delivery instrument. The anchor engagement means can comprise engagement components or portions such as spikes, teeth, prongs, barbs, friction zones, or a combination thereof. The guide can comprise a protrusion, slot, arrow, tab, or a combination thereof. Thus, in some embodiments, the anchor comprises means to align, means to engage, means to guide, or a combination thereof.

Figure 8:
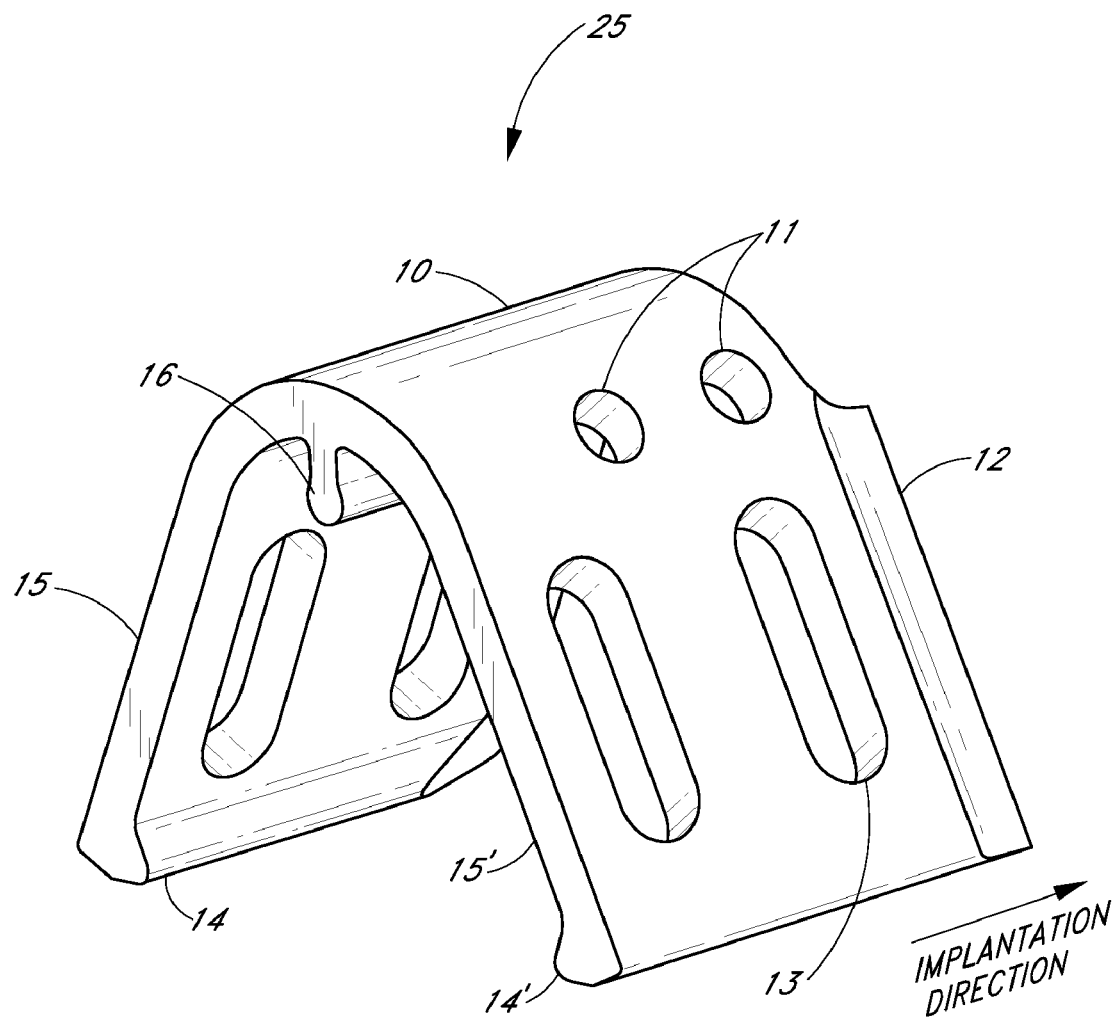
FIG. 8 shows an embodiment of an anchor according to one or more embodiments of the invention.

Turning to the drawings, FIG. 8 shows an embodiment of an anchor 25 with a leading edge 12, suture attachment sites 11, ingrowth features or voids 13, first and second plate-like legs or lateral extensions 15, 15' defining the keel, arcurate central ridge or apex 10, centering or alignment projection 16, and feet or ridges 14, 14'. Both the wedge-like shape of the keel portion of the implant i.e., the legs and the ridges or flange like extensions at the end of the legs function to hold the implant within a given tissue and to resist rotation and pull out from a variety of angles. The voids and ingrowth features serve to provide secondary stabilization over time and/or to allow chemical transfer or cellular respiration across the implantation site.

In a "V" shaped anchor or similar embodiment shown, the neck portion is bifurcated into two legs, extensions, blades, fins, or keels that meet at an apex and form an angle between about 10 and about 170 degrees. In one embodiment, the angle is about 30-90 degrees. The apex at the point of bifurcation can define a flat ridge or vertical extension or neck that can contain one or more anchor attachment sites. In a "U" shaped embodiment the neck can be in the form of an arc or eye projecting along the length of the body of the anchor. "V" or "U" shaped anchors can be modified to "L" shaped anchors in some embodiments.

Figure 9:
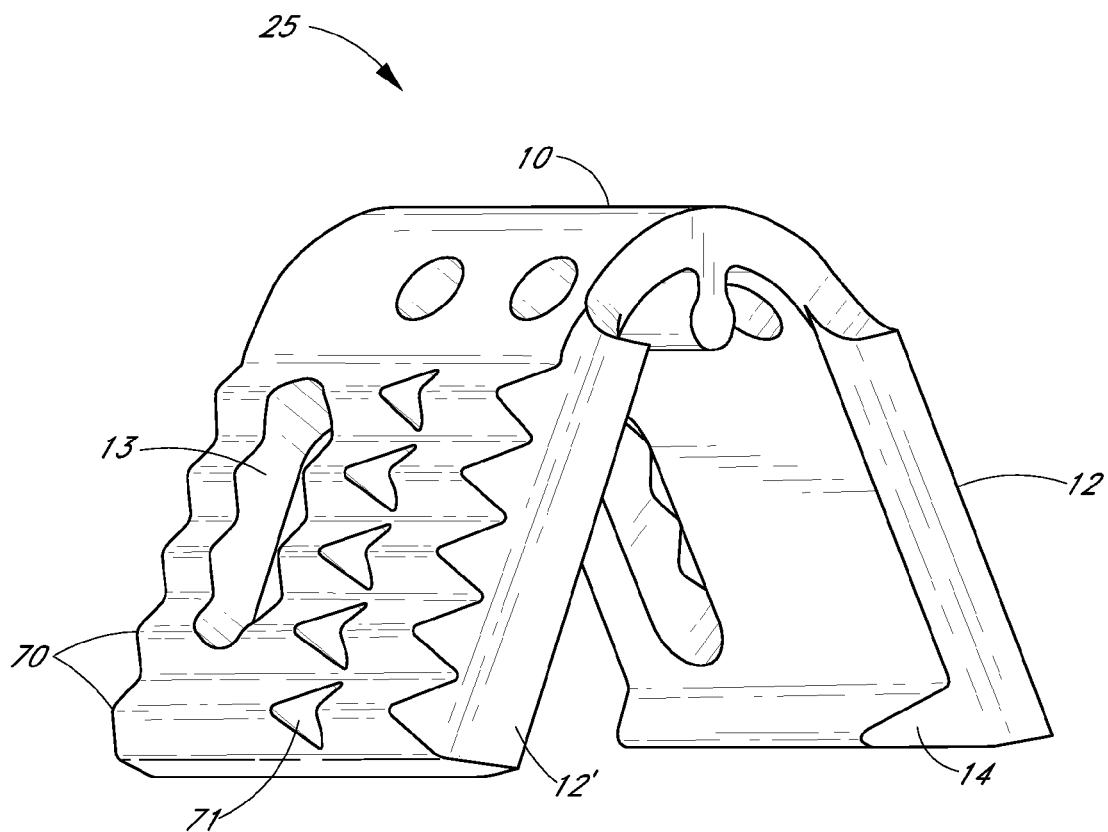
FIG. 9 shows another embodiment of an anchor according to one or more embodiments of the invention.

In FIG. 9, an anchor similar to the one depicted in the previous figure is shown. The apex 10, which would correspond to the neck in other embodiments, does not extend and instead presents a smooth curve which can present a less injurious profile to the anatomy in certain applications. Also shown are ridges 70 and scalloped teeth-like surface features 71.

Figure 10:
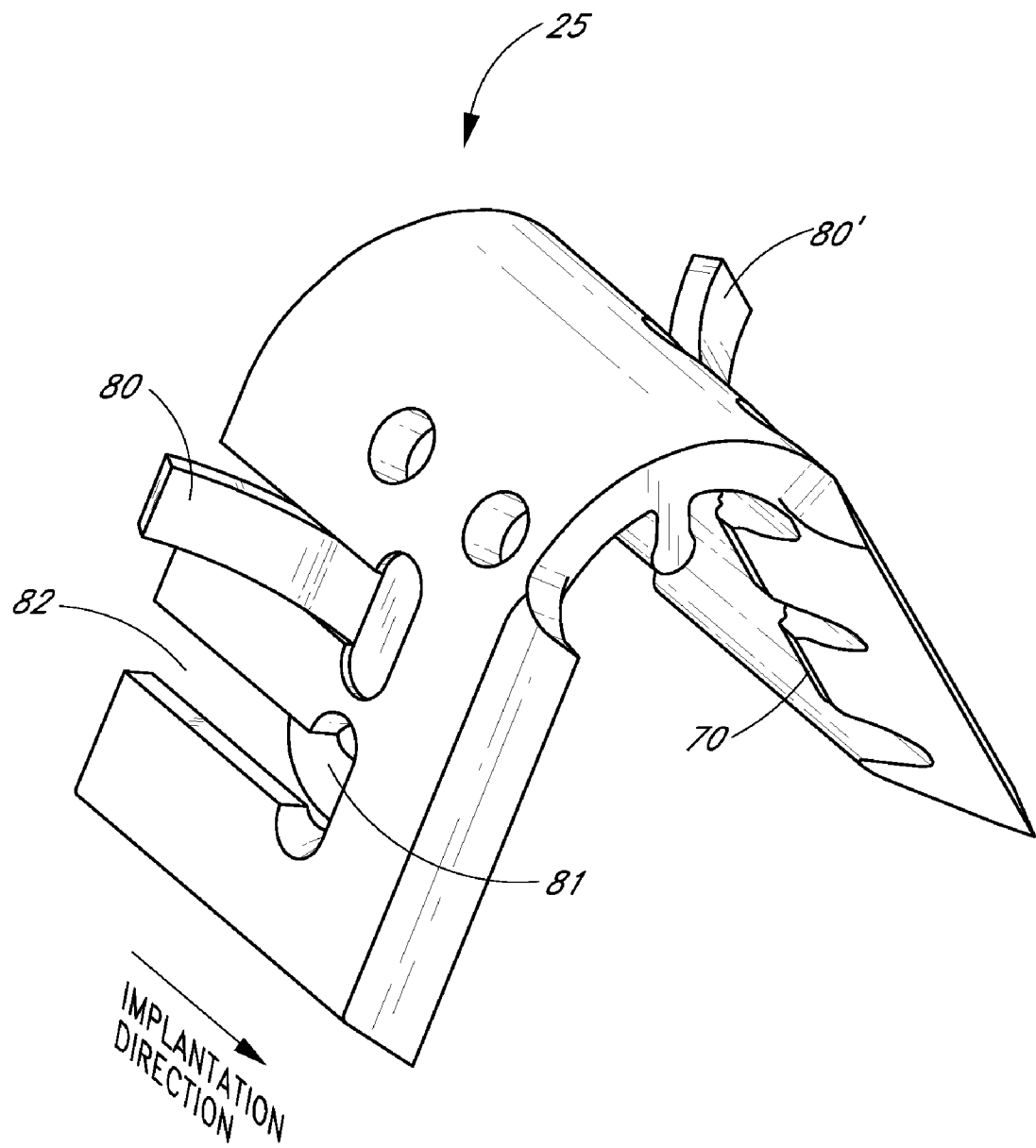
FIG. 10 shows another embodiment of an anchor according to one or more embodiments of the invention.

FIG. 10 shows another embodiment of an anchor with deployed barbs 80 and 80' These features can be held compressed within a sleeve on a delivery instrument or simply forced to compress inwardly as the implant is driven in to tissue. One or more slots or recesses 82 are adapted for holding the barbs during implantation to streamline the anchors profile.

One or more barbs can exert continuous outward pressure on the sidewalls of a tissue or expand to their maximum and form a shelf or flange if the tissue geometry widens, expand or become more pliant. For example, in a vertebral body the implant might be driven into cortical bone and then further into cancelous bone. Upon reaching the cancelous bone, the barbs flexible plate-like structure or engagement means, can expand or extend outwards. In another example the anchor is driven at least partially into the hollow of a boney structure such that the barbs expand and engage the inner wall of the bone. Element 83 is an opposing barb or expansion means however one or more barbs can be oriented relative to each other from 0-360 degrees. For example, the barbs or other barb-like components may be orientated relative to each other at the following angles: 15, 30, 45, 60, 90, 120, 150, 180, or 360 degrees.

Figure 11:
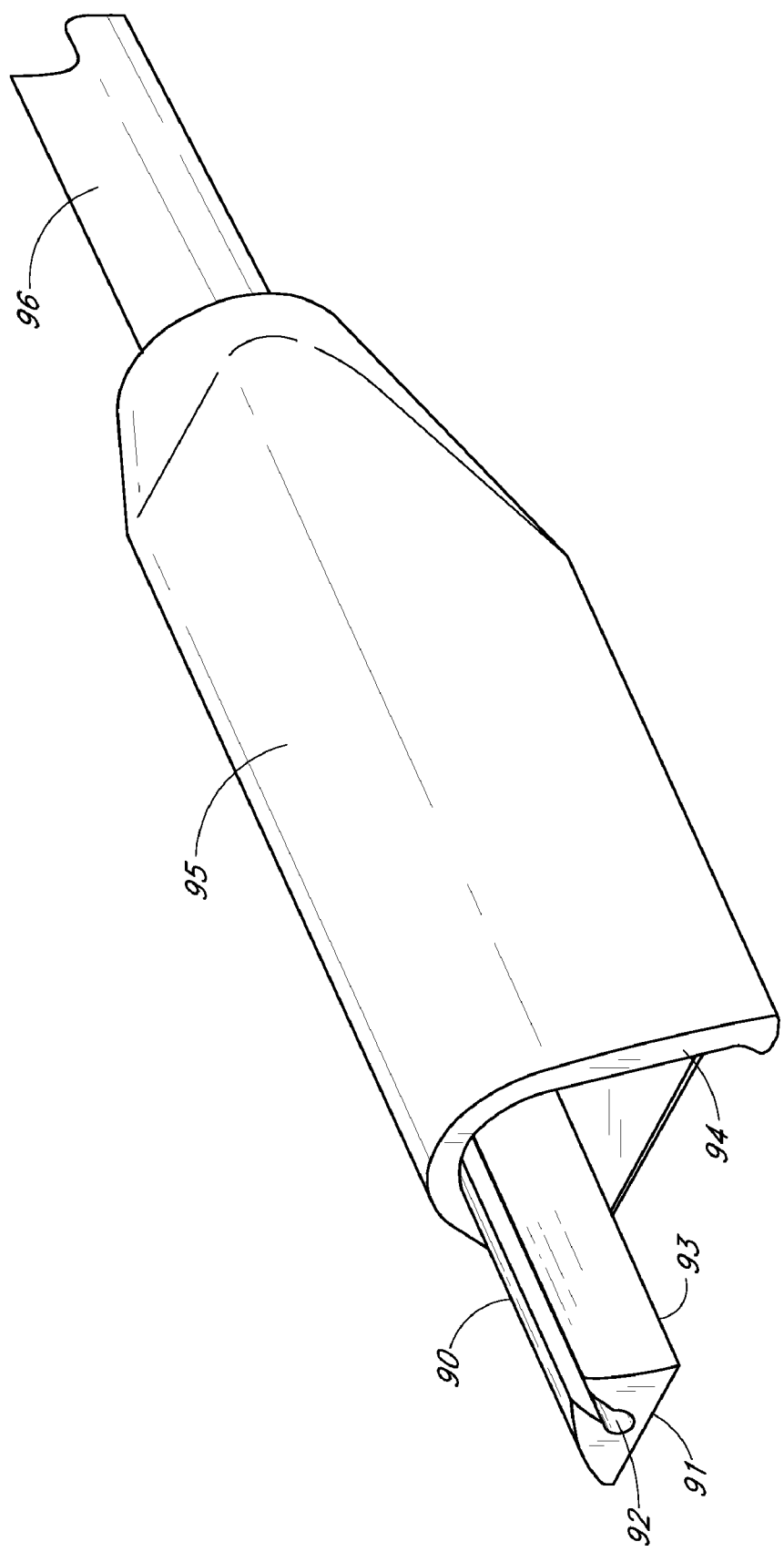
FIG. 11 shows one embodiment a delivery tool.

FIG. 11 shows a delivery tool with a shaft 96 with distal end 95 having an anvil or striking surface 94 defining a leading edge mated to at least a portion of the cross section of the trailing edge of the anchor. The shaft may be connected at its proximal end to a handle or terminate in a striking surface. Because the anvil surface is similar to the anchor in some embodiments, both the anchor and at least part of the distal end of the delivery tool can be driven into a bone thereby counter sinking it. Alternatively, anchors according to one or more aspects of the invention can be left flush or partially countersunk. A mounting member 90 may extend beyond the implant when the implant is mounted or loaded on the tool. The mounting member 90 includes a flattened lower surface 93 and a rounded blunt front surface 91 for positioning along a bone surface, such as the top of a vertebral endplate, and a slot or engagement means 92 for accepting an aligning an anchor.

Figure 12:
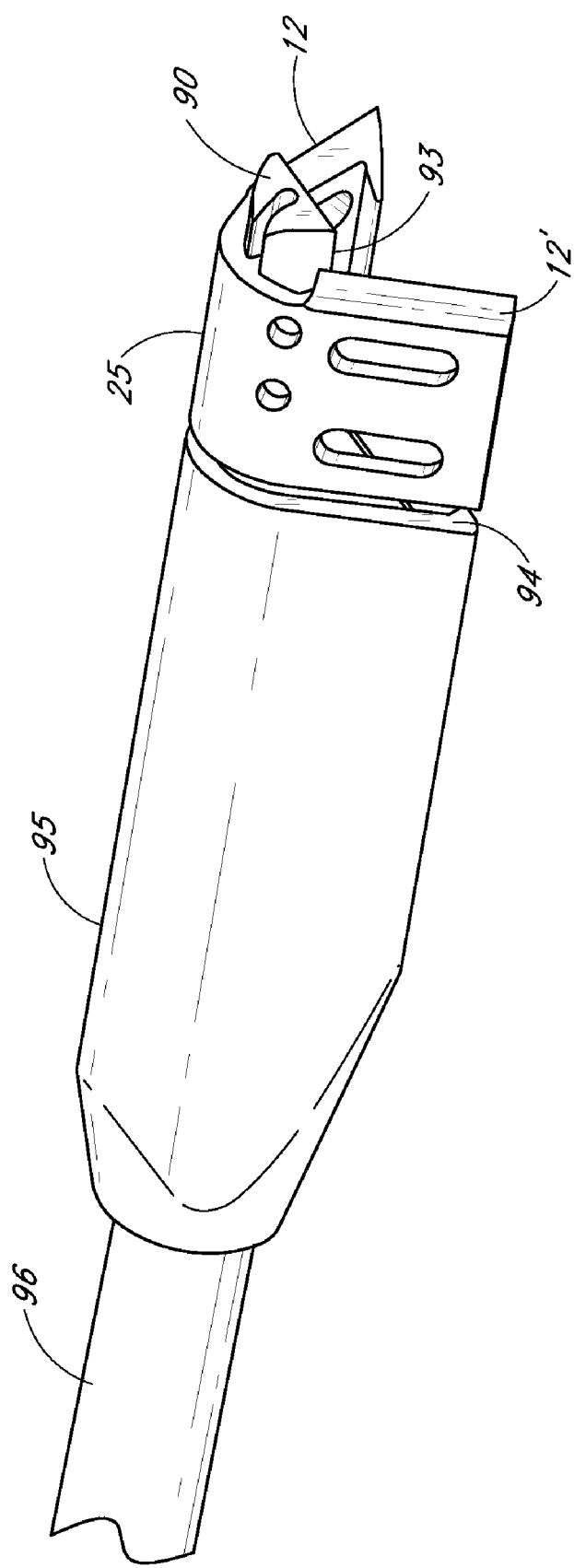
FIG. 12 shows the delivery tool in the previous figure with an anchor mounted

FIG. 12 shows the anchor 25 mounted on the mounting member 90. The extended lower surface 93 and the leading edge of the implant 12 and 12' forms a means to engage bone or other tissue. In one embodiment, the tissue (e.g., bone) engagement means comprises a device having an angled surface that may be used to hook onto, engage, or align the instrument with the edge of a vertebral body or the intersection of two tissue planes. In one embodiment, the engagement means can be used to align the implant with the top of a vertebral endplate and its front outer surface, the anchor is then driven into and across the endplate.

Figure 13:
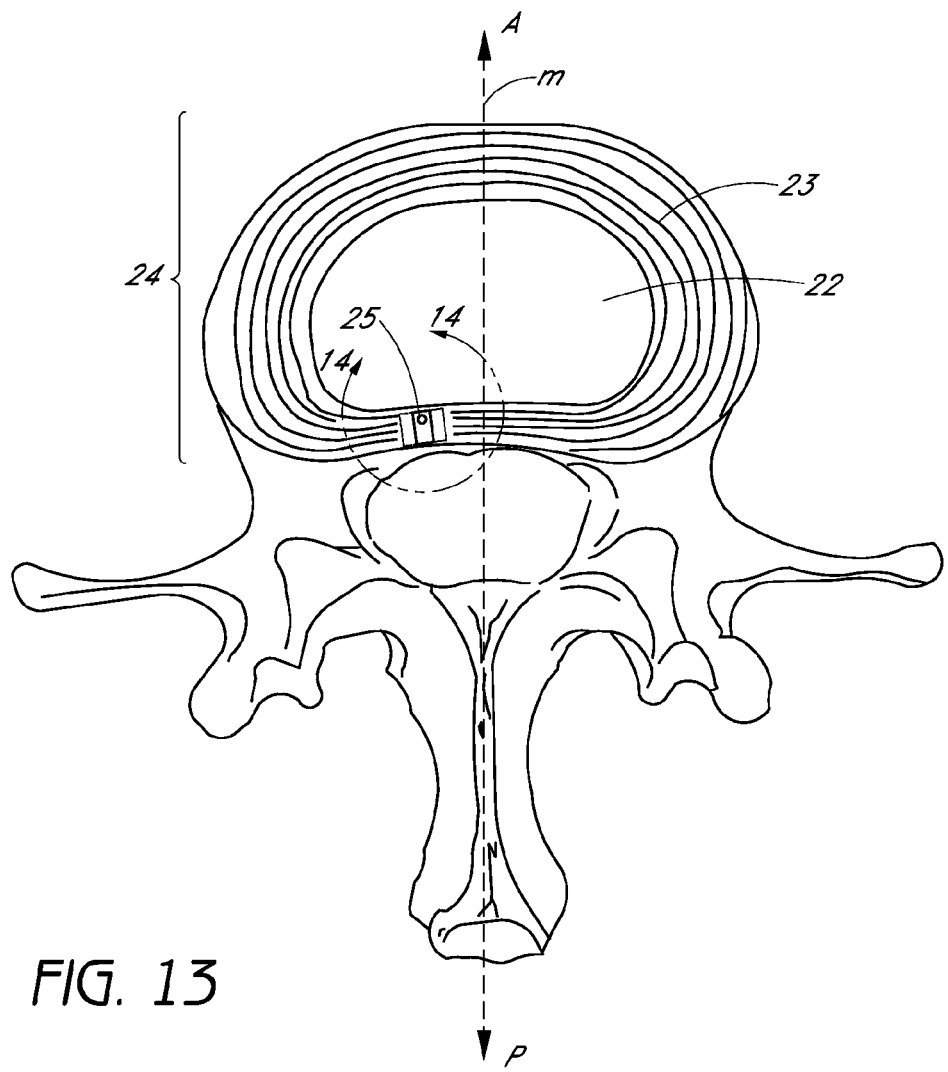
FIG. 13 shows an axial cross sectional view of a vertebral body and implanted anchor.

FIG. 13 shows a cross-section of a vertebral body 24 having an anulus fibrosus 23 bounding nucleus pulposus 22 with an anchor 25 embedded into a posterior aspect of an endplate and within or proximal to an anulotomy or defective region of the anulus fibrosus 23. This implantation site is also in the vicinity of the cortical rim or ring of dense bone of the vertebral endplate. The anchor is shown countersunk into the bone along the P-A axis but partially proud along the inferior-superior axis (the dotted lines indicating the portion of the implant below bone surface or level.

Figure 14A:
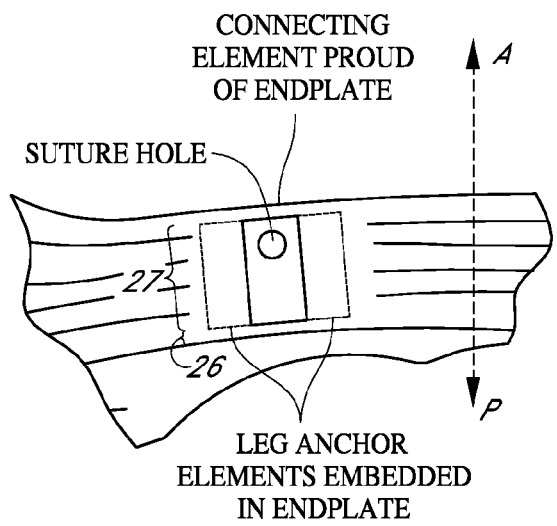
FIGS. 14A-B show an expanded view and a frontal view of the implanted anchor in the previous figure.
Figure 14B:
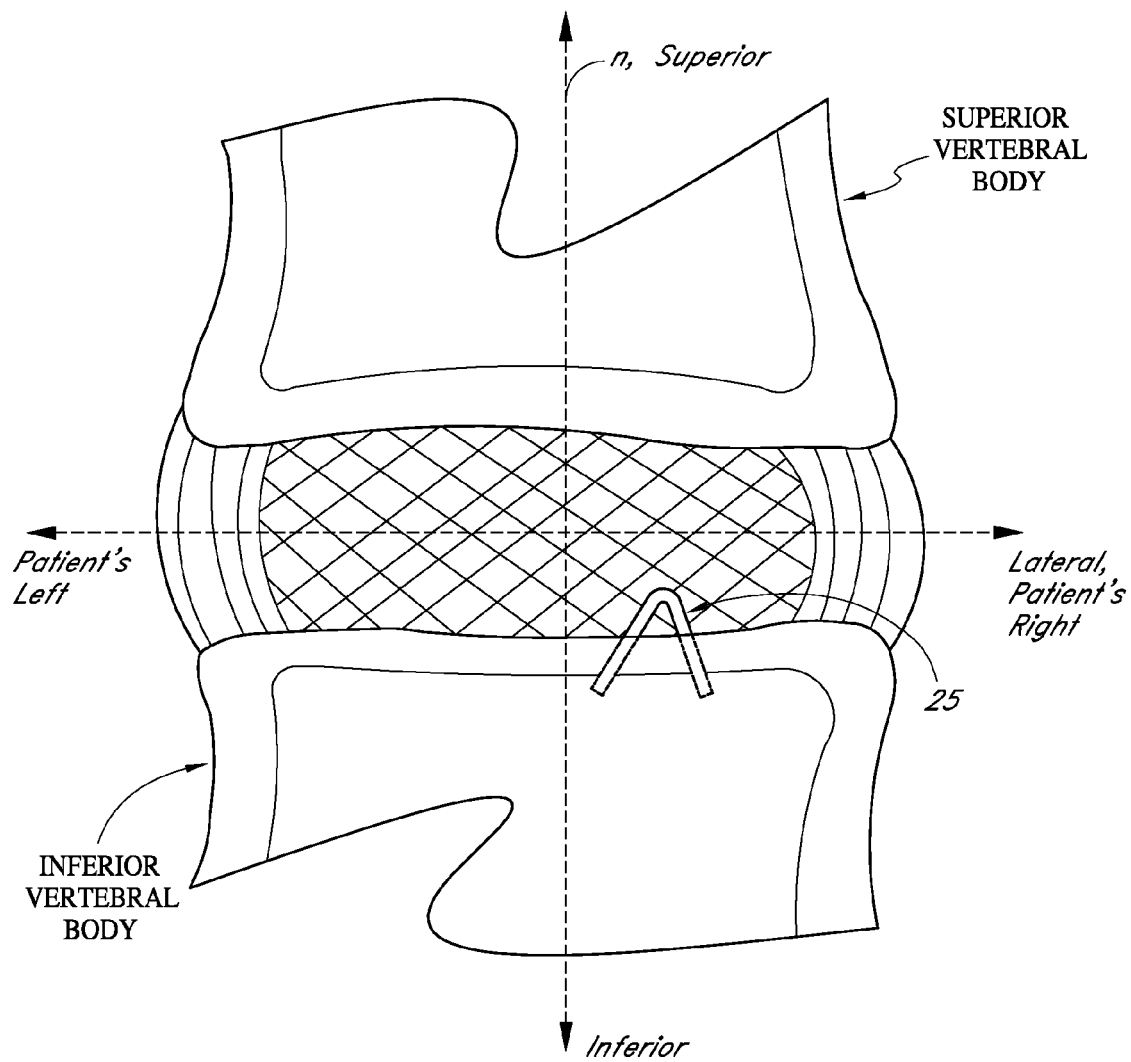

FIG. 14A is an expanded view of FIG. 13 and shows dotted lines to represent the keel portion of the anchor 25 beneath the endplate surface. FIG. 14B is a dorsal view of FIG. 14A showing anchor 25.

Figure 15:
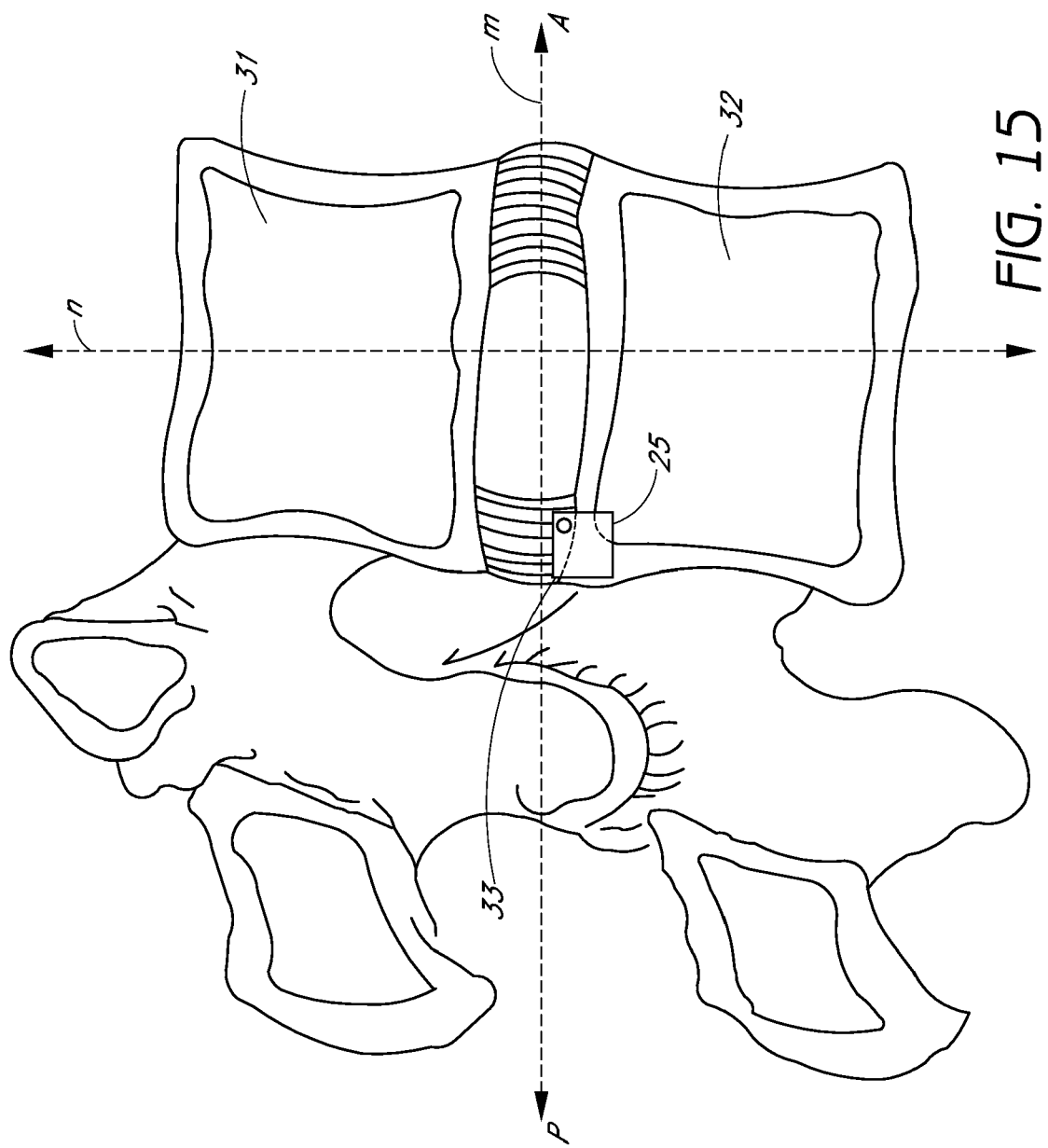
FIG. 15 shows a sagittal view of the implanted anchor in the previous figures.

In FIG. 15, a sagittal view of an implanted anchor 25 is shown at least partially within the defect 33 and inferior vertebral body 32. Superior vertebral body 31 is also shown. The cross-section of the vertebral bodies depicts the denser and thicker bone at the edge or rim where the anchor is implanted and the less dense cancellous bone within the vertebral body.

Figure 16:
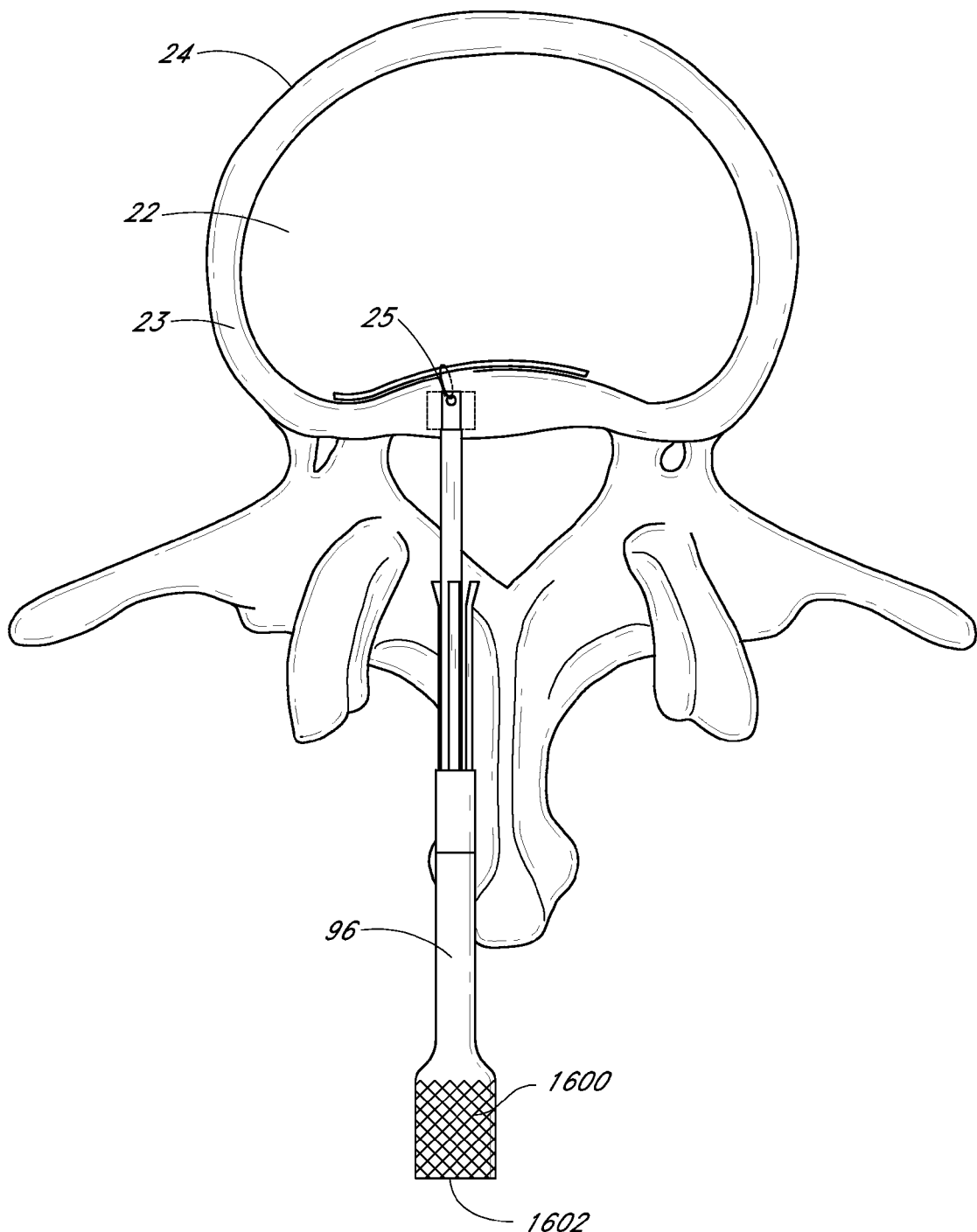
FIG. 16 shows an axial cross sectional view of a vertebral body and a delivery tool inserted along an endplate in the vicinity of an anulus defect or anulotomy.

FIG. 16 depicts a method of delivery for one embodiment of the anchor and associated delivery tool. Shown is a top cross sectional view of a vertebral body 24 and a delivery instrument 44 and an anchor 25. The delivery instrument or driver is used to transmit the force of a hammer or other means to drive the anchor in place. The driver can comprise a slot, holder, magnet, pins, mateable surfaces, fastener or other means at its distal end to engage or couple with the anchor. The anchor can also be attached to the distal end of the driver and then released once the desired delivery depth has been attained. Other features of a driver (not shown in FIG. 16 can include a depth stop, bone engagement means such as a spiked, hooked, or angled protrusion, and/or a retractable sleeve to protect adjacent anatomy as the anchor is positioned. FIG. 16 also shows a flat proximal end 1602 for hammering, if needed and a knurled handle 1600.

Figure 17:
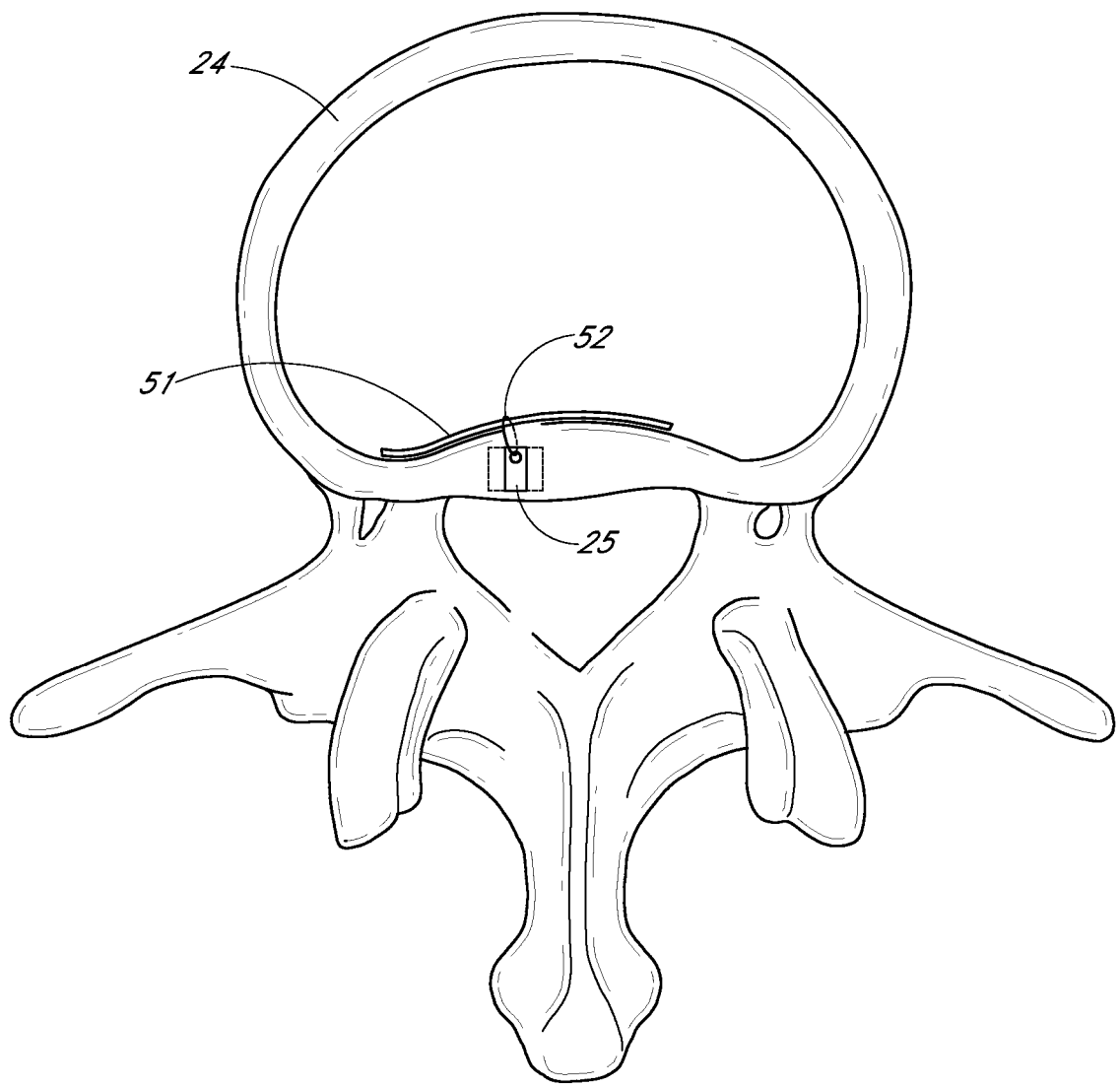
FIG. 17 shows an axial cross sectional view of a vertebral body wherein an anulus reinforcement device has been implanted along and within the anulus and is attached to an anchor embedded within the vertebral body.

Turning to FIG. 17, a top cross-sectional view of an anulus repair implant 51 lying along the inner surface of the posterior anulus is coupled, attached, or sutured 52 to an anchor 25. The connection between the anchor and implant can be permanent or detachable. The implant 52 can be delivered and positioned prior to, at the same time as, or subsequent to the implantation of the anchor 25. FIGS. 17A-17C show various features of anchors.

Figure 18A:
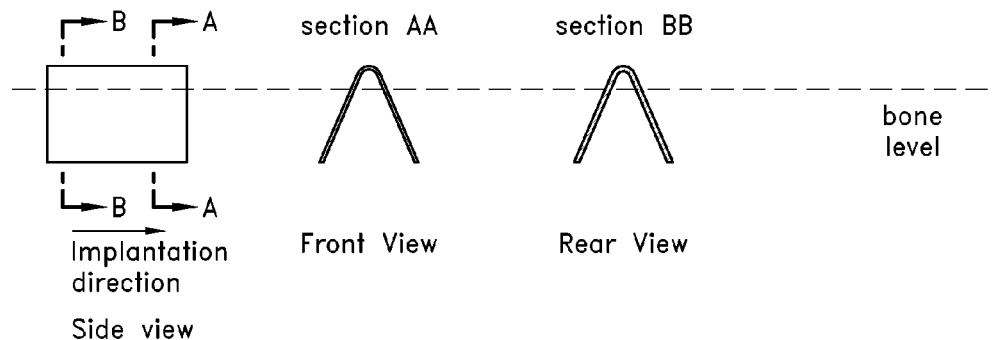
FIGS. 18A-C show various views and features of anchors according to one or more embodiments of the invention.
Figure 18B:
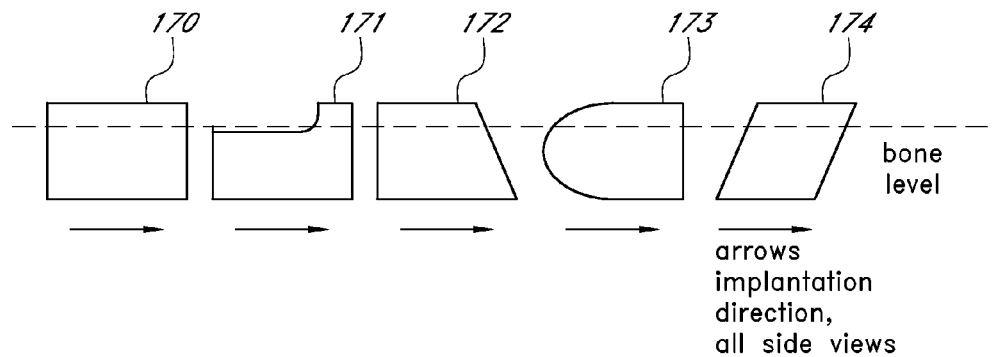
Figure 18C:
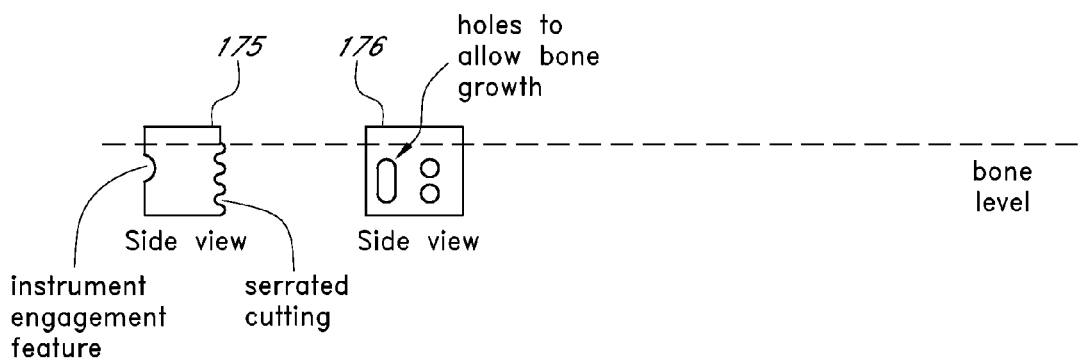

In FIG. 18A, the surface level of a bone such as a vertebral endplate is shown as a dotted line. A side view is depicted. Here the leading edge of the keel or leg portion of the implant is thinner than the trailing edge. Accordingly, in other embodiments of anchors according to the invention at least a portion of the leading edge, profile, proximal edge or side of an implant can have a thinner or tapered profile than an opposing end, distal end, or trailing edge or profile. FIG. 17B shows a series of anchor variations from a side view in which the top portion, apex, neck, or implant attachment site 170, 171, 172, 173, 174 is symmetrical, rounded, wedge shaped, oriented at the distal or proximal end of the anchor. FIG. 18C shows another side view along the bone surface level depicting and anchors with features discussed infra such as a serrated leading edge, voids or ingrowth holes, and a recess for engaging a delivery tool.

Figure 19:
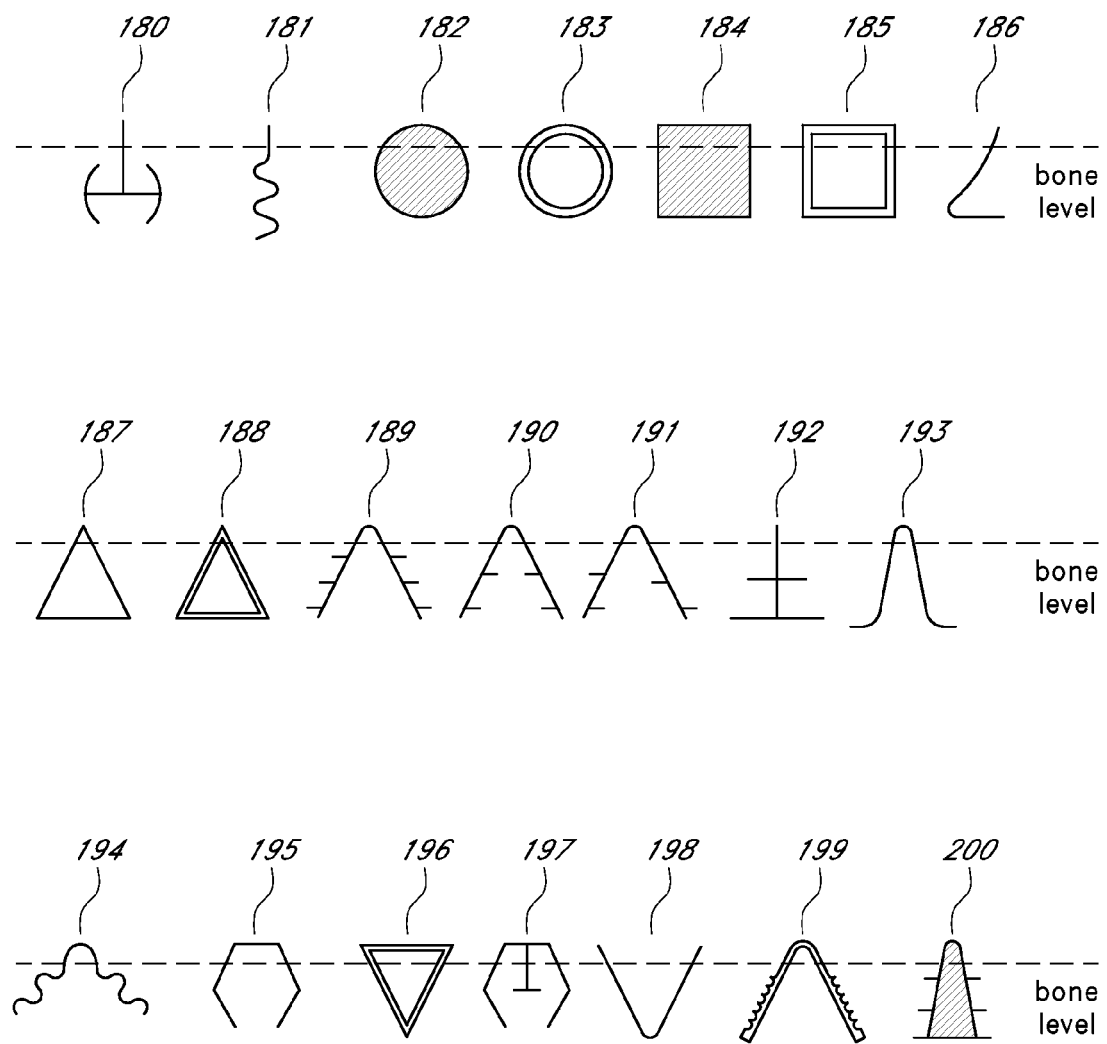
FIG. 19 shows various profiles of the keel portion of one or more anchors.

FIG. 19 shows various embodiments of the anchor cross-sections including several keel profiles from a front view resistant to pullout and offering various surface areas. Some are solid shapes as in anchor profiles 182, 184, 187, and 200 and others are hollow and have an open midsection as in anchor profiles 183, 185, 188.

Figure 21:
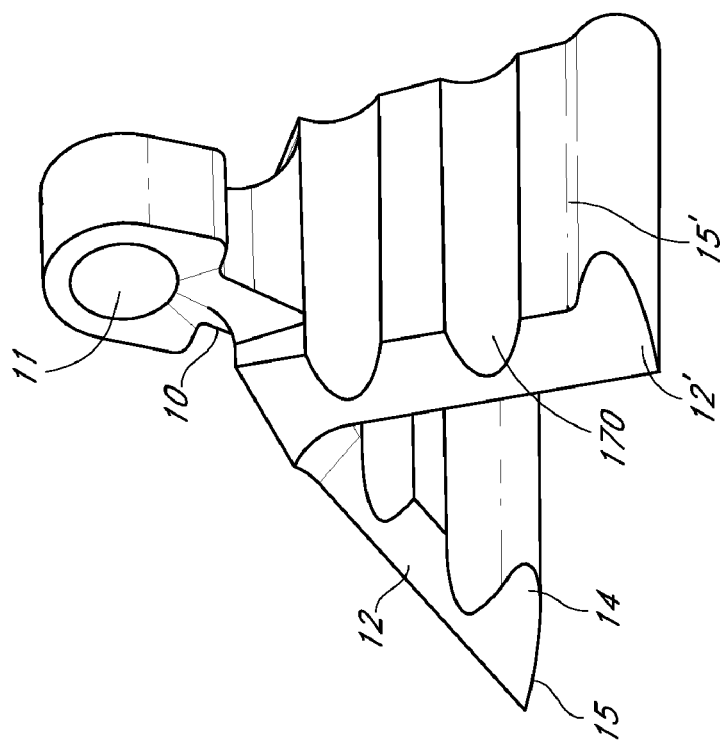
FIG. 21 shows a perspective view of another embodiment of an anchor according to one or more embodiments of the invention with an "eye" attachment means.
Figure 20:
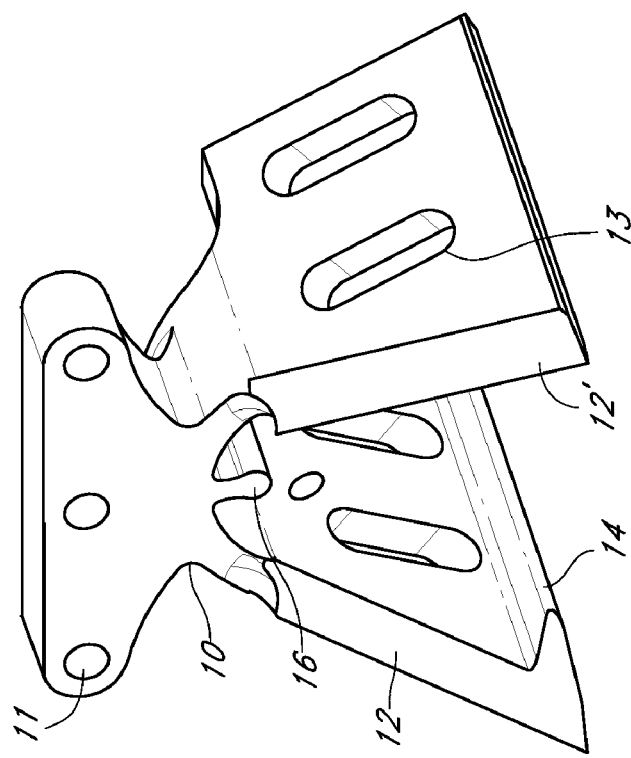
FIG. 20 shows a perspective view of another embodiment of an anchor according to one or more embodiments of the invention with a plate-like attachment means suitable for three sutures.

Turning to FIG. 20, a perspective view of an anchor is shown with leading edges 12, 12', alignment means 16, suture or fastener attachment 11 site or neck 10, and voids 13. In this embodiment the apex does not run the entire length or depth of the anchor corresponding to the keel or opposing leg portions 15, 15' of the anchor. Also, the neck is oriented towards the proximal end of the anchor forming a cut-out along the top portion of the anchor. The neck 10 is shown perpendicular to the keel 15 but can be alternatively oriented in a range from 0-180 degrees relative to it. In one embodiment, the neck is oriented at an angle of about 15, 30, 45, 60, 75, 90, 120, 150, or 180 degrees relative to the keel In FIG. 21, a "V" shaped anchor is shown. An "eye" or loop is integral to a neck extension portion 10 that bifurcates into two legs 15, 15'. Because the leading edges 12, 12' and at least a portion of the neck 10 is sharpened, this anchor can be driven more flush to the upper or first surface of a bone such as a vertebral endplate. Here both the neck 10 and the leg portions 15, 15' of the device function as a keel. This embodiment also shows ridges 12 and scalloped recesses. Anchors according to other embodiments described herein may also comprise ridges and/or scalloped recesses.

Figure 22B:
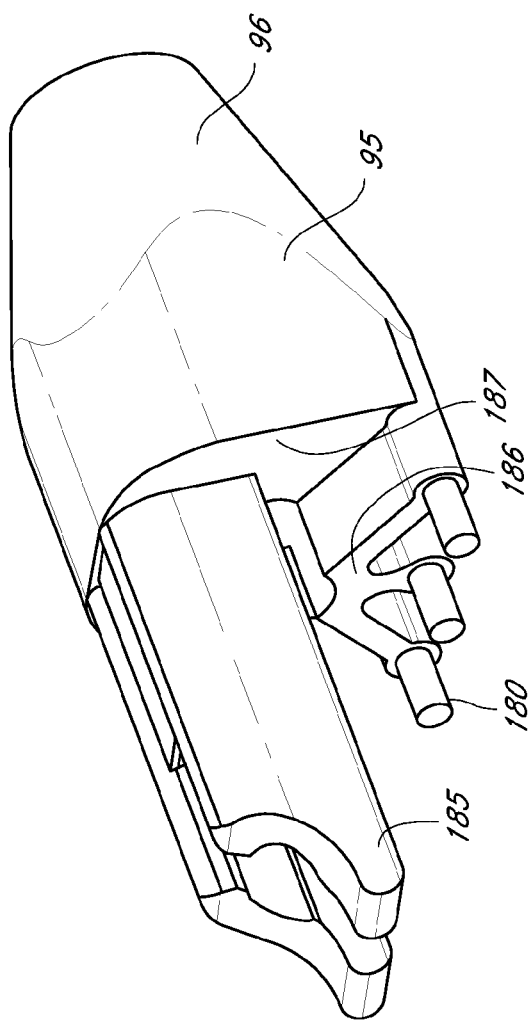
FIGS. 22A-B show embodiments of the anchor and delivery tool.
Figure 22A:
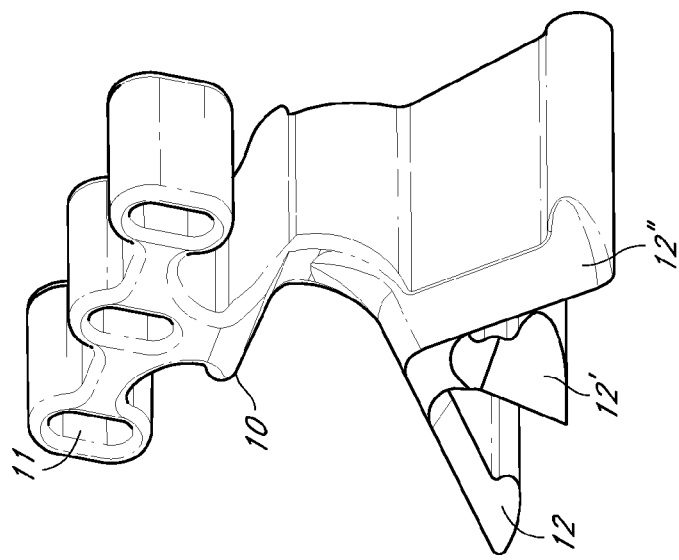

In FIG. 22A, another embodiment of an anchor is shown. Here, three legs defining the keel are provided. A relatively taller neck is provided beneath a perpendicular suture attachment member. The neck 10 is set back distally from the leading edge of the keel portion. FIG. 22B shows the distal tip of a delivery tool. Shown are attachment pins 180, anvil 186 or striking surface, depth stop 187, and mounting member 185.

Turning to FIG. 23A, an anchor 25 is shown with an attachment site for a flexible bridge 188. The bridge 188 is shown in FIG. 23B and is coupled to the neck 10 of the anchor 12 with a first and second flexible tab 193, 194 and has an attachment 11 site at the opposing end.

Figure 24A:
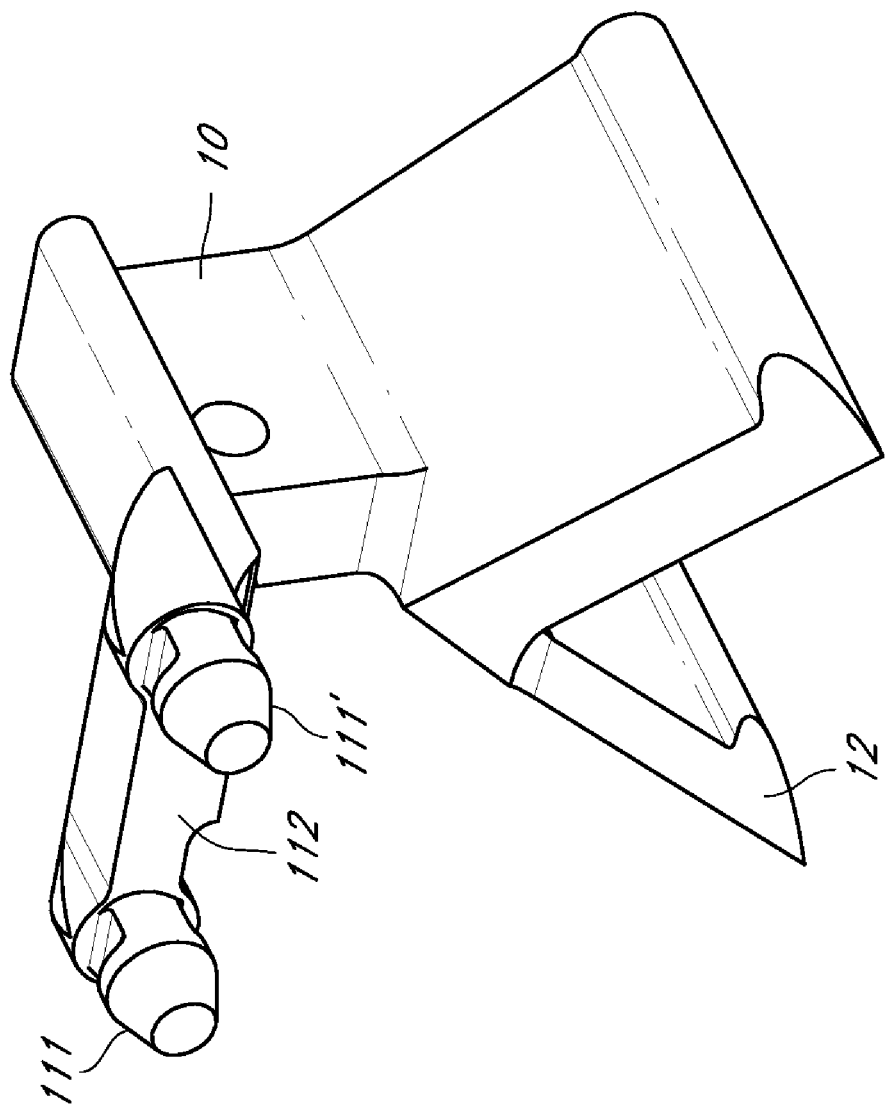
FIGS. 24A-C show a series of perspective views of one embodiment of an anchor and barrier system according to one or more embodiments of the invention.
Figure 24B:
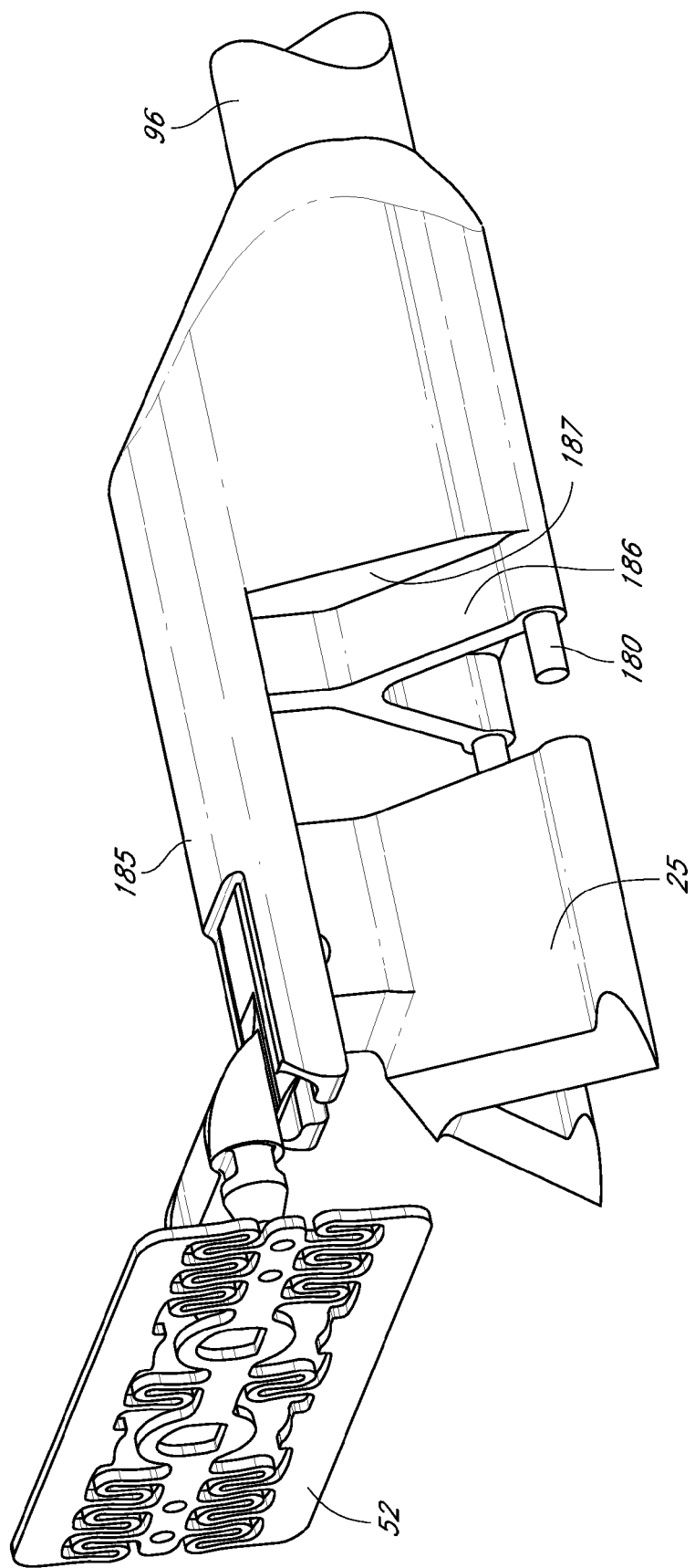
Figure 24C:
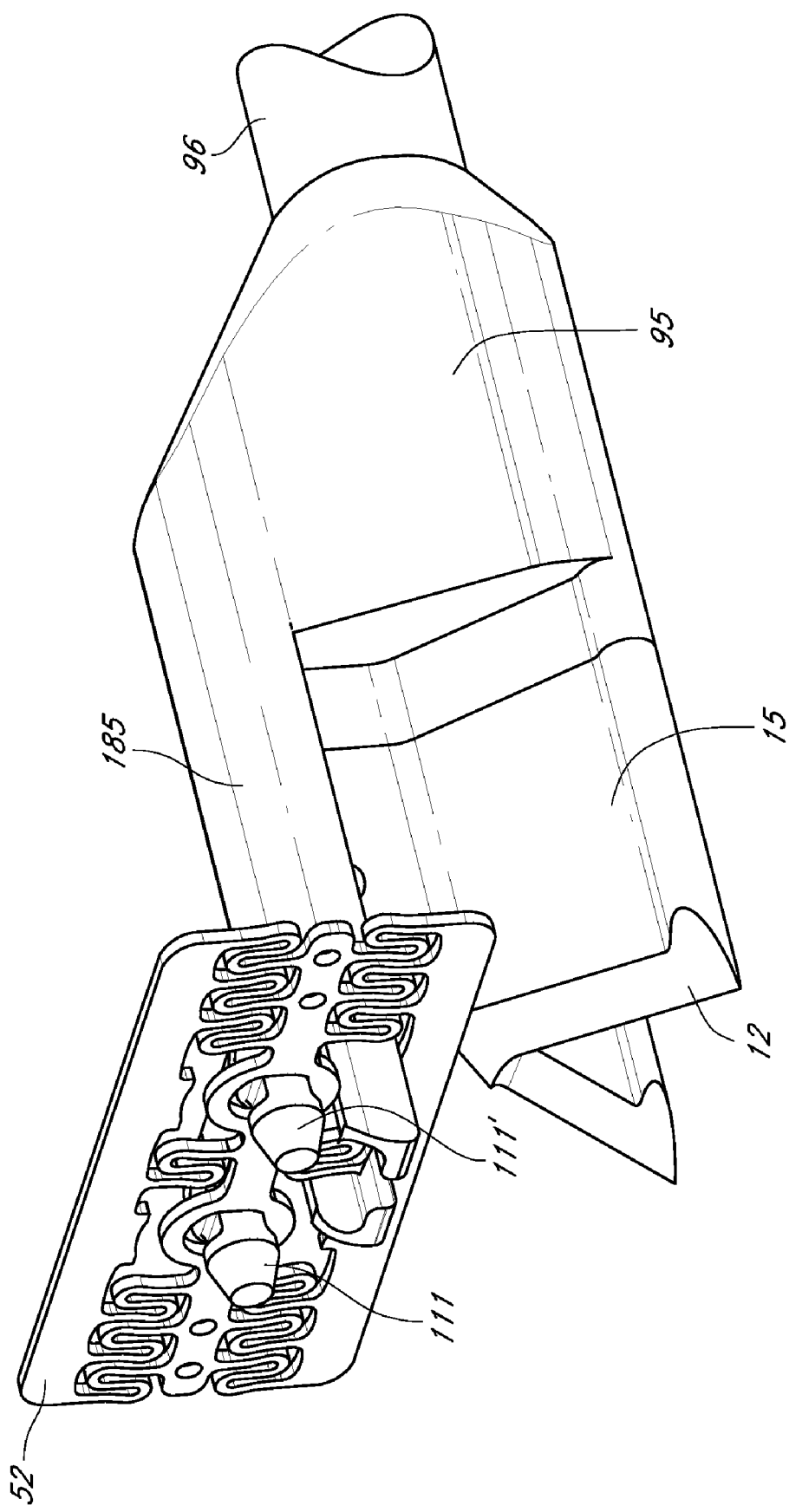

The series depicted in 24A-24C shows an anulus reinforcement system. FIG. 24A shows an anchor similar to the ones depicted previously with a bifurcated keel 15, 15', neck 10, and attachment plate 112 with a first and second coupling member 111, 11' or snap surface. FIG. 24B is an exploded view of a barrier, mesh, or reinforcement plate 52 adjacent an anchor wherein the anchor 25 is partially inserted or mounted within the distal end of a delivery tool. FIG. 24C shows all three elements connected and mounted and ready to be driven into a tissue site.

Figure 25A:
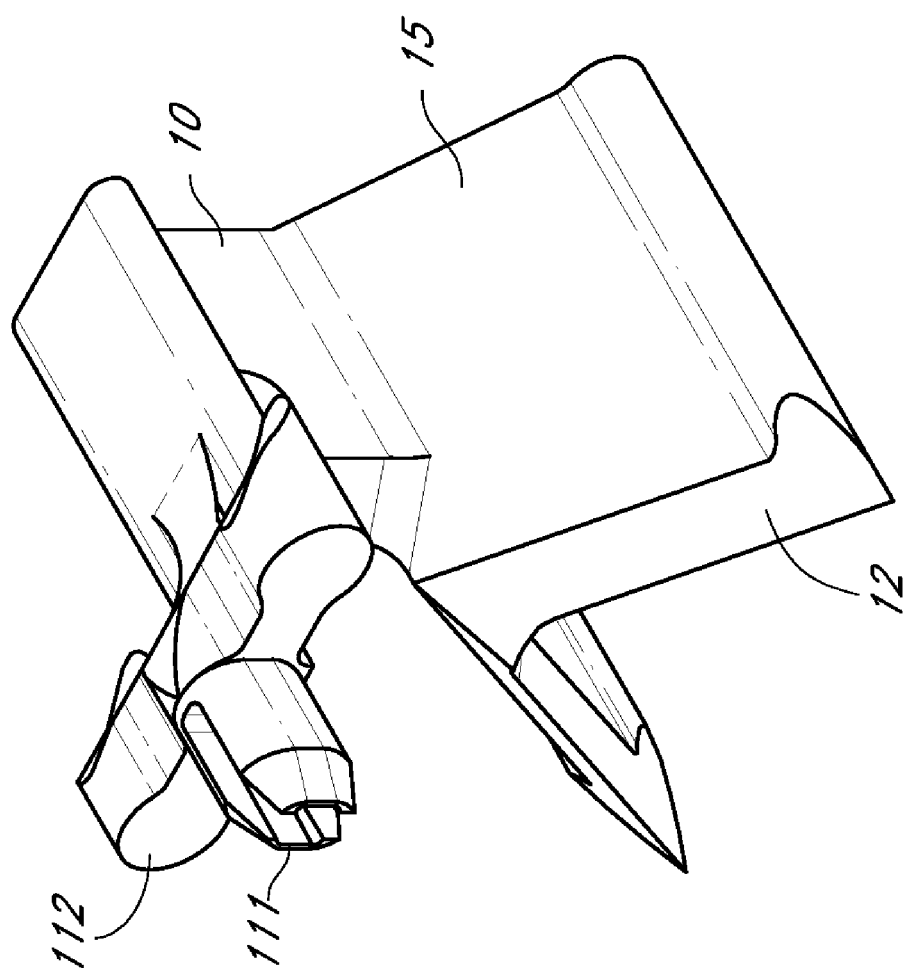
FIGS. 25A-C show a series of perspective views of another embodiment of an anchor and barrier system according to one or more embodiments of the invention.
Figure 25B:
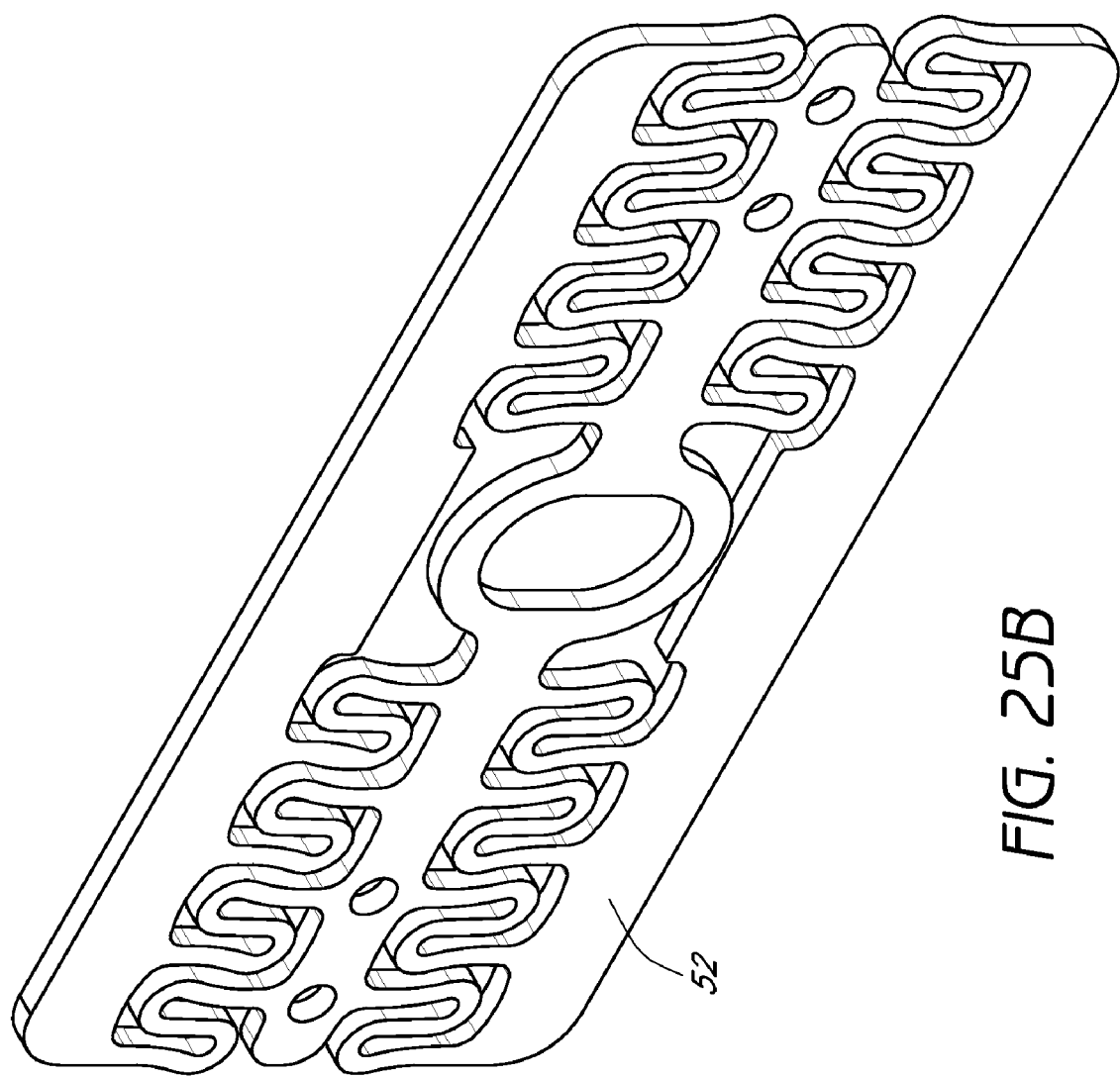
Figure 25C:
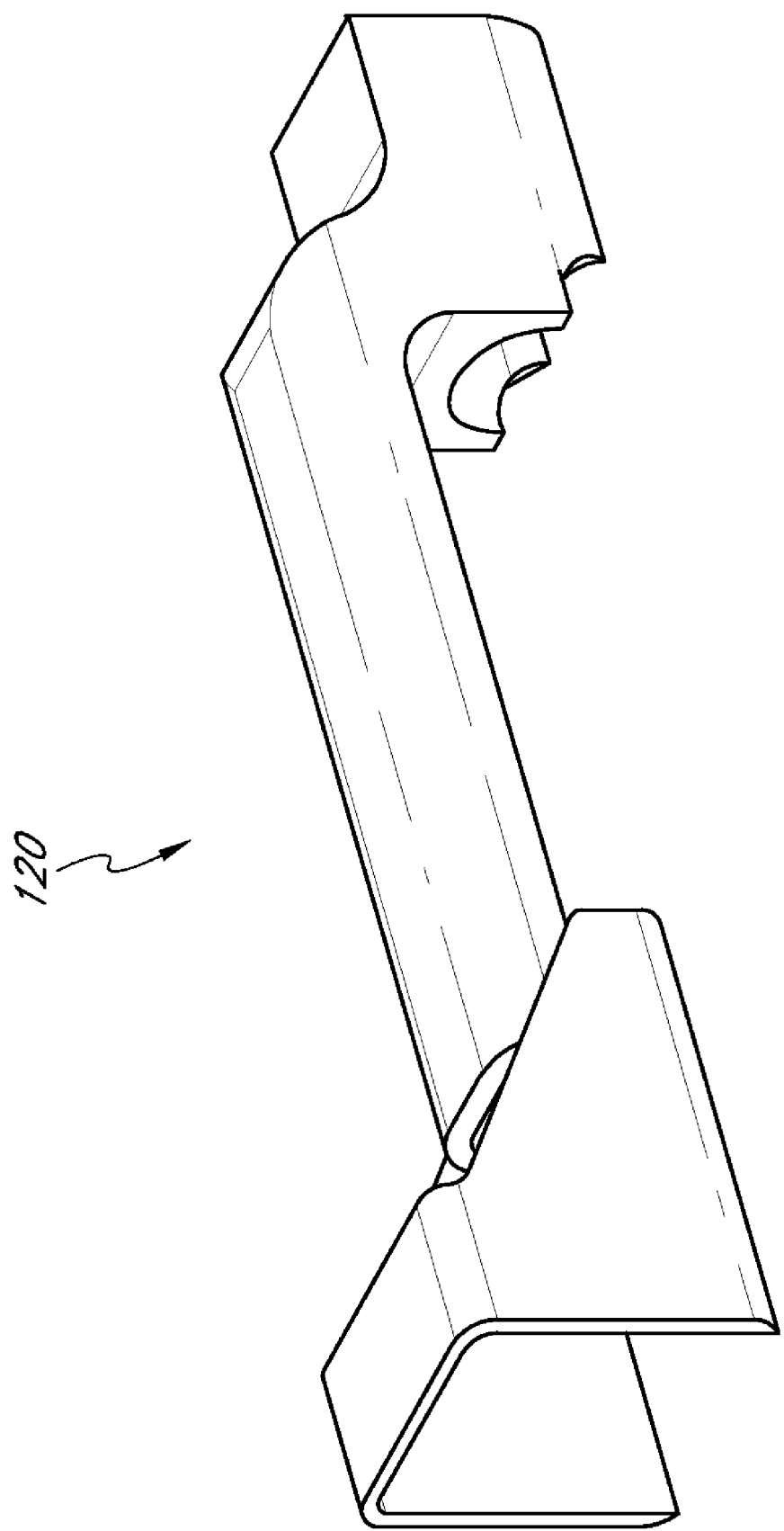

Another embodiment of an anulus reinforcement system is shown in FIGS. 25A-25C. In this embodiment, a single attachment means 111 is used that can function as a fulcrum or hinge site for a flexible barrier 52 member shown in FIG. 25B. Behind or distal to the attachment means 111 is a support member 112 or plate that is an extension of the neck 10. This feature, in some embodiments, minimizes or prevents the barrier 52 from folding backwards and may also reinforce the barrier 52. FIG. 25C shows a hood or sleeve 120 element that can be mounted on or carried by a delivery tool or instrument as described herein. The hood 120 retains the folded barrier until the anchor portion is fully established within the tissue whereupon it is retracted.

Another embodiment of the invention is shown in FIGS. 26A-26B. This embodiment shows an anchor especially adapted for use in a vertebral body and includes an upside down "V" shaped keel portion with a sharpened leading edge. The leading edges enable the anchor to be directly driven into the bone and do not require a pilot hole or pre-cut. and One feature of this embodiment is the leading step in the sharpened edge which present more cutting surface blow the surface of the bone and more forward of the distal attachment site. Alternatively, the leading edge can have multiple steps or be curved and rounded. This profile reduce the risk that the leading edge might pierce or damage the endplate (which is not flat but has a "dip" or cupped portion in the middle). This feature facilitates insertion of a longer, stronger anchor into a disc that would otherwise (because of a pronounced dip) be difficult to position at the proper height and depth into the bone without damaging the endplate.

Example

The following Example illustrates one embodiment of the present invention and is not intended in any way to limit the invention. Moreover, although the following Example describes an anchor used in a spinal application, the anchors described herein can be used throughout the human body and have general applicability to fastener art. Such anchors can be used to join or anchor like or disparate materials or tissues together, maintain alignment of materials, reinforce a fracture within a material, and provide an attachment site along or within a materials surface.

The anchor illustrated in FIG. 26 is used by way of example. The anchor is in the form of an upside down "Y" defined by a neck portion terminating at one end into two plate-like rectangular legs forming a keel and terminating into an suture attachment site 11 in the form of a loop on the other end. The leading edge of the legs 12 and neck 10 are sharpened and the upper portion of the legs is recessed, profiled or formed with a relief 113. The relief profile 113 can correspond to an anatomical structure, in this embodiment the forward recess or relief 112 corresponds to the concavity or cupping of an endplate. The angle between the keel plates is around 90 degrees. The neck 10 is about 0.1 millimeter high and about 0.2 wide millimeters wide and extends about 0.2 millimeters. The neck 10 and attachment site 11, an "eye" or loop in this embodiment, are mounted at the trailing or aft potion of the keel 15.

The entire structure is made of nickel titanium and is machined from bar stock. To be delivered, the anchor is mounted on the distal end of a driver. The driver has a striking surface on one end and an anvil on the opposing end. The anvil has the identical cross-section as the trailing edge of the anchor and extends about 0.2 cm to allow for countersinking. The anchor is coupled to the anvil by a forked protrusion that holds the neck and a pin that fits into the eye.

In one application, the anchor is used to secure an anulus repair device relative to a defect in the disc. A posterior-lateral approach is used to obtain access to the damaged disc. Part of the posterior elements on the opposing vertebral bodies may have to be removed in order to reach the disc. The anulus repair device is then implanted through the defect and along the inner surface of the anulus.

Next the anchor, which is mounted on the distal end of the driver, is aimed at the top edge or endplate of the inferior intervertebral body. An alignment projection forming a right angle at the tip of the drive is used to align the bottom potion of the attachment loop of the anchor with the upper surface of the endplate and to center the anchor within the defect. The anchor is then driven forward into the bone with light hammering applied to the driver. The anchor is driven roughly perpendicular to the outer surface of the vertebral body and roughly parallel to the endplate.

The depth of insertion is controlled by the 0.2 cm countersinking anvil and the depth dimension of the anchor, in this case 0.5 cm for a total depth of 0.7 cm which is still shy of the border of the cortical rim and the cupping of the endplate. Only the upper potion of the loop remains proud of the endplate surface and the annular repair device can then be connected to it with a suture.

It will be understood by those of skill in the art that numerous and various modifications can be made without departing from the spirit of the present invention. For example, method steps need not be performed in the order set forth herein. Therefore, it should be clearly understood that the forms of the present invention are illustrative only and are not intended to limit the scope of the present invention.

What is claimed is:

1. A method of establishing an anchor along an endplate adjacent an intervertebral disc, comprising:
   identifying a vertebral body comprising an outer surface and an endplate,
   wherein the outer surface is offset at an angle substantially perpendicular from the endplate and extends around a circumference of the vertebral body;
   identifying a defect in an intervertebral disc adjacent said vertebral body;
   providing a prosthetic barrier coupled to a bone anchor,
   wherein the prosthetic barrier is configured to repair the defect in the intervertebral disc,
   wherein the bone anchor comprises a neck,
   wherein said neck has a length defined by a sharpened leading edge and a trailing end,
   wherein said neck comprises an attachment site along at least a portion of its length,
   wherein said attachment site is attachable to the prosthetic barrier,
   wherein the attachment site is configured to extend above the endplate,
   wherein said neck comprises a bottom portion terminating in a keel portion,
   wherein said keel portion comprises a sharpened leading edge,
   wherein the attachment site is offset relative to both the anchor's angle of insertion and said neck to present said attachment site along the endplate, while said keel portion is inserted into the outer surface of the vertebral body;
   advancing the sharpened leading edge of the keel portion within the outer surface while simultaneously advancing the attachment site, and thereby the prosthetic barrier, along and across the endplate,
   wherein the bone anchor is driven within the outer surface of the vertebral body along a trajectory that is substantially perpendicular to the outer surface of the vertebral body and substantially parallel to the endplate;
   countersinking said bone anchor within said outer surface of the vertebral body such that no portion of said bone anchor lies beyond said outer surface of the vertebral body; and
   positioning the prosthetic barrier to close the defect.

2. The method of claim 1, wherein the keel portion comprises two keels that form an angle of about 180 degrees relative to each other, and wherein the neck is perpendicular to said keels to form a "T" shape.

3. The method of claim 1, wherein the prosthetic barrier comprises a polymer and the anchor comprises titanium.

4. The method of claim 1, wherein the prosthetic barrier and the anchor form a unitary construct.

5. The method of claim 1, wherein the prosthetic barrier comprises a mesh.

6. The method of claim 1, wherein the prosthetic barrier comprises a patch.

7. The method of claim 1, wherein the prosthetic barrier comprises a collapsible implant.

8. The method of claim 1, further comprising expanding at least one of the anchor or the prosthetic barrier.

9. The method of claim 1, wherein the attachment site comprises at least one device selected from the group consisting of: a fabric, a wire, a linkage, a fastener component, a hook eye, a loop, and a plate.

10. A method of establishing an anchor along an endplate adjacent an intervertebral disc, comprising:
    identifying a vertebral body comprising an outer surface and an endplate,
    wherein the outer surface of the vertebral body is offset at an angle substantially perpendicular from the endplate and extends around a circumference of the vertebral body;
    providing a prosthetic barrier coupled to a bone anchor,
    wherein the bone anchor comprises a neck,
    wherein said neck has a length defined by a sharpened leading edge and a trailing end,
    wherein said neck comprises an attachment site along at least a portion of its length,
    wherein said neck comprises a keel portion extending substantially perpendicularly from a bottom portion of the neck,
    wherein the attachment site is offset relative to both the anchor's angle of insertion and said neck to present said attachment site along the endplate, while said keel portion is inserted into the outer surface of the vertebral body;
    advancing a sharpened leading edge of the keel portion directly within the outer surface of the vertebral body while simultaneously advancing the attachment site, and thereby the prosthetic barrier, along and across the endplate,
    wherein the keel portion is driven within the outer surface of the vertebral body along a trajectory that is substantially perpendicular to the outer surface of the vertebral body and substantially parallel to the endplate; and
    countersinking said anchor within said outer surface of the vertebral body such that no portion of said anchor lies beyond said outer surface of the vertebral body.

11. The method of claim 10, further comprising identifying a defect in anulus tissue of the intervertebral disc.

12. The method of claim 11, wherein the defect comprises a hole.

13. The method of claim 12, further comprising positioning the prosthetic barrier to close the defect.

14. The method of claim 11, wherein the defect is a herniated segment of anulus tissue.

15. The method of claim 14, further comprising positioning the prosthetic barrier to contact the herniated segment and return the herniated segment to a preherniated border of the anulus, thereby preserving and containing the herniated segment.

16. A method of establishing an anchor along an endplate adjacent an intervertebral disc, comprising:
    identifying a vertebral body comprising an outer surface and an endplate,
    wherein the outer surface of the vertebral body is offset at an angle substantially perpendicular from the endplate and extends around a circumference of the vertebral body;
    wherein the identified vertebral body is adjacent an intervertebral disc having a herniated anulus segment;
    providing a prosthetic device coupled to a bone anchor,
    wherein the prosthetic device is configured to contain the herniated anulus segment,
    wherein the bone anchor comprises a neck,
    wherein said neck has a length defined by a sharpened leading edge and a trailing end,
    wherein said neck comprises an attachment site along at least a portion of its length,
    wherein said neck comprises a keel portion extending substantially perpendicularly from a bottom portion of the neck,
    advancing a sharpened leading edge of the keel portion directly within the outer surface of the vertebral body while simultaneously advancing the attachment site, and thereby the prosthetic device, along and across the endplate,
    wherein the keel portion is driven within the outer surface of the vertebral body along a trajectory that is substantially perpendicular to the outer surface of the vertebral body and substantially parallel to the endplate; and
    countersinking said anchor within said outer surface of the vertebral body such that no portion of said anchor lies beyond said outer surface of the vertebral body.

17. The method of claim 16, further comprising positioning the prosthetic device to contact the herniated anulus segment and return the herniated anulus segment to a preherniated border of the anulus, thereby preserving and containing the herniated segment.

18. The method of claim 16, wherein the prosthetic device comprises a prosthetic barrier.

19. The method of claim 18, wherein the prosthetic barrier comprises a polymer.

20. The method of claim 16, wherein the bone anchor comprises titanium.

* * * * *